(12) United States Patent
Aghajanian et al.

(10) Patent No.: US 7,320,789 B2
(45) Date of Patent: Jan. 22, 2008

(54) ANTIBODY INHIBITORS OF GDF-8 AND USES THEREOF

(75) Inventors: Jane Aghajanian, deceased, late of Belgrade, ME (US); by William J. Dunham, legal representative, Belgrade, ME (US); Neil M. Wolfman, Dover, MA (US); Denise O'Hara, Reading, MA (US); Monique V. Davies, Harpswell, MA (US); Geertruida M. Veldman, Sudbury, MA (US); Kristie Grove Bridges, Maynard, MA (US); Lisa-Anne Whittemore, East Walpole, MA (US)

(73) Assignee: Wyeth, Madison, NJ (US)

( * ) Notice: Subject to any disclaimer, the term of this patent is extended or adjusted under 35 U.S.C. 154(b) by 685 days.

(21) Appl. No.: 10/253,532

(22) Filed: Sep. 25, 2002

(65) Prior Publication Data

US 2003/0138422 A1    Jul. 24, 2003

Related U.S. Application Data

(60) Provisional application No. 60/324,528, filed on Sep. 26, 2001.

(51) Int. Cl.
    A61K 39/00    (2006.01)
    C07K 16/00    (2006.01)
    C12N 5/16     (2006.01)

(52) U.S. Cl. .................. 424/130.1; 424/133.1; 424/135.1; 424/141.1; 435/326; 530/387.1; 530/388.1

(58) Field of Classification Search .......... 435/4, 435/7.1, 325, 326; 424/130.1, 141.1; 530/300, 530/350
    See application file for complete search history.

(56) References Cited

U.S. PATENT DOCUMENTS

| | | | |
|---|---|---|---|
| 5,639,638 A | 6/1997 | Wozney et al. | |
| 5,700,911 A | 12/1997 | Wozney et al. | |
| 5,723,125 A | 3/1998 | Chang et al. | |
| 5,756,457 A | 5/1998 | Wang et al. | |
| 5,827,733 A | 10/1998 | Lee et al. | |
| 5,914,234 A | 6/1999 | Lee et al. | |
| 5,928,893 A * | 7/1999 | Kang et al. | 435/69.1 |
| 5,994,618 A | 11/1999 | Lee et al. | |
| 6,004,937 A | 12/1999 | Wood et al. | |
| 6,096,506 A | 8/2000 | Lee et al. | |
| 6,340,668 B1 | 1/2002 | Celeste et al. | |
| 6,368,597 B1 | 4/2002 | Strassmann et al. | |
| 6,369,201 B1 | 4/2002 | Barker et al. | |
| 6,437,111 B1 | 8/2002 | Wozney et al. | |
| 6,656,475 B1 * | 12/2003 | Lee et al. | 424/198.1 |
| 6,696,260 B1 | 2/2004 | Lee et al. | |
| 6,835,544 B2 | 12/2004 | Mathews et al. | |
| 2002/0150577 A1 | 10/2002 | Lee et al. | |
| 2003/0104406 A1 | 6/2003 | Wolfman et al. | |
| 2003/0162714 A1 | 8/2003 | Hill et al. | |
| 2003/0180306 A1 | 9/2003 | Hill et al. | |
| 2004/0077053 A1 | 4/2004 | Lee et al. | |
| 2004/0138118 A1 | 7/2004 | Wolfman et al. | |
| 2004/0142382 A1 | 7/2004 | Veldman et al. | |
| 2004/0181033 A1 | 9/2004 | Han et al. | |
| 2004/0223966 A1 | 11/2004 | Wolfman et al. | |
| 2005/0043232 A1 | 2/2005 | Lee et al. | |

FOREIGN PATENT DOCUMENTS

| | | |
|---|---|---|
| EP | 1 061 940 B1 | 12/2003 |
| EP | 1 444 985 A2 | 8/2004 |
| WO | WO94-21681 | 9/1994 |
| WO | WO94-26892 | 11/1994 |
| WO | WO96-01845 | 1/1996 |
| WO | WO98/33887 | 8/1998 |
| WO | WO99-24058 | 5/1999 |
| WO | WO99-45949 | 9/1999 |
| WO | WO99-56768 | 11/1999 |
| WO | WO 00-11163 | 3/2000 |
| WO | WO 00-43781 | 7/2000 |
| WO | WO 01/64888 A2 | 9/2001 |
| WO | WO 02-09641 A2 | 2/2002 |
| WO | WO 02-068650 A2 | 9/2002 |
| WO | WO 03/072714 A2 | 9/2003 |
| WO | WO 03/072715 A2 | 9/2003 |
| WO | WO 04-058988 A2 | 7/2004 |

OTHER PUBLICATIONS

Suzuki et al., Oncogene 19: 5842-5850, 2000.*
Chamov and Ashkanazi, TIBTECH 14: 52-60, 1996.*
Wells, Biochemistry 29:8509-8517, 1990.*
Ngo et al., The Protein Folding Problem and Tertiary Structure Prediction, pp. 492-495, 1994.*
Rudikoff et al., Proc. Natl. Acad. Sci. 79: 1979-1983, 1982.*
Alexander et al., "Human Parathyroid Hormone 1-34 Reverses Bone Loss In Ovariectomized Mice," *J. Bone Miner. Res.* 16:1665-1673 (2001).
Alliel et al., "Testican, a Multidomain Testicular Proteoglycan Resembling Modulators of Cell Social Behaviour," *Eur. J. Biochem.* 214:347-350 (1993).
Amthor et al., "The Expression and Regulation of Follistatin and a Follistatin-like Gene During Avian Somite Compartmentalization and Myogenesis," *Dev. Biol.* 178:343-362 (1996).

(Continued)

Primary Examiner—Gary Nickol
Assistant Examiner—Gyan Chandra
(74) Attorney, Agent, or Firm—Finnegan, Henderson, Farabow, Garrett, & Dunner, L.L.P.

(57) ABSTRACT

The disclosure provides novel antibodies against growth and differentiation factor-8 (GDF-8), including antibody fragments, which inhibit GDF-8 activity in vitro and in vivo. The disclosure also provides methods for diagnosing, preventing, or treating degenerative disorders of muscle, bone, or insulin metabolism.

35 Claims, 27 Drawing Sheets

OTHER PUBLICATIONS

Andersson et al., "Repeated In Vivo Determinations of Bone Mineral Density During Parathyroid Hormone Treatment in Ovariectomized Mice," *J. Endocrinol.* 170:529-537 (2001).

Ashmore et al., "Comparative Aspects of Muscle Fiber Types in Fetuses of the Normal and "Double-Muscled" Cattle," *Growth* 38:501-506 (1974).

Attisano et al., "Activation of Signalling by the Activin Receptor Complex," *Mol. Cell. Biol.* 16:1066-1073 (1996).

Bakker et al., Duchenne and Becker Muscular Dystrophies. In *Diagnostic Criteria for Neuromuscular Disorders*, 2nd ed., Emery, ed., Royal Society of Medicine Press, 1998; pp. 1-4.

Bartholin et al., "FLRG, an Activin-Binding Protein, is a New Target of TGFβ Transcription Activation Through Smad Proteins," *Oncogene* 20:5409-5419 (2001).

Bogdanovich et al., "Functional Improvement of Dystrophic Muscle by Myostatin Blockade," *Nature* 420:418-421 (2002).

Brown et al., "Physicochemical Activation of Recombinant Latent Transforming Growth Factor-beta's 1, 2, and 3," *Growth Factors* 3:35-43 (1990).

Bulfield et al., "X Chromosome-Linked Muscular Dystrophy (*mdx*) in the Mouse," *Proc. Natl. Acad. Sci. U.S.A.* 81:1189-1192 (1984).

D'Angelo et al., "Authentic Matrix Vesicles Contain Active Metalloproteases (MMP)," *J. Biol. Chem.* 276:11347-11353 (2001).

Derynck et al., "Human Transforming Growth Factor-β Complementary DNA Sequence and Expression in Normal and Transformed Cells," *Nature* 316:701-705 (1985).

Donoghue et al., "Rostrocaudal Gradient of Transgene Expression in Adult Skeletal Muscle," *Proc. Natl. Acad. Sci. U.S.A.* 88:5847-5851 (1991).

Emery, "The Muscular Dystrophies," *Lancet* 359:687-695 (2002).

Escolar et al., "Pharmacologic and Genetic Therapy for Childhood Muscular Dystrophies," *Current Neurology and Neuroscience Reports* 1:168-174 (2001).

Gamer et al., "A Novel BMP Expressed in Developing Mouse Limb, Spinal Cord, and Tail Bud Is a Potent Mesoderm Inducer in *Xenopus* Embryos," *Dev. Biol.* 208:222-232 (1999).

Gamer et al., "Gdf11 is a Negative Regulator of Chodrogenesis and Myogenesis in the Developing Chick Limb," *Dev. Biol.* 229:407-420 (2001).

Gentry et al., "The Pro Domain of Pre-Pro-Transforming Growth Factor β1 When Independently Expressed Is a Functional Binding Protein for the Mature Growth Factor," *Biochemistry* 29:6851-6857 (1990).

Gillis, "Multivariate Evaluation of the Functional Recovery Obtained by the Overexpression of Utrophin in Skeletal Muscles of the *mdx* Mouse," *Neuromuscular Disorders* 12:S90-S94 (2002).

Gonzalez-Cadavid et al., "Organization of the Human Myostatin Gene and Expression in Healthy Men and HIV-Infected Men With Muscle Wasting," *Proc. Natl. Acad. Sci. U.S.A.* 95:14938-14943 (1998).

Grady et al., "Skeletal and Cardiac Myopathies in Mice Lacking Utrophin and Dystrophin: A Model for Duchenne Muscular Dystrophy," *Cell* 90:729-738 (1997).

Granchelli et al., "Pre-Clinical Screening of Drugs Using the *mdx* Mouse," *Neuromuscular Disorders* 10:235-239 (2000).

Hamrick et al., "Bone Mineral Content and Density in the Humerus of Adult Myostatin-Deficient Mice," *Calcif. Tissue International.* 71(1):63-68 (2002).

Hamrick et al., "Fermoral Morphology and Cross-Sectional Geometry of Adult Myostatin-Deficient Mice," *Bone* 27:343-349 (2000).

Hayette et al., "FLRG (Follistatin-Related Gene), A New Target of Chromosomal Rearrangement in Malignant Blood Disorders," *Oncogene* 16:2949-2954 (1998).

Hill et al., "Regulation of Mystatin in Vivo by Growth and Differentiation Factor-Associated Serum Protein-1: A Novel Protein with Protease Inhibitor and Follistatin Domains," *Mol. Endocrinol.* 17:1144-1154 (2003).

Hill et al., "The Myostatin Propeptide and the Follistatin-Related Gene Are Inhibitory Binding Proteins of Myostatin Normal Serum," *J. Biol. Chem.* 277:40735-40741 (2002).

Hoffman et al., "Conservation of the Duchenne Muscluar Dystrophy Gene in Mice and Humans," *Science* 238:347-350 (1987).

Hoodless et al., "Mechanisms and Function of Signaling by the TGFβ Superfamily," *Curr. Top. Microbiol. Immunol.* 228:236-272 (1998).

Huet et al., "Skeletal Muscle Cell Hypertrophy Induced by Inhibitors of Metalloproteases; Myostatin as a Potential Mediator," *Am. J. Physiol. Cell. Physiol.* 281:C1624-C1634 (2001).

Jiang et al., "Characterization and Identification of the Inhibitory Domain of GDF-8 Propeptide," *Biochem. Biophys. Res. Commun.* 315:525-531 (2004).

Kambadur et al., "Mutations in *myostatin* (GDF8) In Double-Muscled Belgian Blue and Piedmontese Cattle," *Genome Res.* 7:910-915 (1997).

Kato, "A Secreted Tumor-Suppressor, mac25, with Activin-Binding Activity," *Mol. Med.* 6:126-135 (2000).

Kessler et al., "Bone Morphogenetic Protein-1: The Type 1 Procollagen C-Proteinase," *Science* 271:360-362 (1996).

Khurana et al., "Pharmacological Strategies for Muscluar Dystrophy," *Nature Rev. Drug Disc.* 2:379-386 (2003).

Kim et al., "Inhibition of Preadipocyte Differentiation by Myostatin Treatment in 3T3-L1 Cultures," *Biochem. Biophys. Res. Commun.* 281:902-906 (2001).

Kingsley, D.M., "The TGF-β Superfamily: New Members, New Receptors, and New Genetic Tests of Function in Different Organisms," *Genes Dev.* 8:133-146 (1994).

Lang et al., "Regulation of Myostatin by Glucocorticoids After Thermal Injury," *FASEB J.* 15:1807-1809 (2001).

Lee et al., "Analysis of Site-Directed Mutations in Human Pro-α2(I) Collagen Which Block Cleavage by the C-Proteinase," *J. Biol. Chem.* 265:21992-21996 (1990).

Lee et al., "Regulation of Myostatin Activity and Muscle Growth," *Proc. Natl. Acad. Sci. U.S.A.* 98:9306-9311 (2001).

Li et al., "The C-Proteinase that Processes Procollagens to Fibrillar Collagens is Identical to the Protein Previously Identified as Bone Morphogenic Protein-1," *Proc. Natl. Acad. Sci. U.S.A.* 93:5127-5130 (1996).

Lin et al., "Expression Cloning of the TGF-β Type II Receptor, a Functional Transmembrane Serine/Threonine Kinase," *Cell* 68:775-785 (1992).

Liu et al., "Assigning the Positional Identity of Spinal Motor Neurons: Rostrocaudal Patterning of Hox-c Expression by FGFs, Gdf11, and Retinoids," *Neuron* 32:997-1012 (2001).

Lyons et al., "Proteolytic Activation of Latent Transforming Growth Factor-β from Fibroblast-Conditioned Medium," *J. Cell Biol.* 106:1659-1665 (1988).

Maeda et al., "Activation of Latent Transforming Growth Factor β1 by Stromelysin 1 in Extracts of Growth Plate Chondrocyte-Derived Matrix Vesicles," *J. Bone Miner. Res.* 16:1281-1290 (2001).

Maguer-Satta et al., "During Hematopoiesis, Expression of FLRG, a Novel Activin A Ligand, is regulated by TGF-β," *Exp. Hematol.* 29:301-308 (2001).

Marques et al., "Production of a DPP Activity Gradient in the Early Drosophilia Embryo through the Opposing Actions of the SOG and TLD Proteins," *Cell* 91:417-426 (1997).

Massagué et al., "Receptors for the TGF-β Family," *Cell* 69:1067-1070 (1992).

Massagué et al., "The TGF-β Family and its Composite Receptors," *Trends Cell Biol.* 4:172-178 (1994).

Massagué "How Cells Read TGF-β Signals," *Nature Rev. Mol. Cell. Biol.* 1:169-178 (2000).

Massagué, "The Transforming Growth Factor-β Family," *Annu. Rev. Cell Biol.* 6:597-641 (1990).

Matsuda et al., "Visualization of Dystrophic Muscle Fibers in Mdx Mouse by Vital Staining with Evans Blue: Evidence of Apoptosis in Dystrophin-Deficient Muscle," *J. Biochem.* 118:959-964 (1995).

McPherron et al., "Double Muscling in Cattle Due to Mutations in the Myostatin Gene," *Proc. Natl. Acad. Sci. U.S.A.* 94:12457-12461 (1997).

McPherron et al., "Regulation of Anterior/Posterior Patterning of the Axial Skeleton by Growth/Differentiation Factor 11," *Nature Genet.* 22:260-264 (1999).

McPherron et al., "Regulation of Skeletal Muscle Mass in Mice by a New TGF-β Superfamily Member," *Nature* 387:83-90 (1997).

McPherron et al., "Suppression of Body Fat Accumulation in Myostatin-Deficient Mice," *J. Clin. Invest.* 109:595-601 (2002).

Miyazono et al., "Latent High Molecular Weight Complex of Transforming Growth Factor β1," *J. Biol. Chem.* 263:6407-6415 (1988).

Morrison et al., "T-Cell-Dependent Fibrosis in the mdx Dystrophic Mouse," *Lab. Invest.* 80:881-891 (2000).

Motamed, "Molecules in Focus, SPARC (Osteonectin/BM-40)," *Int. J. Biochem. Cell Biol.* 31:1363-1366 (1999).

Moustakas et al., "Smad Regulation in TGF-β Signal Transduction," *J. Cell Sci.* 114:4359-4369 (2001).

Nakamura et al., "Follistatin, an Activin-Binding Protein, Associates with Heparan Sulfate Chains of Proteoglycans on Follicular Granulosa Cells," *J. Biol. Chem.* 266:19432-19437 (1991).

Nakamura et al., "Isolation and Characterization of Activin Receptor from Mouse Embryonal Carcinoma Cells," *J. Biol. Chem.* 267:18924-18928 (1992).

Nakashima et al., "Expression of Growth/Differentiation Factor 11, A New Member of the BMP/TGF β Superfamily During Mouse Embryogenesis," *Mech. Dev.* 80:185-189 (1999).

Ngo et al., In *The Protein Folding Problems and Tertiary Structure Prediction,* Merz et al., eds., *Brickhauser,* Springer Verlag, Boston, pp. 433-434 & 492-495 (1994).

Pappano et al., "Use of BMP1-Tll1 Doubly Homozygous Null Mice and Proteomics to Identify and Validate In Vivo Substrates of Bone Morphogenetic Protein 1/Tolloid-Like Metalloproteinases," *Mol. Cell. Biol.* 23:4428-4438 (2003).

Patel et al., "Cloning and Early Dorsal Axial Expression of Flik, a Chick Follistatin-Related Gene: Evidence for Involvement in Dorsalization-Neural Induction," *Dev. Biol.* 178: 327-342 (1996).

Patthy et al., "Functions of Agrin and Agrin-Related Proteins," *Trends Neurosci.* 16:76-81 (1993).

Phillips et al., "Follistatin: A Multifunctional Regulatory Protein," *Front. Neuroendocrin.* 19:287-322 (1998).

Piccolo et al., "Cleavage of Chrodin by Xolloid Metalloprotease Suggests a Role for Proteolytic Processing in the Regulation of Spemann Organizer Activity," *Cell* 91:407-416 (1997).

R&D Systems, Inc., "Recombinant Human Activin Receptor IIB-Fc Chimera: Specifications and Use," Cat. No. 339-RB (2002).

Riley et al., "The Use of Single Nucleotide Polymorphisms in the Isolation of Common Disease Genes," *Pharmacogenomics* 1:39-47 (2000).

Sato et al., "Inhibition of Endothelial Cell Movement by Pericytes and Smooth Muscle Cells: Activation of a Latent Transforming Growth Factor-β1-Like Molecule by Plasmin During Co-Culture," *J. Cell Biol.* 109:309-315 (1989).

Schäcke et al., "Mechanisms Involved in the Side Effects of Glucocorticoids," *Pharmacol. Ther.* 96:23-43 (2002).

Schneyer et al., "Follistatin-Related Protein (FSRP): A New Member of the Follistatin Gene Family," *Mol. Cell. Endocrinol.* 180:33-38 (2001).

Scott et al., "Bone Morphogenetic Protein-1 Processes Probiglycan," *J. Biol. Chem.* 275:30504-30511 (2000).

Scott et al., "Mammalian BMP-1-Tolloid-Related Metalloproteinases, Including Novel Family Member Mammalian Tollid-Like 2, Have Differential Enzymatic Activities and Distributions of Expression Relevant to Patterning and Skeletogenesis," *Dev. Biol.* 213:283-300 (1999).

Shibanuma et al., "Cloning From a Mouse Osteoblastic Cell Line of a Set of Transforming-Growth-Factor-β1-Regulated Genes, One of Which Seems to Encode a Follistatin-Related Polypeptide," *Eur. J. Biochem.* 217:13-19 (1993).

Sternberg et al., "Identification of Upstream and Intragenic Regulatory Elements that Confer Cell-Type-Restricted and Differentiation-Specific Expression on the Muscle Creatine Kinase Gene," *Mol. Cell. Biol.* 8:2896-2909 (1988).

Swatland et al., "Fetal Development of the Double Muscled Condition in Cattle," *J. Anim. Sci.* 38:752-757 (1974).

Takahara et al., "Bone Morphogenetic Protein-1 and a Mammalian Tolloid Homologue (mTld) Are Encoded by Alternatively Spliced Transcrips Which Are Differentially Expressed in Some Tissues," *J. Biol. Chem.* 269:32572-32578 (1994).

Takahara et al., "Characterization of a Novel Gene Product (Mammalian Tolloid-like) with High Sequence Similarity to Mammalian Tolloid/Bone Morphogenetic Protein-1," *Genomics* 34:157-165 (1996).

Thies et al., "GDF-8 Propeptide Binds to GDF-8 and Antagonizes Biological Activity by Inhibiting GDF-8 Receptor Binding," *Growth Factors* 18:251-259 (2000).

Torres et al., "The Mutant mdx: Inherited Myopathy in the Mouse," *Brain* 110:269-299 (1987).

Trexler et al., "A Human Protein Containing Multiple Types of Protease-Inhibitory Modules," *Proc. Natl. Acad. Sci. U.S.A.* 98:3705-3709 (2001).

Trexler et al., "Distinct Expression Pattern of Two Related Human Proteins Containing Multiple Types of Protease-Inhibitory Modules," *Biol. Chem.* 383:223-228 (2002).

Tsuchida et al., "Identification and Characterization of a Novel Follistatin-like Protein as a Binding Protein for the TGF-β Family," *J. Biol. Chem.* 275:40788-40796 (2000).

Tsuchida et al., "Intracellular and Extracellular Control of Activin Function by Novel Regulatory Molecules," *Mol. Cell. Endocrinol.* 180:25-31 (2001).

Umland et al., "Review of the Molecular and Cellular Mechanisms of Action of Glucocorticoids for Use in Asthma," *Pulmonary Pharmacology & Therapeutics* 15:35-50 (2002).

Uzel et al., "Multiple Bone Morphogenetic Protein 1-Related Mammalian Metalloproteinases Process Pro-Lysyl Oxidase at the Correct Physiological Site and Control Lysyl Oxidase Activation in Mouse Embryo Fibroblast Cultures," *J. Biol. Chem.* 276:22537-22543 (2001).

Wagner et al., "Loss of Myostatin Attenuates Severity of Muscular Dystrophy in mdx Mice," *Ann. Neurol.* 52:832-836 (2002).

Wakefield et al., "Latent Transforming Growth Factor-β From Human Platelets," *J. Biol. Chem.* 263:7646-7654 (1988).

Whittemore et al., "Inhibition of Myostatin in Adult Mice Increases Skeletal Muscle Mass and Strength," *Biochem. Biophys. Res. Commun.* 300:965-971 (2003).

Wolfman et al., "Activation of Latent Myostatin by the BMP-1/Tolloid Family of Metalloproteinases," *Proc. Natl. Acad. Sci. U.S.A.* 100:15842-15846 (2003).

Wu et al., "Autoregulation of Neurogenesis by GDF-11," *Neuron* 37:197-207 (2003).

Wuytens et al., "Identification of Two Amino Acids in Activin A That Are Important for Biological Activity and Binding to the Activin Type II Receptors," *J. Biol. Chem.* 274:9821-9827 (1999).

Yu et al., "Cell Surface-Localized Matrix Metalloproteinase-9 Proteolytically Activates TGF-β and Promotes Tumor Invasion and Angiogenesis," *Genes Dev.* 14:163-176 (2000).

Zhu et al., "Dominant Negative Myostatin Produces Hypertrophy without Hyperplasia in Muscle," *FEBS Lett.* 474:71-75 (2000).

Zimmers et al., "Induction of Cachexia in Mice by Systematically Administered Myostatin," *Science* 296: 1486-1488 (2002).

Zwusen et al., "Characterization of a Rat $C_8$ Glioma-Secreted Follistain-Related Protein (FRP) Cloning and Sequence of the Human Homologue," *Eur. J. Biochem.* 225:937-946 (1994).

Supplemenetal European Search Report in EP 02 78 3984 dated Oct. 5, 2005.

Harlow et al., *Using Antibodies, A Laboratory Manual,* Cold Spring Harbor Laboratory Press, Cold Spring Harbor, NY, p. 47 (1998).

Presta, *J. Allergy Clin. Immunol.* 116:731-736 (2005).

U.S. Appl. No. 10/071,499, filed Feb. 8, 2002.

International Search Report, mailed Feb. 4, 2003, based on PCT/US02/30452.

International Search Report, mailed Feb. 25, 2003, based on PCT/US02/03467.

\* cited by examiner

GDF-8 versus BMP-11

```
GDF-8:   DFGLDCDEHSTESRCCRYPLTVDFEAFGWDWIIAPKRY
BMP-11:  NLGLDCDEHSSESRCCRYPLTVDFEAFGWDWIIAPKRY
            _        __

KANYCSGECEFVFLQKYPHTHLVHQANPRGSAGPCCTPTKMSPINM
KANYCSGQCEYMFMQKYPHTHLVQQANPRGSAGPCCTPTKMSPINM
      _  _ _ _      __

LYFNGKEQIIYGKIPAMVVDRCGCS  (SEQ ID NO:15)
LYFNDKQQIIYGKIPGMVVDRCGCS  (SEQ ID NO:16)
    _ __         _
```

FIG. 3

| | | | |
|---|---|---|---|
| SEQ ID NO: 17 | DFGLDSDEHSTES | SEQ ID NO: 41 | FVFLQKYPHTHLV |
| SEQ ID NO: 18 | GLDSDEHSTESRS | SEQ ID NO: 42 | FLQKYPHTHLVHQ |
| SEQ ID NO: 19 | DSDEHSTESRSSR | SEQ ID NO: 43 | QKYPHTHLVHQAN |
| SEQ ID NO: 20 | DEHSTESRSSRYP | SEQ ID NO: 44 | PHTHLVHQANPRG |
| SEQ ID NO: 21 | HSTESRSSRYPLT | SEQ ID NO: 45 | THLVHQANPRGSA |
| SEQ ID NO: 22 | TESRSSRYPLTVD | SEQ ID NO: 46 | LVHQANPRGSAGP |
| SEQ ID NO: 23 | SRSSRYPLTVDFE | SEQ ID NO: 47 | HQANPRGSAGPSS |
| SEQ ID NO: 24 | SSRYPLTVDFEAF | SEQ ID NO: 48 | ANPRGSAGPSSTP |
| SEQ ID NO: 25 | RYPLTVDFEAFGW | SEQ ID NO: 49 | PRGSAGPSSTPTK |
| SEQ ID NO: 26 | PLTVDFEAFGWDW | SEQ ID NO: 50 | GSAGPSSTPTKMS |
| SEQ ID NO: 27 | TVDFEAFGWDWII | SEQ ID NO: 51 | AGPSSTPTKMSPI |
| SEQ ID NO: 28 | DFEAFGWDWIIAP | SEQ ID NO: 52 | PSSTPTKMSPINM |
| SEQ ID NO: 29 | EAFGWDWIIAPKR | SEQ ID NO: 53 | STPTKMSPINMLY |
| SEQ ID NO: 30 | FGWDWIIAPKRYK | SEQ ID NO: 54 | PTKMSPINMLYFN |
| SEQ ID NO: 31 | WDWIIAPKRYKAN | SEQ ID NO: 55 | KMSPINMLYFNGK |
| SEQ ID NO: 32 | WIIAPKRYKANYS | SEQ ID NO: 56 | SPINMLYFNGKEQ |
| SEQ ID NO: 33 | IAPKRYKANYSSG | SEQ ID NO: 57 | INMLYFNGKEQII |
| SEQ ID NO: 34 | PKRYKANYSSGES | SEQ ID NO: 58 | MLYFNGKEQIIYG |
| SEQ ID NO: 35 | RYKANYSSGESEF | SEQ ID NO: 59 | YFNGKEQIIYGKI |
| SEQ ID NO: 36 | KANYSSGESEFVF | SEQ ID NO: 60 | NGKEQIIYGKIPA |
| SEQ ID NO: 37 | NYSSGESEFVFLQ | SEQ ID NO: 61 | KEQIIYGKIPAMV |
| SEQ ID NO: 38 | SSGESEFVFLQKY | SEQ ID NO: 62 | QIIYGKIPAMVVD |
| SEQ ID NO: 39 | GESEFVFLQKYPH | SEQ ID NO: 63 | IYGKIPAMVVDRS |
| SEQ ID NO: 40 | SEFVFLQKYPHTH | SEQ ID NO: 64 | KIPAMVVDRSGSS |

FIG. 6A

Binding of JA-16 to Overlapping 13-mers Corresponding to GDF8

DFGLDSDEHSTESRSSRYPLTVDFEAFGWDWIIAPKRYKANYSSGESEFVFLQKY

1

2

3

4

PHTHLVHQANPRGSAGPSSTPTKMSPINMLYFNGKEQIIYGKIPAMVVDRSGSS (SEQ ID NO:14)

FIG. 6B

Binding of JA-16 to the GDF8-Derived Peptide GLDSDEHSTESRS (SEQ ID NO:18) Substitution and Deletion Analysis

Peptides to which binding could be detected are underlined

| | | | |
|---|---|---|---|
| SEQ ID NO: 66 | GLDSDEHSTESR | SEQ ID NO: 90 | DSDEHS. |
| SEQ ID NO: 67 | GLDSDEHSTES | SEQ ID NO: 91 | DSDEH |
| SEQ ID NO: 68 | GLDSDEHSTE | SEQ ID NO: 92 | DSDE |
| SEQ ID NO: 69 | GLDSDEHST | SEQ ID NO: 93 | DSD |
| SEQ ID NO: 70 | GLDSDEHS | SEQ ID NO: 94 | SDEHSTESRS |
| SEQ ID NO: 71 | GLDSDEH | SEQ ID NO: 95 | SDEHSTESR |
| SEQ ID NO: 72 | GLDSD | SEQ ID NO: 96 | SDEHSTES |
| SEQ ID NO: 73 | GLDS | SEQ ID NO: 97 | SDEHSTE |
| SEQ ID NO: 74 | GLD | SEQ ID NO: 98 | SDEHST |
| SEQ ID NO: 75 | LDSDEHSTESRS | SEQ ID NO: 99 | SDEHS |
| SEQ ID NO: 76 | LDSDEHSTESR | SEQ ID NO: 100 | SDEH |
| SEQ ID NO: 77 | LDSDEHSTES | SEQ ID NO: 101 | SDE |
| SEQ ID NO: 78 | LDSDEHSTE | SEQ ID NO: 102 | DEHSTESRS |
| SEQ ID NO: 79 | LDSDEHST | SEQ ID NO: 103 | DEHSTESR |
| SEQ ID NO: 80 | LDSDEHS | SEQ ID NO: 3 | DEHSTE |
| SEQ ID NO: 81 | LDSDEH | SEQ ID NO: 106 | DEHST |
| SEQ ID NO: 82 | LDSDE | SEQ ID NO: 107 | DEHS |
| SEQ ID NO: 83 | LDSD | SEQ ID NO: 108 | DEH |
| SEQ ID NO: 84 | LDS | SEQ ID NO: 109 | EHSTESRS |
| SEQ ID NO: 85 | LD | SEQ ID NO: 110 | EHSTESR |
| SEQ ID NO: 86 | DSDEHSTESRS | SEQ ID NO: 111 | EHSTES |
| SEQ ID NO: 87 | DSDEHSTESR | SEQ ID NO: 112 | EHSTE |
| SEQ ID NO: 88 | DSDEHSTE | SEQ ID NO: 113 | EHST |
| SEQ ID NO: 89 | DSDEHST | | EHS |

| | | |
|---|---|---|
| SEQ ID NO: 18 | GLDSDEHSTESRS | |
| SEQ ID NO: 115 | HSTESRS | |
| SEQ ID NO: 116 | HSTESR | |
| SEQ ID NO: 117 | HSTES | |
| SEQ ID NO: 118 | HSTE | |
| SEQ ID NO: 119 | HST | |
| SEQ ID NO: 120 | STESRS | |
| SEQ ID NO: 121 | STESR | |
| SEQ ID NO: 122 | STES | |
| SEQ ID NO: 123 | STE | |
| SEQ ID NO: 124 | TESRS | |
| SEQ ID NO: 125 | TESR | |
| SEQ ID NO: 126 | TES | |
| SEQ ID NO: 127 | ESRS | |
| SEQ ID NO: 128 | ESR | |
| SEQ ID NO: 18 | GLDSDEHSTESRS | |
| SEQ ID NO: 18 | GLDSDEHSTESRS | |
| SEQ ID NO: 18 | GLDSDEHSTESRS | |
| SEQ ID NO: 18 | GLDSDEHSTESRS | |
| SEQ ID NO: 18 | GLDSDEHSTESRS | |
| SEQ ID NO: 18 | GLDSDEHSTESRS | |
| SEQ ID NO: 18 | GLDSDEHSTESRS | |
| SEQ ID NO: 18 | GLDSDEHSTESRS | |

FIG. 7B

JA16 Heavy chain variable region

```
                      CDR1                          CDR2
XVKLQQSGAELVKPGASVKLSCKASGYTFTSFYMYWVKQRPGQGLEWIGEINPSNGDTNFIESFKSKA

CDR3
TLTVDKSSSTAYMQLSSLTSEDSAVYYCTVRFAYWGQGTTVTVSX   (SEQ ID NO:1)
```

FIG. 16

ANTIBODY INHIBITORS OF GDF-8 AND USES THEREOF

This application claims priority to U.S. provisional patent application Ser. No. 60/324,528, filed on Sep. 26, 2001.

FIELD OF THE INVENTION

This invention relates to inhibitors of Growth Differentiation Factor-8 (GDF-8) proteins and methods of use for such inhibitors. More particularly, the invention provides novel antibodies and antibody fragments that are specifically reactive with GDF-8 proteins in vitro and in vivo. The invention is particularly useful for diagnosing, preventing, or treating human or animal disorders in which an increase in muscle tissue would be therapeutically beneficial. Exemplary disorders include neuromuscular disorders (e.g., muscular dystrophy and muscle atrophy), congestive obstructive pulmonary disease, muscle wasting syndrome, sarcopenia, and cachexia; adipose tissue disorders (e.g., obesity); type 2 diabetes; and bone degenerative disease (e.g., osteoporosis).

BACKGROUND OF THE INVENTION

Growth and Differentiation Factor-8 (GDF-8), also known as myostatin, is a member of the Transforming Growth Factor-beta (TGF-β) superfamily of structurally related growth factors, all of which possess physiologically important growth-regulatory and morphogenetic properties (Kingsley et al. (1994) *Genes Dev.*, 8: 133–46; Hoodless et al. (1998) *Curr. Topics Microbiol. Immunol.*, 228: 235–72). GDF-8 is a negative regulator of skeletal muscle mass, and there is considerable interest in identifying factors which regulate its biological activity. For example, GDF-8 is highly expressed in the developing and adult skeletal muscle. The GDF-8 null mutation in transgenic mice is characterized by a marked hypertrophy and hyperplasia of the skeletal muscle (McPherron et al. (1997) *Nature*, 387: 83–90). Similar increases in skeletal muscle mass are evident in naturally occurring mutations of GDF-8 in cattle (Ashmore et al. (1974) *Growth*, 38: 501–507; Swatland and Kieffer (1994) *J. Anim. Sci.*, 38: 752–757; McPherron and Lee (1997) *Proc. Natl. Acad. Sci. USA*, 94: 12457–12461; and Kambadur et al. (1997) *Genome Res.*, 7: 910–915). Since GDF-8 is expressed in both developing and adult muscles, it is not clear whether it regulates muscle mass during development or in adults. Thus, the question of whether or not GDF-8 regulates muscle mass in adults is important from a scientific and therapeutic perspective. Recent studies have also shown that muscle wasting associated with HIV-infection in humans is accompanied by increases in GDF-8 protein expression (Gonzalez-Cadavid et al. (1998) *PNAS*, 95: 14938–43). In addition, GDF-8 can modulate the production of muscle-specific enzymes (e.g., creatine kinase) and modulate myoblast cell proliferation (WO 00/43781).

A number of human and animal disorders are associated with loss or functional impairment of muscle tissue, including muscular dystrophy, muscle atrophy, congestive obstructive pulmonary disease, muscle wasting syndrome, sarcopenia, and cachexia. To date, very few reliable or effective therapies exist for these disorders. However, the terrible symptoms associated with these disorders may be substantially reduced by employing therapies that increase the amount of muscle tissue in patients suffering from the disorders. While not curing the conditions, such therapies would significantly improve the quality of life for these patients and could ameliorate some of the effects of these diseases. Thus, there is a need in the art to identify new therapies that may contribute to an overall increase in muscle tissue in patients suffering from these disorders.

In addition to its growth-regulatory and morphogenetic properties in skeletal muscle, GDF-8 may also be involved in a number of other physiological processes, including glucose homeostasis in the development of type 2 diabetes and adipose tissue disorders, such as obesity. For example, GDF-8 modulates preadipocyte differentiation to adipocytes (Kim et al. (2001) *BBRC*, 281: 902–906).

There are also a number of conditions associated with a loss of bone, including osteoporosis, especially in the elderly and/or postmenopausal women. Currently available therapies for these conditions work by inhibiting bone resorption. A therapy that promotes new bone formation would be a desirable alternative to or addition to, these therapies.

Like TGF-β-1, -2, and -3, the GDF-8 protein is synthesized as a precursor protein consisting of an amino-terminal propeptide and a carboxy-terminal mature domain (McPherron and Lee, (1997) *Proc. Natl. Acad. Sci. USA*, 94: 12457–12461). Before cleavage, the precursor GDF-8 protein forms a homodimer. The amino-terminal propeptide is then cleaved from the mature domain. The cleaved propeptide may remain noncovalently bound to the mature domain dimer, inactivating its biological activity (Miyazono et al. (1988) *J. Biol. Chem.*, 263: 6407–6415; Wakefield et al. (1988) *J. Biol. Chem.*, 263; 7646–7654; and Brown et al. (1990) *Growth Factors*, 3: 35–43). It is believed that two GDF-8 propeptides bind to the GDF-8 mature dimer (Thies et al. (2001) *Growth Factors*, 18: 251–259). Due to this inactivating property, the propeptide is known as the "latency-associated peptide" (LAP), and the complex of mature domain and propeptide is commonly referred to as the "small latent complex" (Gentry and Nash (1990) *Biochemistry*, 29: 6851–6857; Derynck et al. (1995) *Nature*, 316: 701–705; and Massague (1990) *Ann. Rev. Cell Biol.*, 12: 597–641). Other proteins are also known to bind to GDF-8 or structurally related proteins and inhibit their biological activity. Such inhibitory proteins include follistatin, and potentially, follistatin-related proteins (Gamer et al. (1999) *Dev. Biol.*, 208: 222–232). The mature domain is believed to be active as a homodimer when the propeptide is removed.

GDF-8 is highly conserved in sequence and in function across species. The amino acid sequence of murine and human GDF-8 is identical, as is the pattern of mRNA expression (McPherron et al. (1997) *Nature* 387: 83–90; Gonzalez-Cadavid et al. (1998) *Proc. Natl. Acad. Sci. USA* 95: 14938–14943). This conservation of sequence and function suggests that inhibition of GDF-8 in humans is likely to have a similar effect to inhibition of GDF-8 in mice.

GDF-8 is involved in the regulation of many critical biological processes. Due to its key function in these processes, GDF-8 may be a desirable target for therapeutic intervention. In particular, therapeutic agents that inhibit the activity of GDF-8 may be used to treat human or animal disorders in which an increase in muscle tissue would be therapeutically beneficial, particularly muscle and adipose tissue disorders, bone degenerative diseases, neuromuscular disorders, and diabetes, as discussed above.

SUMMARY OF THE INVENTION

The present invention provides novel protein inhibitors comprising antibodies and antibody fragments that are specifically reactive with a mature GDF-8 protein, whether it is in a monomeric form, active dimeric form, or complexed in the GDF-8 latent complex. In an embodiment of the invention, the antibodies bind to an epitope on the mature GDF-8 protein, which results in a reduction in one or more of the biological activities associated with GDF-8, relative to a mature GDF-8 protein that is not bound by the same antibody. In an embodiment of the invention, the presently disclosed antibodies reduce GDF-8 activity associated with negative regulation of skeletal muscle mass and/or bone density.

The presently disclosed antibodies possess unique and unexpected biological properties. For instance, one of skill in the art would typically expect good neutralizing antibodies to strongly bind to the active GDF-8 protein in vitro, forming a stable inhibitory complex with the protein. A neutralizing antibody also called an inhibitory antibody, having a high affinity for a particular protein will typically be expected to provide higher levels of neutralization relative to a lower affinity antibody to the same protein. However, quite unexpectedly, the present inventors have discovered antibodies that only weakly bind to and neutralize active GDF-8 protein in vitro, yet are effective in vivo. The discovery of such antibodies led, in turn, to the identification of a specific site on GDF-8 to which the antibodies bind. It is therefore expected that any antibody specifically binding to the identified site would similarly possess in vivo neutralizing properties.

Additionally, the presently disclosed antibodies possess unique and unexpected properties. For example, the antibodies not only recognize mature GDF-8 protein in its monomeric and dimeric forms, but also recognize the intact GDF-8 latent complex.

The presently disclosed antibodies may be administered in a therapeutically effective dose to treat or prevent medical conditions in which an increase in muscle tissue mass or bone density would be therapeutically beneficial. Diseases and disorders that may be treated by these GDF-8 antibodies include muscle or neuromuscular disorders such as muscular dystrophy, muscle atrophy, congestive obstructive pulmonary disease, muscle wasting syndrome, sarcopenia, and cachexia; adipose tissue disorders such as obesity; metabolic disorders such as type 2 diabetes, impaired glucose tolerance, metabolic syndromes (e.g., syndrome X), insulin resistance induced by trauma (e.g., burns); and bone degenerative disease such as osteoporosis, especially in the elderly and/or postmenopausal women. Additional metabolic bone diseases and disorders amenable to treatment with these GDF-8 antibodies include low bone mass due to chronic glucocorticoid therapy, premature gonadal failure, androgen suppression, vitamin D deficiency, secondary hyperparathyroidism, nutritional deficiencies, and anorexia nervosa.

In addition, the presently disclosed antibodies may be used as a diagnostic tool to quantitatively or qualitatively detect mature GDF-8 protein or fragments thereof, regardless of whether it is in a monomeric form, dimeric active form, or complexed in the GDF-8 latent complex. For example, the antibodies may be used to detect quantitatively or qualitatively mature GDF-8 protein in a cell, bodily fluid, tissue, or an organ. The presence or amount of mature GDF-8 protein detected is then correlated with one or more of the medical conditions listed above.

The presently disclosed antibodies may be provided in a diagnostic kit. The kit may contain other components that aid the detection of mature GDF-8 protein, and help correlate the results with one or more of the medical conditions described above.

Brief Description of the Sequences

| SEQ ID NO. | FIG. (if applicable) | Description |
| --- | --- | --- |
| 1 | FIG. 16 | JA-16 heavy chain variable region AA sequence |
| 2, 3, 5, 8 | | Antibody binding sites in protein |
| 4 | | DNA sequence for GDF-8 (accession no. xm_030768) |
| 6 | | Nucleic acid sequence encoding SEQ ID NO: 1 |
| 7 | | DNA sequence for BMP-11 (accession no. xm_049170) |
| 9 | | B1 peptide, derived from BMP-11 |
| 10 | | G1 peptide, derived from GDF-8 |
| 11–13, 65, 105, 114, 129 | FIG. 1 | Synthetic peptides derived from SEQ ID NO:14 |
| 14 | | A cysteine-to-serine mutated sequence of mature GDF-8. |
| 15 | FIG. 3 | mature GDF-8 AA sequence |
| 16 | FIG. 3 | BMP-11 AA sequence |
| 18 | | JA-16 eptitope region from GDF-8 |
| 17–64 | FIG. 6A | Overlapping 13-mer peptides corresponding to portions of the GDF-8 sequence |
| 65 | | Biotinylated N-terminal peptide derived from GDF-8 |
| 66–104, 106–113, 115–128 | | Mutated versions of SEQ ID NO:18 |
| 130 | | AA sequence of GDF-8 propeptide (accession no. xp_030768) |
| 131 | | AA sequence of BMP-11 propeptide (accession no. xp_049170) |

BRIEF DESCRIPTION OF THE FIGURES

FIG. 3 indicates the differences in the amino acid sequences of mature GDF-8 (SEQ ID NO:15) and BMP-11 (SEQ ID NO:16).

FIGS. 6A and B show the mapping studies of JA-16 binding using overlapping 13-mer synthetic peptide sequences from GDF-8.

FIG. 16 shows the amino acid sequence of the JA-16 heavy chain variable region (SEQ ID NO:1). The complimentarity determining regions (CDRs) are underlined. The corresponding nucleic acid sequence is provided in SEQ ID NO:6.

DEFINITIONS

Figure 1:
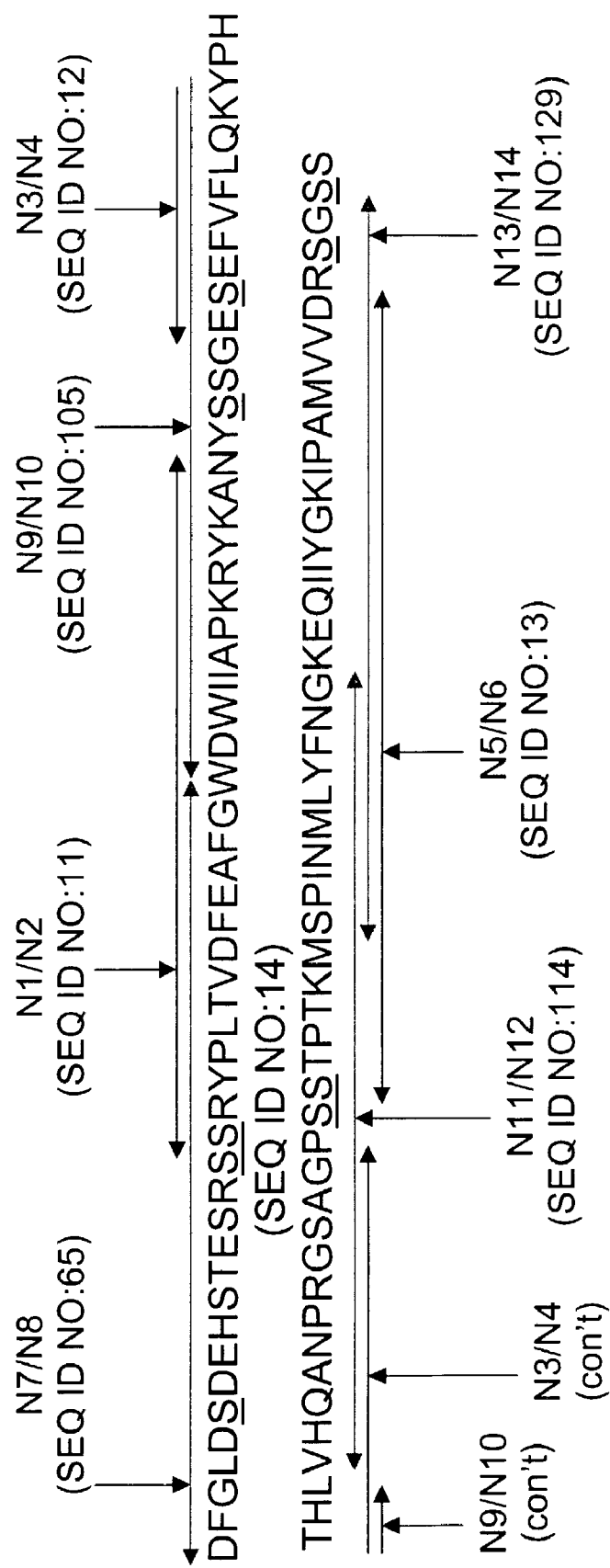
FIG. 1 shows the GDF-8 synthetic peptides (SEQ ID NOS: 11–13, 65, 105, 114, and 129, all derived from SEQ ID NO:14) used to characterize the binding specificity of JA-16. The underlined amino acids indicate positions where native cysteines have been replaced with serines.

The term "antibody" refers to one or more polyclonal antibodies, monoclonal antibodies, antibody compositions, antibodies having mono- or poly-specificity, humanized antibodies, single-chain antibodies, chimeric antibodies, CDR-grafted antibodies, antibody fragments such as Fab, F(ab')$_2$, Fv, and other antibody fragments which retain the antigen binding function of the parent antibody.

The term "chimeric antibodies" refers to molecules in which a portion of the heavy and/or light chain is identical or homologous to corresponding sequences from a particular species (or belonging to a particular antibody class or subclass), while the remainder of the chain(s) is identical or homologous to corresponding sequences derived from a different species (or belonging to a different antibody class or subclass). Such chimeric antibodies are described by Morrison, et al. (1984) *Proc. Natl. Acad. Sci USA* 81: 6851–6855.

The term "epitope" refers to a molecule or portion of a molecule that is capable of specifically reacting with an anti-GDF-8 monoclonal antibody. Epitopes may comprise proteins, protein fragments, peptides, carbohydrates, lipids, or other molecules, but are most commonly proteins, short oligopeptides, or combinations thereof.

The terms "GDF polypeptide" and "GDF protein" refer generally to any growth and differentiation factors that are structurally or functionally related to GDF-8.

The term "GDF inhibitor" includes any agent capable of inhibiting activity, expression, processing, or secretion of a GDF protein. Such inhibitors include proteins, antibodies, peptides, peptidomimetics, ribozymes, anti-sense oligonucleotides, double-stranded RNA, and other small molecules which specifically inhibit the GDF proteins.

The terms "GDF-8" or "GDF-8 protein" refer to a specific growth and differentiation factor. The terms include the full length unprocessed precursor form of the protein, as well as the mature and propeptide forms resulting from post-translational cleavage. The terms also refer to any fragments of GDF-8 that maintain the known biological activities associated with the protein, as discussed herein, including sequences that have been modified with conservative or non-conservative changes to the amino acid sequence.

These GDF-8 molecules may be derived from any source, natural or synthetic. The human form of mature GDF-8 protein is provided in SEQ ID NO:15. However, the present invention also encompasses GDF-8 molecules from all other sources, including GDF-8 from bovine, chicken, murine, rat, porcine, ovine, turkey, baboon, and fish. These various GDF-8 molecules have been described in McPherron et al. (1997) *Proc. Natl. Acad. Sci. USA*, 94: 12457–12461.

"Mature GDF-8" refers to the protein that is cleaved from the carboxy-terminal domain of the GDF-8 precursor protein. The mature GDF-8 may be present as a monomer, homodimer, or in a GDF-8 latent complex. Depending on the in vivo or in vitro conditions, an equilibrium between any or all of these different forms may exist. GDF-8 is believed to be biologically active as homodimer. In its biologically active form, the mature GDF-8 is also referred to as "active GDF-8."

"GDF-8 propeptide" refers to the polypeptide that is cleaved from the amino-terminal domain of the GDF-8 precursor protein. The GDF-8 propeptide is capable of binding to the propeptide binding domain on the mature GDF-8.

"GDF-8 latent complex" refers to the complex of proteins formed between the mature GDF-8 homodimer and the GDF-8 propeptide. It is believed that two GDF-8 propeptides associate with a GDF-8 homodimer to form an inactive tetrameric complex. The latent complex may include other GDF-8 inhibitors in place of or in addition to one or more of the GDF-8 propeptides.

The phrase "GDF-8 inhibitor" includes any agent capable of inhibiting the activity, expression, processing, or secretion of GDF-8 protein. Such inhibitors include proteins, antibodies, peptides, peptidomimetics, ribozymes, antisense oligonucleotides, double-stranded RNA, and other small molecules that specifically inhibit the activity of GDF-8 protein. Such inhibitors are said to "neutralize" or "reduce" the biological activity of GDF-8 protein.

The phrase "GDF-8 activity" refers to one or more of growth-regulatory or morphogenetic activities associated with active GDF-8 protein. For example, active GDF-8 is a negative regulator of skeletal muscle. Active GDF-8 can also modulate the production of muscle-specific enzymes (e.g., creatine kinase), stimulate myoblast cell proliferation, and modulate preadipocyte differentiation to adipocytes.

The terms "isolated" or "purified" refer to a molecule that is substantially free of its natural environment. For instance, an isolated protein is substantially free of cellular material or other contaminating proteins from the cell or tissue source from which it is derived. The phrase "substantially free of cellular material" refers to preparations where the isolated protein is at least 70% to 80% (w/w) pure, optionally at least 80%–89% (w/w) pure, optionally 90–95% pure; and optionally at least 96%, 97%, 98%, 99% or 100% (w/w) pure.

"Mammal" for purposes of treatment refers to any animal classified as a mammal, including humans, domestic and farm animals, and zoo, sports, or pet animals, such as dogs, horses, cats, sheep, pigs, cows, etc. The mammal is human in one embodiment of the invention.

The term "monoclonal antibody" refers to one or more antibodies from a substantially homogeneous antibody population that is directed against a single antigenic epitope. The term encompasses humanized antibodies, single-chain antibodies, chimeric antibodies, CDR-grafted antibodies, antibody fragments such as Fab, F(ab')$_2$, Fv, and other antibody fragments which retain the antigen binding function of the parent antibody.

Furthermore, the term "monoclonal antibody" is not limited to any particular species or source of the antibody, or the manner by which it is made. Monoclonal antibodies may be made via traditional hybridoma techniques (Kohler and Milstein (1975) *Nature*, 256: 495–499), recombinant DNA methods (U.S. Pat. No. 4,816,567), or phage antibody libraries (Clackson et al. (1991) *Nature*, 352: 624–628; Marks et al. (1991) *J. Mol. Biol.*, 222: 581–597). Monoclonal antibodies of any mammalian or non-mammalian species can be used in this invention. For example, the antibodies may be derived from primates (e.g., human, orangutan, etc.), avian (e.g., chicken, turkey, etc.), bovine, murine, rat, porcine, ovine, or fish. In one embodiment of the invention, the antibodies are of rat, murine, or human origin.

The terms "neutralize" and "neutralizing" refer to a reduction in the activity of GDF-8 by a GDF-8 inhibitor, relative to the activity of a GDF-8 molecule that is not bound by the same inhibitor. Thus, a "neutralizing" antibody reduces the activity of GDF-8 relative to the activity of a GDF-8 molecule not bound by the same antibody. The activity of the GDF-8 protein, when bound by one or more of the presently disclosed GDF-8 inhibitors (e.g., the presently disclosed antibodies), is reduced at least about 10%, 15%, 20%, 25%, 30%, 35%, 40%, 45%, 50%, or 55%, optionally at least about 60%, 62%, 64%, 66%, 68%, 70%, 72%, 72%, 76%, 78%, 80%, 82%, 84%, 86%, or 88%, optionally at least about 90%, 91%, 92%, 93%, or 94%, and optionally at least 95% to 100% relative to a GDF-8 protein that is not bound by one or more of the presently disclosed GDF-8 inhibitors.

The term "specific interaction," or "specifically binds," or the like, means that two molecules form a complex that is relatively stable under physiologic conditions. The term is also applicable where, e.g., an antigen-binding domain is specific for a particular epitope, which is carried by a number of antigens, in which case the specific binding member carrying the antigen-binding domain will be able to bind to the various antigens carrying the epitope. Specific binding is characterized by a high affinity and a low to moderate capacity. Nonspecific binding usually has a low affinity with a moderate to high capacity. Typically, the binding is considered specific when the affinity constant $K_a$ is higher than $10^6$ $M^{-1}$, or can be higher than $10^8$ $M^{-1}$. If necessary, non-specific binding can be reduced without substantially affecting specific binding by varying the binding conditions. Such conditions are known in the art, and a skilled artisan using routine techniques can select appropriate conditions. The conditions are usually defined in terms of concentration of antibodies, ionic strength of the solution, temperature, time allowed for binding, concentration of non-related molecules (e.g., serum albumin, milk casein), etc. Exemplary conditions are set forth in Example 4.

The term "TGF-β superfamily" refers to a family of structurally related growth factors, all of which are endowed with physiologically important growth-regulatory and morphogenetic properties. This family of related growth factors is well known in the art (Kingsley et al. (1994) *Genes Dev.*, 8: 133–146; Hoodless et al. (1998) *Curr. Topics Microbiol. Immunol.*, 228: 235–272). The TGF-β superfamily includes Bone Morphogenetic Proteins (BMPs), Activins, Inhibins, Mullerian Inhibiting Substance, Glial-Derived Neurotrophic Factor, and a still growing number of Growth and Differentiation Factors (GDFs), such as GDF-8 (myostatin). Many of these proteins are related in structure to GDF-8, such as BMP-11; and/or activity, such as activin.

The term "treatment" refers to both therapeutic treatment and prophylactic or preventative measures. Those in need of treatment may include individuals already having a particular medical disorder as well as those who may ultimately acquire the disorder (i.e., those needing preventative measures).

DETAILED DESCRIPTION OF THE INVENTION

Antibodies

Intact antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (V$_H$) followed by a number of constant domains. Each light chain has a variable domain at one end (V$_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains (Clothia et al. (1985) *J. Mol. Biol.*, 186: 651–663; Novotny and Haber (1985) *Proc. Natl. Acad. Sci. USA*, 82: 4592–4596).

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgA1 and IgA2 for IgA; IgG1, IgG2, IgG3, IgG4 for IgG in humans, and IgG1, IgG2a, IgG2b, and IgG3 for IgG in mouse. The heavy-chain constant domains that correspond to the major classes of immunoglobulins are called α, δ, ε, γ, and μ, respectively. The subunit structures and three-dimensional configurations of different classes of immunoglobulins are well known in the art.

For a review of the antibody structure, see Antibodies: A Laboratory Manual, Cold Spring Harbor Laboratory, eds. Harlow et al., 1988. Briefly, each light chain is composed of an N-terminal variable (V) domain (V$_L$) and a constant (C) domain (C$_L$). Each heavy chain is composed of an N-terminal V domain, three or four C domains, and a hinge region. The C$_H$ domain most proximal to V$_H$ is designated as C$_H$1. The V$_H$ and V$_L$ domain consist of four regions of relatively conserved sequence called framework regions (FR1, FR2, FR3, and FR4), which form a scaffold for three regions of hypervariable sequence (complementarity determining regions, CDRs). The CDRs contain most of the residues responsible for specific interactions with the antigen. CDRs are referred to as CDR1, CDR2, and CDR3. Accordingly, CDR constituents on the on the heavy chain are referred to as H1, H2, and H3, while CDR constituents on the light chain are referred to as L1, L2, and L3. CDR3 is the greatest source of molecular diversity within the antibody-binding site. H3, for example, can be as short as two amino acid residues or greater than 26. The locations of immunoglobulin variable domains in a given antibody may be determined as described, for example, in Sequences of Proteins of Immunological Interest, US Department of Health and Human Services, eds. Kabat et al., 1991.

Antibody diversity is created by the use of multiple germline genes encoding variable regions and a variety of somatic events. The somatic events include recombination of variable gene segments with diversity (D) and joining (J) gene segments to make a complete V$_H$ region and the recombination of variable and joining gene segments to make a complete V$_L$ region. The recombination process itself is imprecise, resulting in the loss or addition of amino acids at the V(D)J junctions. These mechanisms of diversity occur in the developing B cell prior to antigen exposure. After antigenic stimulation, the expressed antibody genes in B cells undergo somatic mutation. Based on the estimated number of germline gene segments, the random recombination of these segments, and random V$_H$-V$_L$ pairing, up to $1.6 \times 10^7$ different antibodies could be produced (Fundamental Immunology, 3rd ed., ed. Paul, Raven Press, New York, N.Y., 1993). When other processes which contribute to antibody diversity (such as somatic mutation) are taken into account, it is thought that upwards of $1 \times 10^{10}$ different antibodies could be generated (Immunoglobulin Genes, 2nd ed., eds. Jonio et al., Academic Press, San Diego, Calif., 1995). Because of the many processes involved in generating antibody diversity, it is unlikely that independently derived monoclonal antibodies with the same antigen specificity will have identical amino acid sequences.

Antibodies may be raised against any portion of a protein which provides an antigenic epitope. In one embodiment of the invention, the presently disclosed antibodies specifically bind to an epitope on a protein belonging to the superfamily of TGF-β proteins. The protein is optionally a Bone Morphogenetic Proteins (BMP), Activin, Inhibin, Mullerian Inhibiting Substance, Glial-Derived Neurotrophic Factor, or Growth and Differentiation Factors (GDFs). Optionally, the protein is BMP-11, Activin, or GDF-8. The protein is optionally a mature GDF-8 protein.

In an embodiment, the presently disclosed antibodies bind to a mature GDF-8 protein as set forth in SEQ ID NO:15; optionally between amino acid 1 and amino acid 50; optionally between amino acid 1 and amino acid 25; and optionally between amino acid 1 and 15 of SEQ ID NO:15.

In another embodiment, the presently disclosed antibodies specifically bind to the sequence Asp-Glu-His-Xaa-Thr (SEQ ID NO:2) in any one of the proteins belonging to the TGF-β superfamily, where Xaa is Ala, Gly, His, Met, Asn, Arg, Ser, Thr, or Trp. Optionally, the antibodies specifically bind to the peptide sequence Asp-Glu-His-Xaa-Thr (SEQ ID NO:2) in GDF-8, where Xaa is Ala, Gly, His, Met, Asn, Arg, Ser, Thr, or Trp. Optionally, the antibodies specifically bind to Asp-Glu-His-Ser-Thr (SEQ ID NO:3) in the mature GDF-8 protein (SEQ ID NO:15).

Optionally, the presently disclosed antibodies specifically bind to the peptide sequence Asp-Phe-Gly-Leu-Asp-Cys-Asp-Glu-His-Xaa-Thr-Glu-Ser-Arg-Cys (SEQ ID NO:5) in any one of the proteins belonging to the TGF-β superfamily, where Xaa is Ala, Gly, His, Met, Asn, Arg, Ser, Thr, or Trp. Optionally, the antibodies specifically bind to the peptide sequence Asp-Phe-Gly-Leu-Asp-Cys-Asp-Glu-H is-Xaa-Th r-Glu-Ser-Arg-Cys (SEQ ID NO:5) in GDF-8, where Xaa is Ala, Gly, His, Met, Asn, Arg, Ser, Thr, or Trp. Optionally, the antibodies specifically bind to the peptide sequence Asp-Phe-Gly-Leu-Asp-Cys-Asp-Glu-H is-Ser-Thr-Glu-Ser-Arg-Cys (SEQ ID NO:8) in the mature GDF-8 protein (SEQ ID NO:15).

The GDF-8 protein to which the presently disclosed antibodies may specifically bind is optionally at least about 75%–80% identical to SEQ ID NO:15, optionally at least about 81% to about 85% identical to SEQ ID NO:15, optionally at least about 86%, 87%, 88%, 89%, 90%, 91%, 92%, 93%, or 94% identical to SEQ ID NO:15, and optionally at least about 95%, 96%, 97%, 98%, 99% or 100% identical to SEQ ID NO:15. The GDF-8 protein optionally comprises SEQ ID NO:15.

In an alternative embodiment, the presently disclosed antibodies may specifically bind to the BMP-11 protein. The BMP-11 protein is optionally at least about 75%–80% identical to SEQ ID NO:16, optionally at least about 81% to about 85% identical to SEQ ID NO:16, optionally at least about 86%, 87%, 88%, 89%, 90%, 91%, 92%, 93%, or 94% identical to SEQ ID NO:16, and optionally at least about 95%, 96%, 97%, 98%, 99% or 100% identical to SEQ ID NO:16. The BMP-11 protein optionally comprises SEQ ID NO:16.

In a particular embodiment, termed JA-16, the antibody comprises the amino acid sequence of SEQ ID NO:1 as a part of the variable region of the heavy chain. In other embodiments, the antibody comprises at least one single chain CDR chosen from the amino acids 30–35 of SEQ ID NO:1, amino acids 50–66 of SEQ ID NO:1, and amino acids 99–102 of SEQ ID NO:1.

One of skill in the art will recognize that the antibodies of the invention may contain any number of conservative or non-conservative changes to their respective amino acid sequences without altering their biological properties. Changes can be made in either the framework (FR) or in the CDR regions. While changes in the framework regions are usually designed to improve stability and immunogenicity of the antibody, changes in the CDRs are usually designed to increase affinity of the antibody for its target. Such affinity-increasing changes are typically determined empirically by altering the CDR region and testing the antibody. Such alterations can be made according to the methods described in Antibody Engineering, 2nd. ed., Oxford University Press, ed. Borrebaeck, 1995. Conservative amino acid modifications are based on the relative similarity of the amino acid side-chain substituents, for example, their hydrophobicity, hydrophilicity, charge, size, and the like. Exemplary conservative substitutions which take various of the foregoing characteristics into consideration are well known to those of skill in the art and include: arginine and lysine; glutamate and aspartate; serine and threonine; glutamine and asparagine; and valine, leucine, and isoleucine. Further details on such changes are described in the following sections. Unlike in CDRs, more substantial non-conservative changes in structure framework regions (FRs) can be made without adversely affecting the binding properties of an antibody. Changes to FRs include, but are not limited to, humanizing a non-human derived framework or engineering certain framework residues that are important for antigen contact or for stabilizing the binding site, e.g., changing the class or subclass of the constant region, changing specific amino acid residues which might alter an effector function such as Fc receptor binding (Lund et al. (1991) J. Immun. 147: 2657–2662 and Morgan et al. (1995) Immunology 86: 319–324), or changing the species from which the constant region is derived as described below.

In an embodiment, the presently disclosed antibodies specifically bind to mature GDF-8 protein, regardless of whether it is in monomeric form, active dimer form, or complexed in a GDF-8 latent complex, with an affinity of between about $10^6$ and about $10^{11}$ $M^{-1}$, optionally between about $10^8$ and about $10^{11}$ $M^{-1}$.

The antibodies of the present invention may comprise polyclonal antibodies, monoclonal antibodies, antibody compositions, antibodies having mono- or poly-specificity, humanized antibodies, single-chain antibodies, CDR-grafted antibodies, antibody fragments such as Fab, F(ab')$_2$, Fv, and other antibody fragments which retain the antigen binding function of the parent antibody. The presently disclosed antibodies may also be modified to chimeric antibodies. For instance, a human Fc region can be fused to a GDF-8 binding region from a murine antibody to generate a chimeric antibody. By replacing other portions of the murine antibody (outside of the antigen binding region) with corresponding human antibody fragments, a humanized antibody may be produced. Such chimeric or humanized antibodies may display enhanced biological specificity or in vivo stability. They are particularly useful in designing antibodies for human therapies. It is understood that practitioners are familiar with the standard resource materials which describe specific conditions and procedures for the construction, manipulation, production, and isolation of antibodies (see, for example, Harlow and Lane (1988) *Antibodies: A Laboratory Manual*, Cold Spring Harbor Press, Cold Spring Harbor, N.Y.).

The present invention also provides cells, such as hybridomas, that produce any of the presently disclosed antibodies. One of skill in the art is familiar with the many cells that are suitable for producing antibodies. Any cell compatible with the present invention may be used to produce the presently disclosed antibodies. In an embodiment, the presently disclosed antibodies are produced by a hybridoma cell. A hybridoma cell line, which produces murine anti-GDF-8 JA-16 antibody has been deposited with American Tissue Culture Collection (Deposit Designation Number PTA-4236) on Apr. 18, 2002. The address of the depository is 10801 University Blvd, Manassas, Va. 20110.

Methods of Treating Disease

The antibodies of the present invention are useful to prevent, diagnose, or treat various medical disorders in humans or animals. The antibodies are used to inhibit or reduce one or more activities associated with the GDF protein, relative to a GDF protein not bound by the same antibody. Optionally, the antibodies inhibit or reduce one or more of the activities of mature GDF-8 (regardless of whether in monomeric form, active dimeric form, or complexed in a GDF-8 latent complex) relative to a mature GDF-8 protein that is not bound by the same antibodies. In an embodiment, the activity of the mature GDF-8 protein, when bound by one or more of the presently disclosed antibodies, is inhibited at least 50%, optionally at least 60, 62, 64, 66, 68, 70, 72, 72, 76, 78, 80, 82, 84, 86, or 88%, optionally at least 90, 91, 92, 93, or 94%, and optionally at least 95% to 100% relative to a mature GDF-8 protein that is not bound by one or more of the presently disclosed antibodies.

The medical disorder being diagnosed, treated, or prevented by the presently disclosed antibodies is optionally a muscle and neuromuscular disorder; an adipose tissue disorder such as obesity; type 2 diabetes, impaired glucose tolerance, metabolic syndromes (e.g., syndrome X), insulin resistance induced by trauma such as burns; or bone degenerative disease such as osteoporosis. The medical condition is optionally a muscle or neuromuscular disorder, such as muscular dystrophy, muscle atrophy, congestive obstructive pulmonary disease, muscle wasting syndrome, sarcopenia, or cachexia and disorders associated with a loss of bone, which include osteoporosis, especially in the elderly and/or postmenopausal women, glucocorticoid-induced osteoporosis, osteopenia, and osteoporosis-related fractures. Other target metabolic bone diseases and disorders amendable to treatment with GDF-8 antibodies of the invention include low bone mass due to chronic glucocorticoid therapy, premature gonadal failure, androgen suppression, vitamin D deficiency, secondary hyperparathyroidism, nutritional deficiencies, and anorexia nervosa. The antibodies are optionally used to prevent, diagnose, or treat such medical disorders in mammals, optionally in humans.

The antibodies or antibody compositions of the present invention are administered in therapeutically effective amounts. As used herein, an "effective amount" of the antibody is a dosage which is sufficient to reduce the activity of GDF proteins to achieve a desired biological outcome (e.g., increasing muscle mass or strength). Generally, a therapeutically effective amount may vary with the subject's age, condition, and sex, as well as the severity of the medical condition in the subject. The dosage may be determined by an physcian and adjusted, as necessary, to suit observed effects of the treatment. Generally, the compositions are administered so that antibodies are given at a dose between 1 µg/kg and 20 mg/kg. Optionally, the antibodies are given as a bolus dose, to maximize the circulating levels of antibodies for the greatest length of time after the dose. Continuous infusion may also be used after the bolus dose.

The methods of treating, diagnosing, or preventing the above medical conditions with the presently disclosed antibodies can also be used on other proteins in the TGF-β superfamily. Many of these proteins, e.g., BMP-11, are related in structure to GDF-8. Accordingly, in another embodiment, the invention provides methods of treating the aforementioned disorders by administering to a subject an antibody capable of inhibiting BMP-11 or activin, either alone or in combination with other TGF-β inhibitors, such as a neutralizing antibody against GDF-8.

The antibodies of the present invention may be used to detect the presence of proteins belonging to the TGF-β superfamily, such as BMP-11 and GDF-8. By correlating the presence or level of these proteins with a medical condition, one of skill in the art can diagnose the associated medical condition. The medical conditions that may be diagnosed by the presently disclosed antibodies are set forth above.

Such detection methods are well known in the art and include ELISA, radioimmunoassay, immunoblot, western blot, immunofluorescence, immuno-precipitation, and other comparable techniques. The antibodies may further be provided in a diagnostic kit that incorporates one or more of these techniques to detect a protein (e.g., GDF-8). Such a kit may contain other components, packaging, instructions, or other material to aid the detection of the protein and use of the kit.

Where the antibodies are intended for diagnostic purposes, it may be desirable to modify them, for example with a ligand group (such as biotin) or a detectable marker group (such as a fluorescent group, a radioisotope or an enzyme). If desired, the antibodies (whether polyclonal or monoclonal) may be labeled using conventional techniques. Suitable labels include fluorophores, chromophores, radioactive atoms, electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. Other suitable labels include, for example, one of the binding partners such as biotin and avidin or streptavidin, IgG and protein A, and various receptor-ligand couples known in the art. Other permutations and possibilities will be readily apparent to those of ordinary skill in the art, and are considered as equivalents within the scope of the instant invention.

Antibody Compositions

The present invention provides compositions comprising the presently disclosed antibodies. Such compositions may be suitable for pharmaceutical use and administration to patients. The compositions typically comprise one or more antibodies of the present invention and a pharmaceutically acceptable excipient. As used herein, the phrase "pharmaceutically acceptable excipient" includes any and all solvents, dispersion media, coatings, antibacterial and antifungal agents, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions. The pharmaceutical compositions may also be included in a container, pack, or dispenser together with instructions for administration.

A pharmaceutical composition of the invention is formulated to be compatible with its intended route of administration. Methods to accomplish the administration are known to those of ordinary skill in the art. It may also be possible to obtain compositions which may be topically or orally administered, or which may be capable of transmission across mucous membranes The administration may, for example, be intravenous, intraperitoneal, intramuscular, intracavity, subcutaneous or transdermal.

Solutions or suspensions used for intradermal or subcutaneous application typically include one or more of the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. The pH can be adjusted with acids or bases, such as hydrochloric acid or sodium hydroxide. Such preparations may be enclosed in ampoules, disposable syringes or multiple dose vials made of glass or plastic.

Pharmaceutical compositions suitable for injection include sterile aqueous solutions or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents, for example, sugars, polyalcohols such as manitol, sorbitol, sodium chloride will be included in the composition. Prolonged absorption of the injectable compositions can be brought about by including in the composition an agent which delays absorption, for example, aluminum monostearate and gelatin.

Oral compositions generally include an inert diluent or an edible carrier. They can be enclosed in gelatin capsules or compressed into tablets. For the purpose of oral therapeutic administration, the antibodies can be incorporated with excipients and used in the form of tablets, troches, or capsules. Pharmaceutically compatible binding agents, and/or adjuvant materials can be included as part of the composition. The tablets, pills, capsules, troches, and the like can contain any of the following ingredients, or compounds of a similar nature; a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the antibodies are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The antibodies may also be prepared in the form of suppositories (e.g., with conventional suppository bases such as cocoa butter and other glycerides) or retention enemas for rectal delivery.

In one embodiment, the presently disclosed antibodies are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions containing the presently disclosed antibodies can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Antibodies which exhibit large therapeutic indices are an embodiment of the invention.

The data obtained from the cell culture assays and animal studies can be used in formulating a range of dosage for use in humans. The dosage of such compounds lies optionally within a range of circulating concentrations that include the $ED_{50}$ with little or no toxicity. The dosage may vary within this range depending upon the dosage form employed and the route of administration utilized. For any antibody used in the present invention, the therapeutically effective dose can be estimated initially from cell culture assays. A dose may be formulated in animal models to achieve a circulating plasma concentration range that includes the $IC_{50}$ (i.e., the concentration of the test antibody which achieves a half-maximal inhibition of symptoms) as determined in cell culture. Levels in plasma may be measured, for example, by high performance liquid chromatography. The effects of any particular dosage can be monitored by a suitable bioassay. Examples of suitable bioassays include DNA replication assays, transcription-based assays, GDF protein/receptor binding assays, creatine kinase assays, assays based on the differentiation of pre-adipocytes, assays based on glucose uptake in adipocytes, and immunological assays.

Modified Antibodies

It is understood by one of ordinary skill in the art that certain amino acids may be substituted for other amino acids in a protein structure without adversely affecting the activity of the protein, e.g., binding characteristics of an antibody. It is thus contemplated by the inventors that various changes may be made in the amino acid sequences of the presently disclosed antibodies, or DNA sequences encoding the antibodies, without appreciable loss of their biological utility or activity. Such changes may include deletions, insertions, truncations, substitutions, fusions, shuffling of motif sequences, and the like.

In making such changes, the hydropathic index of amino acids may be considered. The importance of the hydropathic amino acid index in conferring interactive biological function on a protein is generally understood in the art (Kyte and Doolittle (1982) *J. Mol. Biol.*, 157: 105–132). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, 1982); these are isoleucine (+4.5), valine (+4.2), leucine (+3.8), phenylalanine (+2.8), cysteine/cystine (+2.5), methionine (+1.9), alanine (+1.8), glycine (−0.4), threonine (−0.7), serine (−0.8), tryptophan (−0.9), tyrosine (−1.3), proline (−1.6), histidine (−3.2), glutamate (−3.5), glutamine (−3.5), aspartate (−3.5), asparagine (−3.5), lysine (−3.9), and arginine (−4.5).

In making such changes, the substitution of amino acids whose hydropathic indices are within ±2 is an embodiment of the invention, those which are within +1 are optional, and those within ±0.5 are also optional.

It is also understood in the art that the substitution of like amino acids can be made effectively on the basis of hydrophilicity. U.S. Pat. No. 4,554,101 states that the greatest local average hydrophilicity of a protein, as govern by the hydrophilicity of its adjacent amino acids, correlates with a biological property of the protein.

As detailed in U.S. Pat. No. 4,554,101, the following hydrophilicity values have been assigned to amino acid residues: arginine (+3.0), lysine (+3.0), aspartate (+3.0±1), glutamate (+3.0±1), serine (+0.3), asparagine (+0.2), glutamine (+0.2), glycine (0), threonine (−0.4), proline (−0.5±1), alanine (−0.5), histidine (−0.5), cysteine (−1.0), methionine (−1.3), valine (−1.5), leucine (−1.8), isoleucine (−1.8), tyrosine (−2.3), phenylalanine (−2.5), and tryptophan (−3.4).

In making such changes, the substitution of amino acids whose hydrophilicity values are within ±2 is an embodiment of the invention, those within ±1 are optional, and those within ±0.5 are optional.

The modifications may be conservative such that the structure or biological function of the protein is not affected by the change. Such conservative amino acid modifications are based on the relative similarity of the amino acid side-chain substituents, for example, their hydrophobicity, hydrophilicity, charge, size, and the like. Exemplary conservative substitutions which take various of the foregoing characteristics into consideration are well known to those of skill in the art and include: arginine and lysine; glutamate and aspartate; serine and threonine; glutamine and asparagine; and valine, leucine, and isoleucine. The amino acid sequence of the presently disclosed antibodies may be modified to have any number of conservative changes, so long as the binding of the antibody to its target antigen is not adversely affected. Such changes may be introduced inside or outside of the antigen binding portion of the antibody. For example, changes introduced inside of the antigen binding portion of the antibody may be designed to increase the affinity of the antibody for its target.

In addition to the changes to the amino acid sequence outlined above, the antibodies can be glycosylated, pegylated, or linked to albumin or a nonproteinaceous polymer. For instance, the presently disclosed antibodies may be linked to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192; or 4,179,337. The antibodies are chemically modified by covalent conjugation to a polymer to increase their circulating half-life, for example. Certain polymers, and methods to attach them to peptides, are also shown in U.S. Pat. Nos. 4,766,106; 4,179,337; 4,495,285; and 4,609,546.

In another embodiment, the antibody may be modified to have an altered glycosylation pattern (i.e., altered from the original or native glycosylation pattern). As used herein, "altered" means having one or more carbohydrate moieties deleted, and/or having one or more glycosylation sites added to the original antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the presently disclosed antibodies is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibodies (for O-linked glycosylation sites). For ease, the antibody amino acid sequence is optionally altered through changes at the DNA level.

Another means of increasing the number of carbohydrate moieties on the antibodies is by chemical or enzymatic coupling of glycosides to the amino acid residues of the antibody. These procedures are advantageous in that they do not require production of the GDF peptide inhibitor in a host cell that has glycosylation capabilities for N- or O-linked glycosylation. Depending on the coupling mode used, the sugars may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, and in Aplin and Wriston (1981) *CRC Crit. Rev. Biochem.*, 22: 259–306.

Removal of any carbohydrate moieties present on the antibodies may be accomplished chemically or enzymatically. Chemical deglycosylation requires exposure of the antibody to trifluoromethanesulfonic acid, or an equivalent compound. This treatment results in the cleavage of most or all sugars except the linking sugar (N-acetylglucosamine or N-acetylgalactosamine), while leaving the amino acid sequence intact.

Chemical deglycosylation is described by Hakimuddin et al. (1987) *Arch. Biochem. Biophys.*, 259: 52; and Edge et al. (1981) *Anal. Biochem.*, 118: 131. Enzymatic cleavage of carbohydrate moieties on GDF peptide inhibitors can be achieved by the use of a variety of endo- and exo-glycosidases as described by Thotakura et al. (1987) *Meth. Enzymol.*, 138:350.

Sequence Analysis

While not always necessary, if desired, one of ordinary skill in the art may determine the amino acid or nucleic acid sequences of the presently disclosed antibodies. The present invention includes these amino acid and nucleic acid sequences. The present invention also include variants, homologues, and fragments of these nucleic and amino acid sequences. For example, the antibody may comprise a heavy chain variable region sequence that comprises SEQ ID NO:1, or a nucleic acid sequence that encodes SEQ ID NO:1 (e.g., SEQ ID NO:6). The nucleic or amino acid sequence optionally comprises a sequence at least 70% to 79% identical to the nucleic or amino acid sequence of the presently disclosed variable heavy chain region, optionally at least 80% to 89% identical, optionally at least 90% to 95% identical, and optionally at least 96% to 100% identical. One of skill in the art will recognize that the CDR region, which determines the antigenic binding properties of the antibody, can tolerate less sequence variation than the other portions of the antibody not involved in antigen binding. Thus, these non-binding regions of the antibody may contain substantial variations without significantly altering the binding properties of the antibody. However, one of skill in the art will also recognize that many changes can be made to the CDR region that are specifically designed to increase the affinity of the antibody for its target. Such affinity-increasing changes are typically determined empirically by altering the CDR region and testing the antibody. All such alterations, whether within the CDR or outside the CDR, are included in the scope of the present invention.

Relative sequence similarity or identity may be determined using the "Best Fit" or "Gap" programs of the Sequence Analysis Software Package™ (Version 10; Genetics Computer Group, Inc., University of Wisconsin Biotechnology Center, Madison, Wis.). "Gap" utilizes the algorithm of Needleman and Wunsch (Needleman and Wunsch, 1970)

to find the alignment of two sequences that maximizes the number of matches and minimizes the number of gaps. "BestFit" performs an optimal alignment of the best segment of similarity between two sequences. Optimal alignments are found by inserting gaps to maximize the number of matches using the local homology algorithm of Smith and Waterman (Smith and Waterman, 1981; Smith et al., 1983).

The Sequence Analysis Software Package described above contains a number of other useful sequence analysis tools for identifying homologues of the presently disclosed nucleotide and amino acid sequences. For example, the "BLAST" program (Altschul et al., 1990) searches for sequences similar to a query sequence (either peptide or nucleic acid) in a specified database (e.g., sequence databases maintained at the National Center for Biotechnology Information (NCBI) in Bethesda, Md.); "FastA" (Lipman and Pearson, 1985; see also Pearson and Lipman, 1988; Pearson et al, 1990) performs a Pearson and Lipman search for similarity between a query sequence and a group of sequences of the same type (nucleic acid or protein); "TfastA" performs a Pearson and Lipman search for similarity between a protein query sequence and any group of nucleotide sequences (it translates the nucleotide sequences in all six reading frames before performing the comparison); "FastX" performs a Pearson and Lipman search for similarity between a nucleotide query sequence and a group of protein sequences, taking frameshifts into account. "TfastX" performs a Pearson and Lipman search for similarity between a protein query sequence and any group of nucleotide sequences, taking frameshifts into account (it translates both strands of the nucleic sequence before performing the comparison).

The following examples provide embodiments of the invention. One of ordinary skill in the art will recognize the numerous modifications and variations that may be performed without altering the spirit or scope of the present invention. Such modifications and variations are believed to be encompassed within the scope of the invention. The examples do not in any way limit the invention.

The entire contents of all references, patents and published patent applications cited throughout this application are herein incorporated by reference.

EXAMPLES

Example 1

Purification of GDF-8

Conditioned media from a selected cell line expressing full-length human GDF-8 protein (mature GDF-8+GDF-8 propeptide) were acidified to pH 6.5 and applied to a 80×50 mm POROS HQ anion exchange column in tandem to a 80×50 mm POROS SP cation exchange column (PerSeptive Biosystems, Foster City, Calif.). The flow through was adjusted to pH 5.0 and applied to a 75×20 mm POROS SP cation exchange column (PerSeptive Biosystems) and eluted with a NaCl gradient. Fractions containing the GDF-8, as indicated by sodium dodecyl sulfate polyacrylamide gel electrophoresis (SDS-PAGE), were pooled, acidified with trifluoroacetic acid (TFA) to pH 2–3, then brought up to 200 ml with 0.1% TFA to lower the viscosity. The pool was then applied to a 250×21.2 mm $C_5$ column (Phenomenex, Torrance, Calif.) preceded by a 60×21.2 mm guard column (Phenomenex) and eluted with a TFA/$CH_3CN$ gradient, to separate mature GDF-8 from GDF-8 propeptide. Pooled fractions containing mature GDF-8 were concentrated by lyophilization to remove the acetonitrile and 20 ml of 0.1% TFA was added. The sample was then applied to a 250×10 mm $C_5$ column (Phenomenex) heated to 60° C. to aid in separation. This was repeated until further separation could no longer be achieved. Fractions containing mature GDF-8 were then pooled and brought up to 40% acetonitrile and applied to a 600×21.2 BioSep S-3000 size exclusion column (Phenomenex) preceded by a 60×21.2 guard column. Fractions containing purified mature GDF-8 were pooled and concentrated for use in subsequent experiments.

$C_5$ column fractions containing GDF-8 propeptide were pooled, the acetonitrile was removed by evaporation, 20 ml of 0.1% TFA was added, and the sample was then injected onto the 250×10 mm $C_5$ column at 60° C. This was repeated until further separation could no longer be achieved. Fractions containing the GDF-8 propeptide were then pooled and brought up to 40% acetonitrile and applied to a 600×21.2 BioSep S-3000 size exclusion column (Phenomenex) preceded by a 60×21.2 guard column. Fractions containing the purified GDF-8 propeptide were pooled and concentrated for use in subsequent experiments.

On SDS-PAGE, purified mature GDF-8 migrated as a broad band at 25 kDa under nonreducing conditions and 13 kDa under reducing conditions. A similar SDS-PAGE profile has been reported for murine GDF-8 (McPherron et al., 1997, supra), and reflects the dimeric nature of the mature protein.

The apparent molecular weight of purified GDF-8 propeptide was 38 kDa under both reducing and nonreducing conditions. This indicates that the GDF-8 propeptide by itself is monomeric. The difference between the apparent molecular weight and the predicted molecular weight of GDF-8 propeptide, ~26 kDa, may reflect the addition of carbohydrate, since its amino acid sequence contains a potential N-linked glycosylation site (McPherron et al., 1997, supra).

Example 2

Characteristics of Purified Recombinant Human GDF-8

50 μg each of purified mature GDF-8 and purified GDF-8 propeptide were mixed and dialyzed into 50 mM sodium phosphate, pH 7.0, and chromatographed on a 300×7.8 mm BioSep S-3000 size exclusion column (Phenomenex). Molecular weight of the mature GDF-8:propeptide complex was determined from elution time, using molecular weight standards (Bio-Rad Laboratories, Hercules, Calif.) chromatographed on the same column.

When purified GDF-8 propeptide was incubated with purified mature GDF-8 at neutral pH, the two proteins appeared to complex, as indicated by the size exclusion profile. The primary protein peak eluted at 12.7 minutes had an estimated molecular weight of 78 kDa from molecular weight standards (Bio-Rad Laboratories, Hercules, Calif.) chromatographed on the same column. The size of the complex is most consistent with one dimer of the mature GDF-8 associating with two monomers of propeptide.

To confirm this observation, a preparation containing both mature GDF-8 and GDF-8 propeptide was incubated with or without 100 mM 1-Ethyl 3-(3-dimethylaminopropyl)carbodiimide hydrochloride (EDC, Pierce) for 1 hour at room temperature (RT), acidified with HCl to pH 2–3, and concentrated with a Micron-10 Amicon concentrator (Millipore, Bedford, Mass.) for SDS-PAGE, using a tricine buffered 10% acrylamide gel. Proteins were visualized by Coomassie blue staining of the gel. In the presence of EDC, a cross-linked complex with an apparent molecular weight of 75 kDa was observed.

The GDF-8 propeptide DNA and amino acid sequence are set forth in McPherron and Lee (1997) *Proc. Natl. Acad. Sci. USA*, 94: 12457–12461.

Example 3

Production of Anti-GDF-8 Antibody

To develop an antibody capable of inhibiting GDF-8 activity, a group of GDF-8 knockout mice were immunized every two weeks with mature GDF-8 protein (purified as described in Example 1) mixed in Freunds complete adjuvant for the first two immunizations, and incomplete Freunds adjuvant thereafter. Throughout the immunization period, blood was sampled and tested for the presence of circulating antibodies. At week 9, an animal with circulating antibodies was selected, immunized for three consecutive days, and sacrificed. The spleen was removed and homogenized into cells. The spleen cells were fused to a myeloma fusion partner (line P3- x63-Ag8.653) using 50% PEG 1500 by an established procedure (Oi & Herzenberg (1980) *Selected Methods in Cellular Immunology*, W. J. Freeman Co., San Francisco, Calif., p. 351). The fused cells were plated into 96-well microtiter plates at a density of 2×10$^5$ cells/well. After 24 hours, the cells were subjected to HAT selection (Littlefield (1964) *Science*, 145: 709) effectively killing any unfused and unproductively fused myeloma cells.

Successfully fused hybridoma cells secreting anti-GDF-8 antibodies were identified by solid and solution phase ELISAs. Mature GDF-8 protein was prepared from CHO cells as described above and coated on polystyrene (for solid phase assays) or biotinylated (for a solution based assay). Neutralizing assays were also employed where the ActRIIB receptor was coated on a polystyrene plate and biotin GDF-8 binding was inhibited by the addition of hybridoma supernatant. Results identified hybridomas expressing GDF-8 antibodies. These positive clones were cultured and expanded for further study. These cultures remained stable when expanded and cell lines were cloned by limiting dilution and cryopreserved.

From these cell cultures, a panel of antibodies was developed that specifically recognize mature GDF-8. Isotype of the antibodies was determined using a mouse immunoglobulin isotyping kit (Zymed Laboratories, San Francisco, Calif.). One of the antibody clones, designated JA-16, was studied further.

Example 4

Characterization of JA-16 Binding Specificity

To determine the binding specificity of JA-16, a panel of synthetic peptides corresponding to portions of the GDF-8 protein sequence was produced. FIG. 1 shows the GDF-8 synthetic peptides used in this study. Even number peptides (N2–N14) were biotinylated on the primary amine. The biotinylated peptides N2, N4, N6, N8, N10, N12, N14, and an irrelevant peptide DAE-10, were coated at 1 µg/ml for 2 hrs at room temperature on Reacti-Bind™ Streptavidin coated polystyrene 96 well plates (Pierce, Rockford, Ill., Cat. No. 15124) following the manufacturer's protocol.

Figure 2:
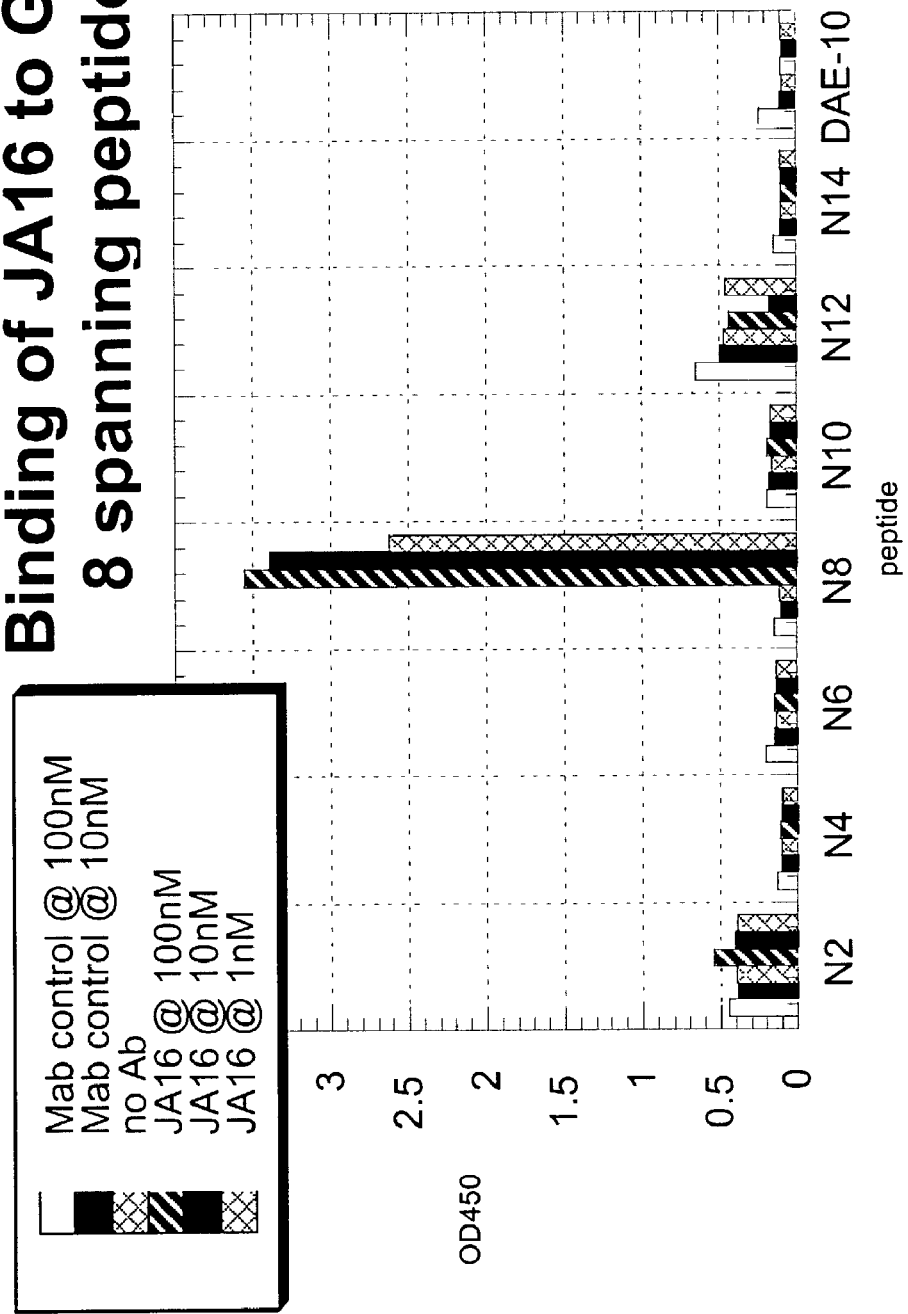
FIG. 2 shows the binding of JA-16 to the GDF-8 synthetic peptides.

After blocking, JA-16 or a unrelated monoclonal antibody control was added to the ELISA plate at 100, 10, and 1 nM (JA-16 only), and incubated for 30 min. After washing the plate, a secondary antibody (goat anti-murine IgG (H+L)-HRP, Calbiochem, San Diego, Calif., Cat. No. 401215) was added at a 1:1000 dilution and incubated for 30 minutes at room temperature. The plate was washed four times, and TMB substrate was added (KPL, Gaithersburg, Md., Cat. No. 50-76-04). Colorimetric measurements were done at 450 nm in a Molecular Devices microplate reader. The results are shown in FIG. 2. JA-16 bound strongly and specifically to the biotinylated N-terminal peptide N8 (SEQ ID NO:65).

Mature GDF-8 and BMP-11 are 90% homologous at the amino acid level (FIG. 3). Three of these changes are present within the N8 peptide. To compare the specificity of JA-16 towards GDF-8 and BMP-11, shorter peptides were designed G1 and B1 specific for GDF-8 and BMP-11, respectively. Differences between G1 and B1 are indicated with underlining.

```
G1:
Asp-Phe-Gly-Leu-Asp-Ser-Asp-Glu-His-Ser-Thr-Glu-Ser-Arg-Cys (SEQ ID NO:10)

B1:
Asn-Leu-Gly-Leu-Asp-Ser-Asp-Glu-His-Ser-Ser-Glu-Ser-Arg-Cys (SEQ ID NO:9)
```

Figure 4:
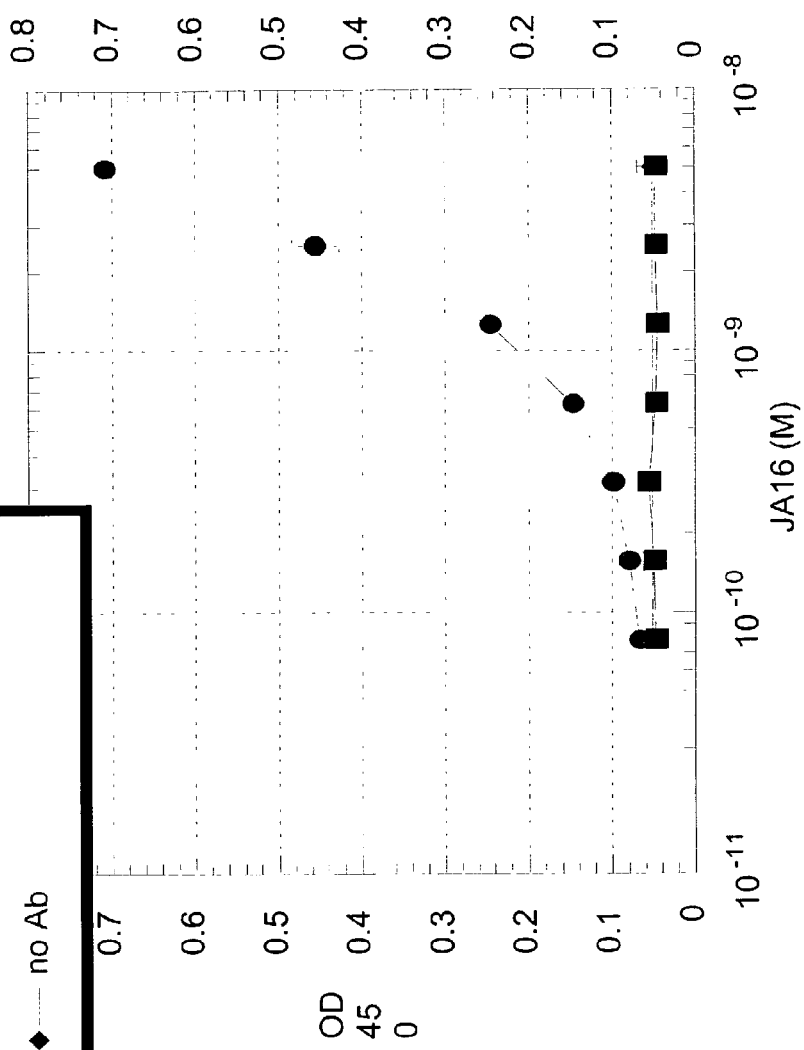
FIG. 4 shows a comparison of the binding characteristics of JA-16 to G1 peptide (SEQ ID NO:10, a peptide derived from GDF-8) conjugated to bovine serum albumin (BSA) and B1 peptide (SEQ ID NO:9, a peptide derived from BMP-11) conjugated to BSA.

The peptides G1 and B1 were conjugated to BSA using a PIERCE conjugation kit (Cat. No. 77116ZZ) following manufacturer's protocol. G1-BSA and B1-BSA were coated on 96 well flat-bottom assay plates (Costar, N.Y., Cat. No. 3590) at 1 µg/ml in 0.2 M sodium carbonate buffer overnight at 4° C. The plates were washed and blocked with PBS, 1 mg/ml BSA, 0.05% Tween for 1 hour at room temperature. JA-16 (5 nM) was serially diluted (1:2). The dilutions were added to the ELISA plate and incubated for 30 min at RT. After 4 washes, a secondary antibody (goat anti-murine IgG (H+L)-HRP, Calbiochem, Cat. No. 401215) was added at a 1:1000 dilution and incubated for 30 min at RT. Plates were washed four times, and TMB substrate was added (KPL, Cat. No. 50-76-04). Colorimetric measurements were done at 450 nm in a Molecular Devices microplate reader. FIG. 4 shows that JA-16 binds to G1-BSA in a concentration dependent manner, but not to B1-BSA, even at the highest concentration.

Figure 5:
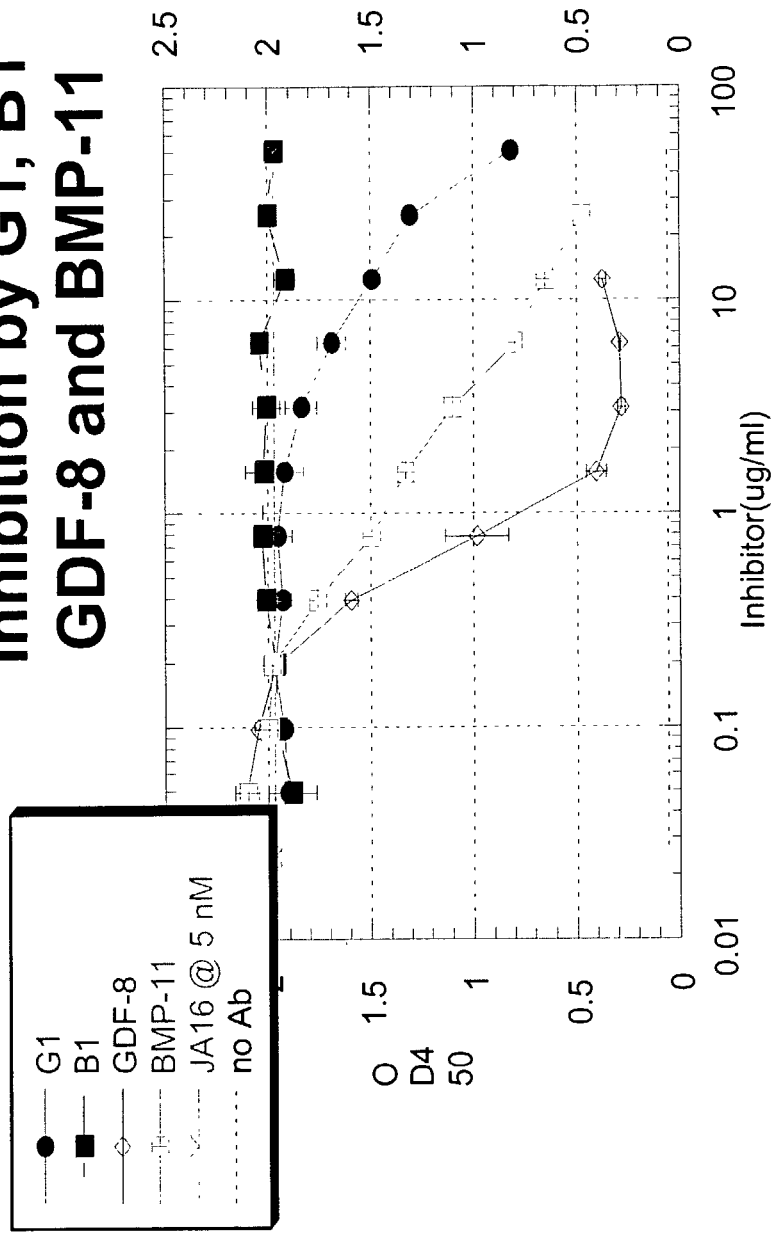
FIG. 5 shows a comparison of the binding characteristics of JA-16 to G1-BSA (SEQ ID NO:10) after JA-16 is preincubated with G1, B1, GDF-8, or BMP-11.

To look further into JA-16 specificity, G1-BSA was coated as described above, but this time, JA-16 at 5 nM was preincubated with either G1 peptide or B1 peptide, GDF-8, or BMP-11 at various concentrations. The result is shown in FIG. 5. The BMP-11 specific peptide B1 does not inhibit binding of JA-16 to G1-BSA, but G1 does. The IC$_{50}$ for GDF-8 is 0.8 µg/ml, while BMP-11's IC$_{50}$ is 3.8 µg/ml demonstrating that JA-16 recognizes GDF-8 with a 5-fold higher affinity than BMP-11.

Example 5

Mapping of JA-16 Epitope

In order to map the exact epitope of JA-16, overlapping 13-mer peptides (SEQ ID NOS:17–64, see FIG. 6A) corresponding to portions of the GDF-8 sequence were synthesized directly on cellulose paper using the spot synthesis technique (Molina et al. (1996) *Peptide Research*, 9: 151–155; Frank et al. (1992) *Tetrahedron*, 48: 9217–9232). In this array, cysteine residues were replaced with serine in order to reduce the chemical complications that are caused by the presence of cysteines. Cellulose membranes modified with polyethylene glycol and Fmoc-protected amino acids were purchased from Abimed (Lagenfeld, Germany). The array was defined on the membrane by coupling a β-alanine spacer and peptides were synthesized using standard DIC (diisopropylcarbodiimide)/HOBt (hydroxybenzotriazole) coupling chemistry as described previously (Molina et al. (1996) *Peptide Research*, 9: 151–155; Frank et al. (1992) *Tetrahedron*, 48: 9217–9232).

Activated amino acids were spotted using an Abimed ASP 222 robot. Washing and deprotection steps were done manually and the peptides were N-terminally acetylated after the final synthesis cycle. Following peptide synthesis, the membrane was washed in methanol for 10 minutes and in blocker (TBST (Tris buffered saline with 0.1% (v/v) Tween 20)+1% (w/v) casein) for 10 minutes. The membrane was then incubated with 2.5 µg/ml JA-16 in blocker for 1 hour with gentle shaking. After washing with blocker 3 times for 10 minutes, the membrane was incubated with HRP-labeled secondary antibody (0.25 µg/ml in blocker) for 30 minutes. The membrane was then washed 3 times for 10 minutes each with blocker and 2 times for 10 minutes each with TBST. Bound antibody was visualized using SuperSignal West reagent (Pierce) and a digital camera (Alphalnnotech FluorImager). Results are shown in FIG. 6B. JA-16 bound to the first 4 peptides of the array (SEQ ID NOS:17–20), which corresponds to 18 residues on the N-terminus of GDF-8.

Figure 7A:
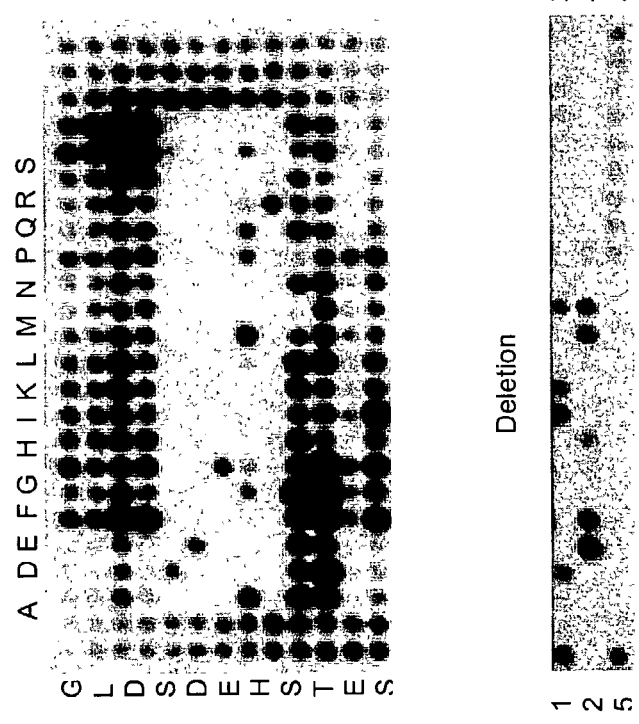
FIGS. 7A and B show the results of a deletion and substitution analysis of the JA-16 epitope region from GDF-8, Gly-Leu-Asp-Ser-Asp-Glu-His-Ser-Thr-Glu-Ser-Arg-Ser (SEQ ID NO:18), using spot synthesis.

In order to further characterize the JA-16 epitope, deletion and substitution analyses of the peptide Gly-Leu-Asp-Ser-Asp-Glu-His-Ser-Thr-Glu-Ser-Arg-Ser (SEQ ID NO: 18) were performed using spot synthesis. In the substitution analysis, each residue of this peptide was individually replaced with each of the 20 natural amino acids except cysteine, generating SEQ ID NOS: 3, 18, 66–104, 106–113, and 115–128. Synthesis and binding assays were performed as described above. The results are shown in FIG. 7. Substitutions in the 4 N-terminal amino acids and the 4 C-terminal amino acids were well tolerated, suggesting that these amino acids were not needed for JA-16 binding to mature GDF-8. However, no changes were tolerated in the middle segment of this peptide, Asp-Glu-His-Ser-Thr (SEQ ID NO:3), except for a few substitutions at the serine residue, suggesting that this peptide sequence was required for JA-16 binding. In addition, the sequence Asp-Glu-His-Ser-Thr (SEQ ID NO:3) was the smallest peptide to which binding could be detected in the deletion analysis. Thus, the results suggest that JA-16 recognizes the epitope Asp-Glu-His-Ser-Thr (SEQ ID NO:3) in GDF-8, with the Asp, Glu, His and Thr residues (Asp-Glu-His-Xaa-Thr (SEQ ID NO:2)) being important for binding.

Example 6

Characterization of JA-16 in vitro

Two assays were performed to determine the ability of JA-16 to neutralize GDF-8 activity in vitro. First, JA-16 was tested for its ability to inhibit mature GDF-8 protein binding to the ActRIIB receptor. Recombinant ActRIIB.Fc chimera (R&D Systems, Minneapolis, Minn., Cat. No. 339-RB/CF) was coated on 96 well flat-bottom assay plates (Costar, Cat. No. 3590) at 1 µg/ml in 0.2 M sodium carbonate buffer overnight at 4° C. Plates were then blocked with 1 mg/ml bovine serum albumin and washed following standard ELISA techniques.

Figure 8:
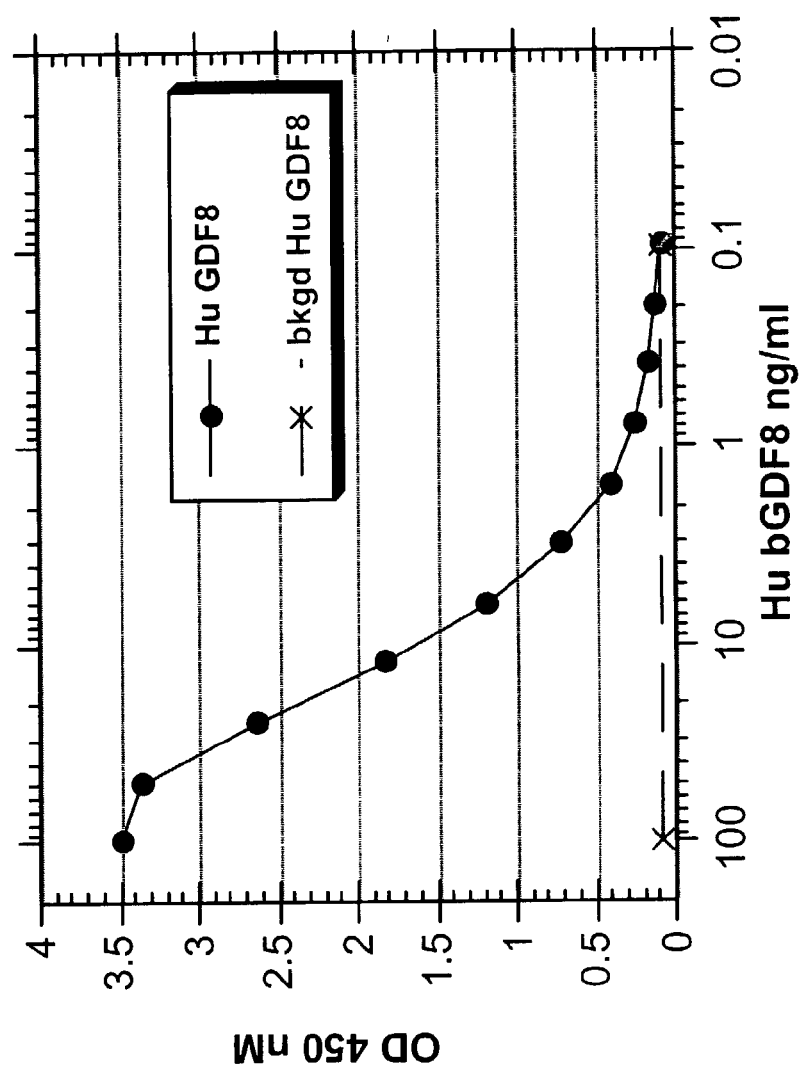
FIG. 8 shows the binding of biotinylated GDF-8 to the ActRIIB receptor.

100 µl of biotinylated mature GDF-8 protein at various concentrations was added to the blocked ELISA plates, incubated for 1 hour, and washed. The amount of bound mature GDF-8 protein was detected by streptavidin-horseradish peroxidase (SA-HRP, BD PharMingen, San Diego, Calif., Cat. No. 13047E) followed by the addition of TMB (KPL, Cat. No. 50-76-04). Colorimetric measurements were done at 450 nm in a Molecular Devices microplate reader. The results are shown in FIG. 8. The mature GDF-8 exhibited an $ED_{50}$ of 12 ng/ml.

Figure 9A:
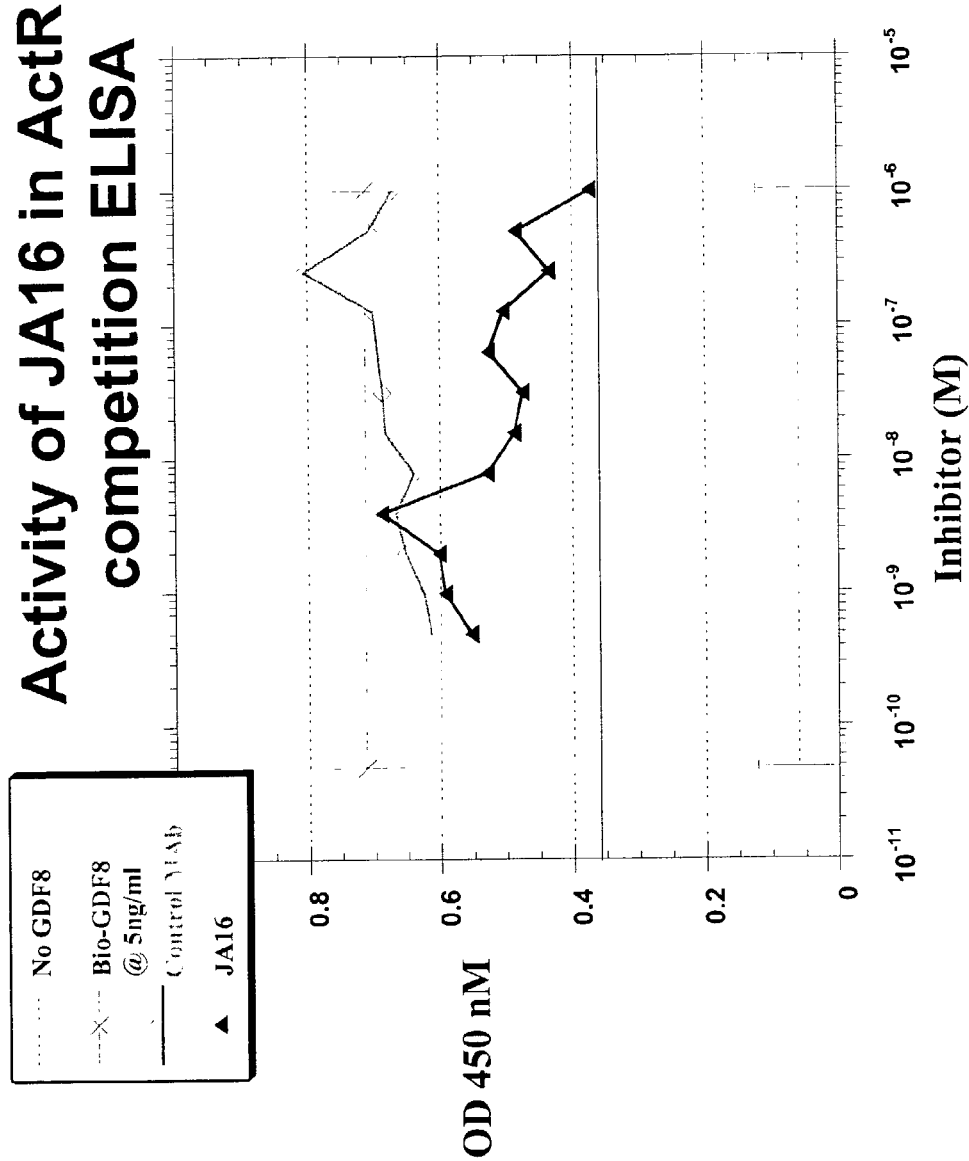
FIG. 9 shows the inhibition of biotinylated GDF-8 binding to the ActRIIB receptor in the presence and absence of JA-16.
Figure 9B:
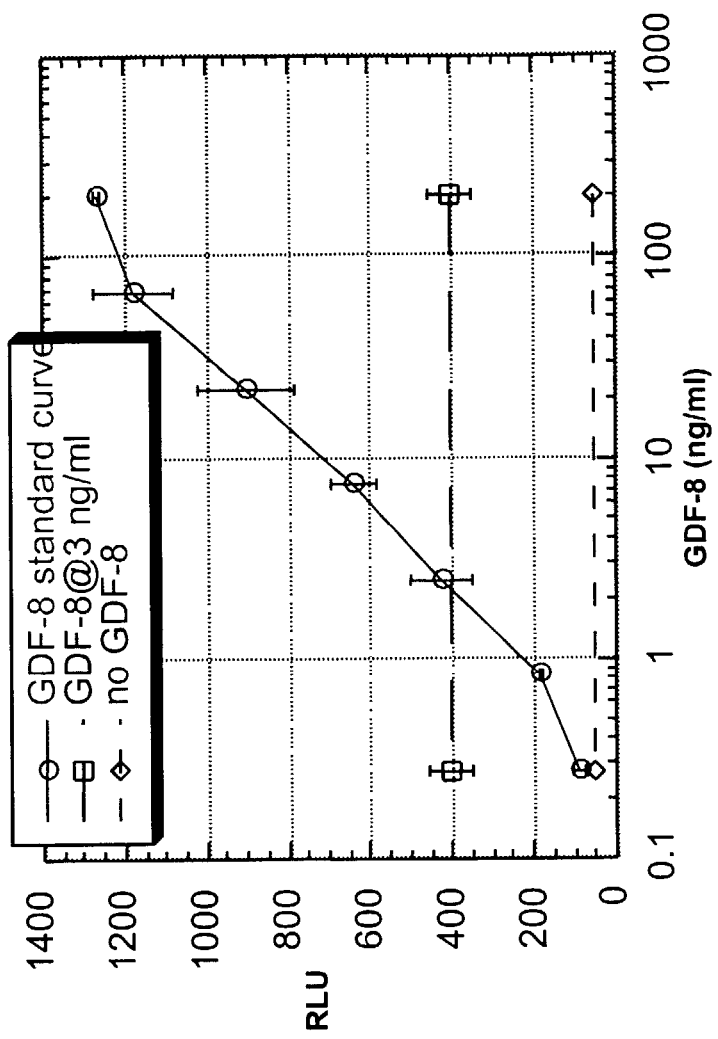

The same protocol was also performed after preincubating the JA-16 antibody with biotinylated mature GDF-8 protein at 5 ng/ml for 30 min. An irrelevelant monoclonal antibody was included as a negative control. FIG. 9 shows that JA-16 has a very weak in vitro neutralizing activity of around 1 µM. This in vitro data suggests that JA-16 is unlikely to be a very good neutralizer of active GDF-8, particularly under less controlled in vivo conditions.

In a second set of assays, a reporter gene assay was performed to assess the biological activity of active GDF-8 protein in vitro. The assay uses a reporter vector, pGL3 $(CAGA)_{12}$, coupled to luciferase. The CAGA sequence was previously reported to be a TGF-β-responsive sequence within the promoter of the TGF-β-induced gene, PAI-1.

The reporter vector containing 12 CAGA boxes was made using the basic reporter plasmid, pGL3 (Promega Corporation, Madison, Wis., Cat. No. E1751). The TATA box and transcription initiation site from the adenovirus major late promoter (−35/+10) was inserted between the BglII and HindIII sites. Oligonucleotides containing twelve repeats of the CAGA boxes AGCCAGACA were annealed and cloned into the XhoI site. The human rhabdomyosarcoma cell line, A204 (ATCC HTB-82), was transiently transfected with pGL3(CAGA)$_{12}$ using FuGENE 6 transfection reagent (Roche Diagnostics, Indianapolis, Minn. Cat. No. 1 814 443). Following transfection, cells were cultured on 48 well plates in McCoys 5A medium (Life Technologies, Rockville, Md., Cat. No. 21500-079) supplemented with 2 mM glutamine, 100 U/ml streptomycin, 100 µg/ml penicillin and 10% fetal calf serum for 16 h. Cells were then treated with mature GDF-8, BMP-11, or activin in McCoy's 5A media with glutamine, streptomycin, penicillin, and 1 mg/ml bovine serum albumin for 6 h at 37° C. Luciferase was quantified in the treated cells using the Luciferase Assay System (Promega Corporation, Madison, Wis., Cat. No. E1483). GDF-8 maximally activated the reporter construct 10-fold, with an $ED_{50}$ of 10 ng/ml GDF-8. BMP-11, which is 90% identical to GDF-8 at the amino acid level (Gamer et al. (1999) *Dev. Biol.*, 208(1): 222–32; Nakashima et al. (1999) *Mech. Dev.*, 80(2): 185–9), and activin elicited a similar biological response.

JA-16's neutralizing activity was determined by preincubating JA-16 with mature GDF-8 protein for 30 min prior to addition to the A204 cells. An irrelevant antibody (monoclonal control) as well as a human GDF-8 antibody derived from scFv phagemid library using phage display technology (Myo-19) were also tested.

Figure 10:
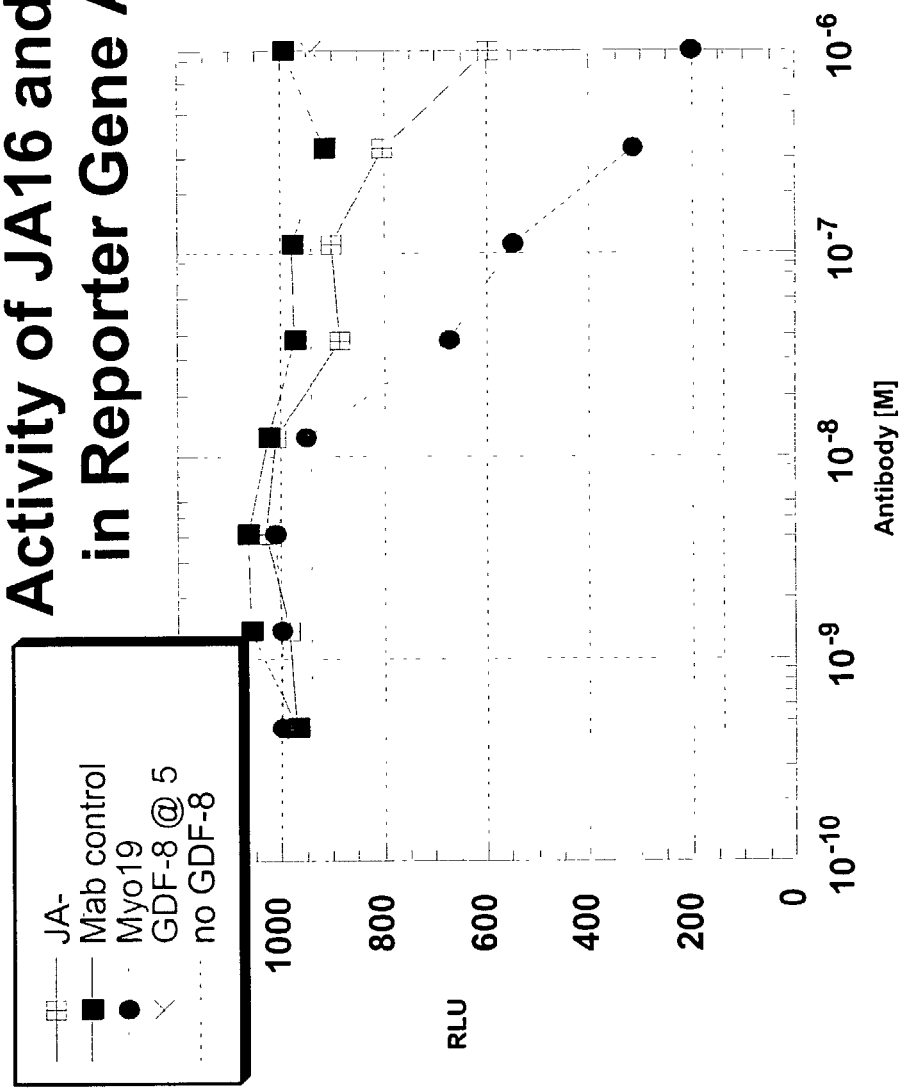
FIG. 10 shows a reporter gene assay assessing the neutralizing effect of JA-16 on the activity of GDF-8 in vitro.

FIG. 10 shows that, in this assay as well, JA-16 is weakly neutralizing with an $IC_{50}$ of around 1 µM, while the Myo-19 $IC_{50}$ is around 100 nM. Based on this in vitro data, one would have expected the Myo-19 antibody to be a better neutralizer of active GDF-8 protein than JA-16 in vivo, which is not the case, as shown herein.

Example 7

Immunoprecipitation of GDF-8 with JA-16

In order to evaluate the binding of JA-16 to mature GDF-8 and GDF-8 complexes, a series of immunoprecipitation studies were conducted.

Figure 18:
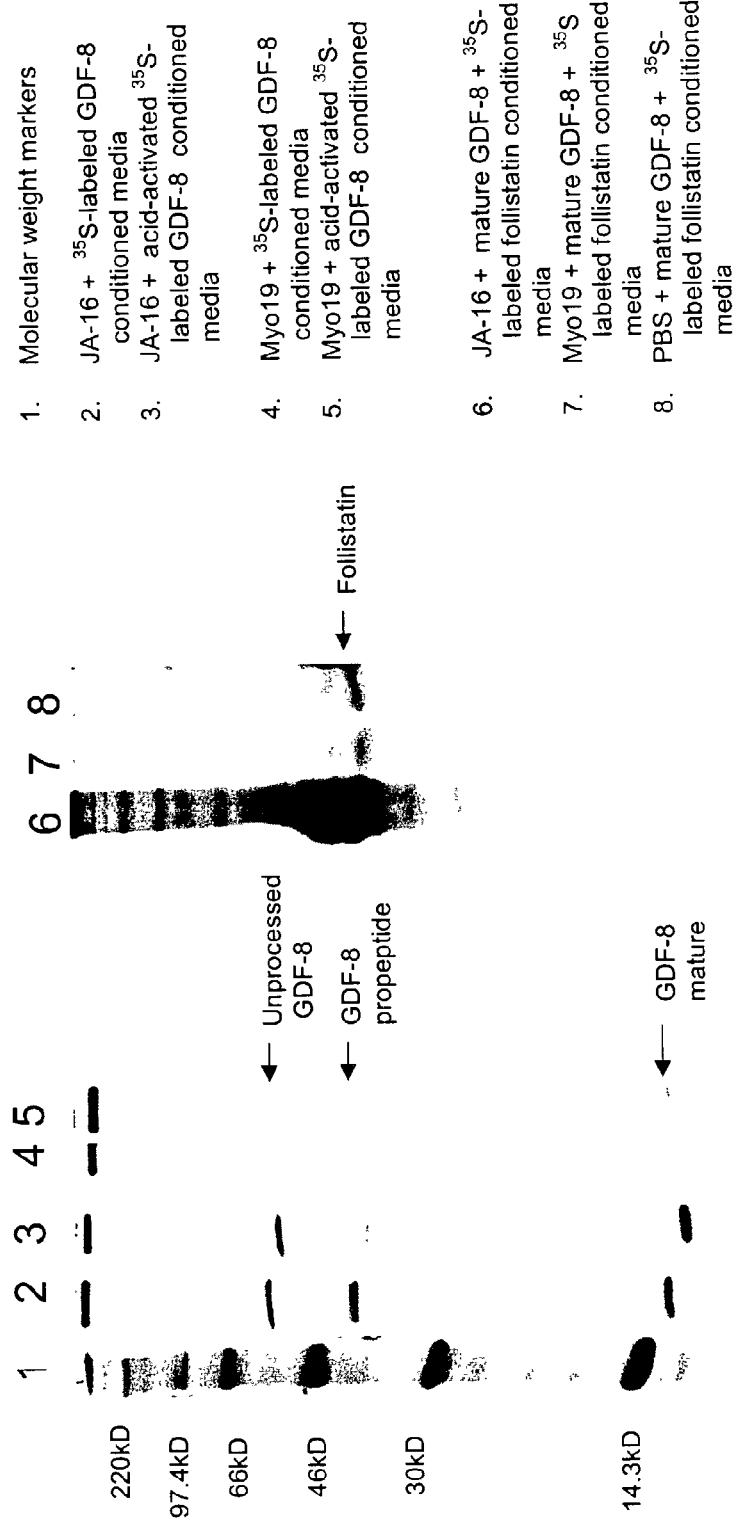
FIG. 18 shows results from the immunoprecipitation of GDF-8 with JA-16 and Myo-19.

First, to determine if JA-16 can immunoprecipitate the GDF-8 latent complex, CHO cells expressing GDF-8 were radiolabeled with $^{35}$S-methionine and $^{35}$S-cysteine. 100 µl of conditioned medium from these cells containing GDF-8 latent complex was incubated with 1 mg/ml JA-16 for 1 hour at 4° C. Protein A Sepharose was added to the mixture, which was then incubated overnight at 4° C. The immunoprecipitate was collected, washed three times with a PBS/Triton-X100 buffer, resuspended in reducing sample buffer and analyzed by SDS-PAGE. The gel was fixed overnight, enhanced with autoradiography enhancer solution, dried and the autoradiogram was developed. FIG. 18, lane 2, shows that JA-16 can immunoprecipitate the GDF-8 latent complex and unprocessed GDF-8.

Second, to determine if JA-16 can immunoprecipitate a complex formed between GDF-8 and follistatin, CHO cells expressing follistatin were radiolabeled with $^{35}$S-methionine and $^{35}$S-cysteine. 100 µl of conditioned medium containing radiolabeled follistatin was mixed with mature GDF-8 to form a complex of GDF-8 with follistatin. The mixture was incubated with 1 mg/ml JA-16 for 1 hour at 4° C. Protein A Sepharose was added to the mixture, which was then incubated overnight at 4° C. The immunoprecipitate was collected and analyzed as described above. FIG. 18, lane 6, shows that JA-16 can co-immunoprecipitate labeled follistatin complexed with GDF-8.

Third, to investigate whether JA-16 can immunoprecipitate mature GDF-8 protein, conditioned media from CHO cells containing radiolabeled GDF-8 latent complex was acid activated to dissociate the GDF-8 propeptide and mature GDF-8 (see van Waarde et al. (1997) *Analytical Biochemistry*, 247, 45–51). This material was then incubated with JA-16 for 1 hour at 4° C. The remainder of the protocol was performed as described above. FIG. 18, lane 3, shows that JA-16 can immunoprecipitate mature GDF-8.

The results indicate that JA-16 can recognize the GDF-8 latent complex, the GDF-8:follistatin complex, and mature GDF-8. In contrast, Myo-19 cannot bind any GDF-8 complexes (FIG. 18, lanes 4 and 7) and can only immunoprecipitate mature GDF-8 (FIG. 18, lane 5).

Example 8

Characterization of JA-16 in vivo

Figure 11:
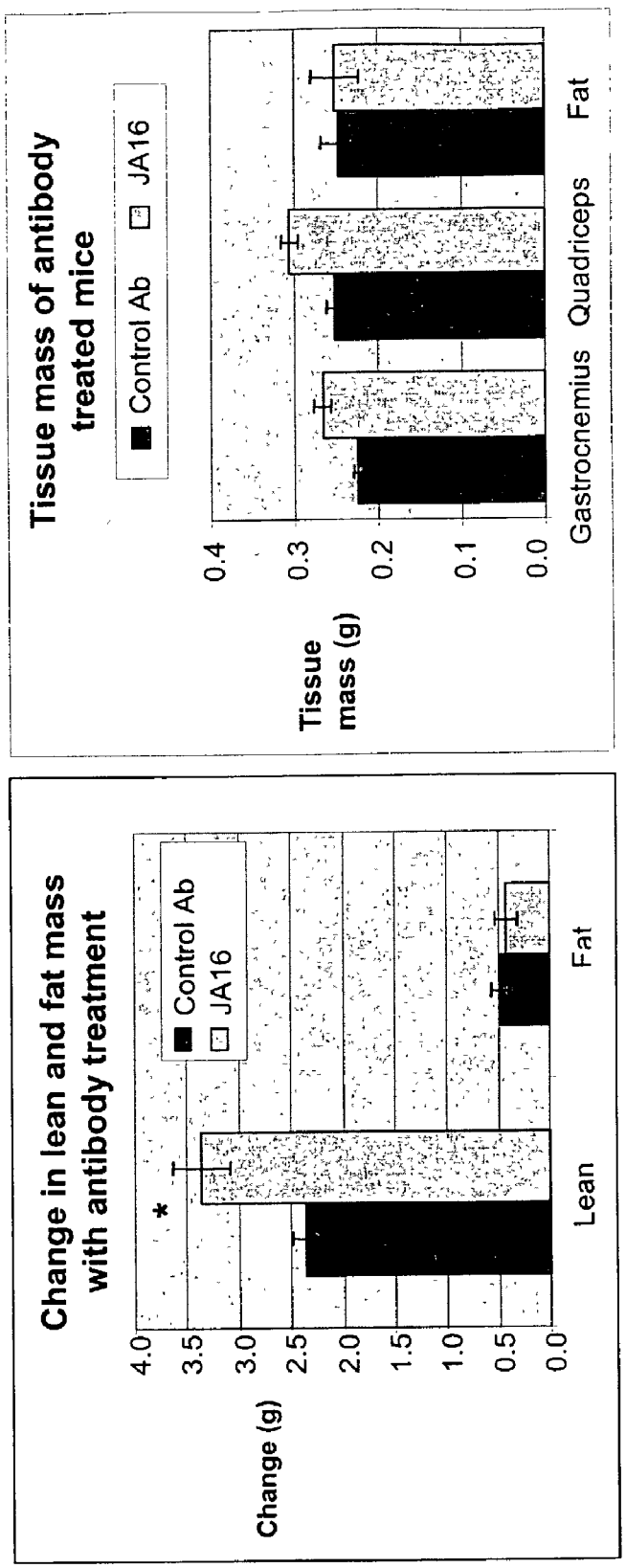
FIG. 11 shows the in vivo effect of JA-16 in mice during a 4 week study. Seven week-old female BALB/c mice were treated for four weeks with JA-16 by intraperitoneal injection at 50 mg/kg twice weekly. The graph on the left shows the change in lean and fat mass during the treatment period as measured by dexascan (dual energy x-ray) analysis. The graph on the right shows the mass of dissected tissues. A statistically significant difference, p<0.01 for a student test, is indicated by an asterisk.

In order to determine if the antibody JA-16 increases muscle mass in adult mice, an in vivo study was conducted with seven-week-old female BALB/c mice. Mice were weighed and evenly distributed with respect to body weight into groups of seven or eight. JA-16 in PBS or an isotype matched antibody to snake venom (control) was injected into the mice intraperitoneally at 50 mg/kg twice weekly. The treatment continued for four weeks. Animals were assessed for gain in lean body mass by subjecting them to dexascan analysis before and after the treatment period. Muscle mass was assessed by dissecting and weighing the gastrocnemius and quadriceps. The peri-uterine fat pad was also removed and weighed. The results of this study indicated that JA-16 significantly inhibits GDF-8 activity in vivo resulting in increased muscle mass (FIG. 11).

Figure 12:
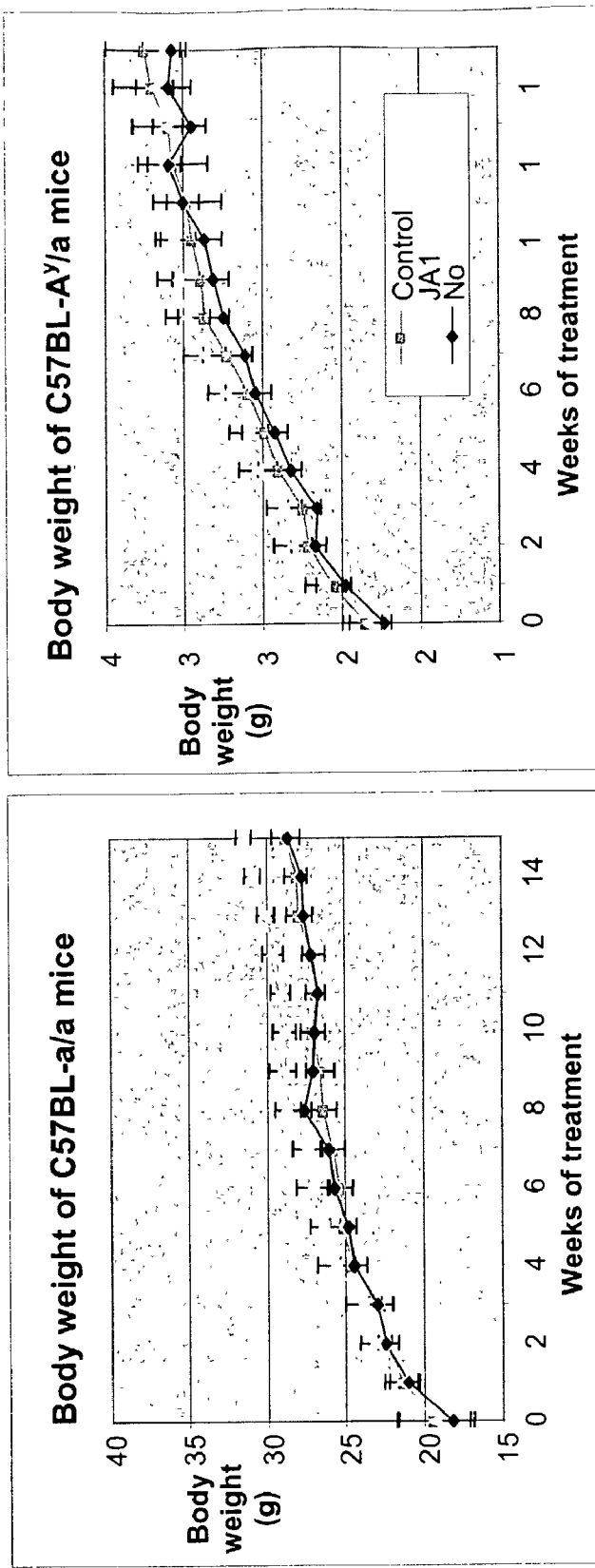
FIG. 12 shows the in vivo effect of JA-16 on total body mass of mice during a 14-week study. Male C57BL mice used in this study were either wild type at the agouti locus (a) or carried the lethal yellow mutation (Ay) at that locus. The Ay mutation causes adult onset obesity and diabetes. Young adult mice were treated with weekly intraperitoneal injections of 60 mg/kg of JA-16 or control antibody. In addition, at the start of the treatment period, mice were loaded with 60 mg/kg intraperitoneally and 10 mg/kg intravenously of the same antibody. These graphs show the weekly body weight for each group of mice. The error bars show the standard error of the mean for each data point.
Figure 13:
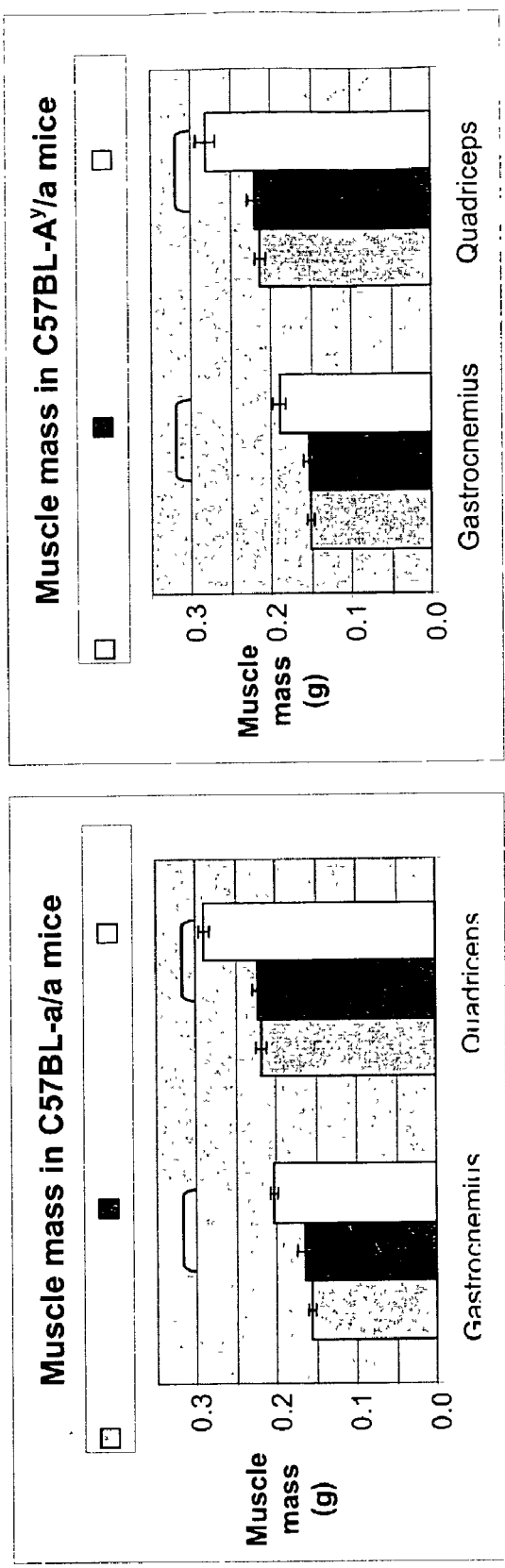
FIG. 13 shows the in vivo effect of JA-16 on total muscle mass in mice during a 14 week study. At the end of the study, muscles were dissected and weighed. These graphs show the average muscle mass for each group of mice. A statistically significant difference, p<0.01 for a student test, is indicated by an asterisk.
Figure 14:
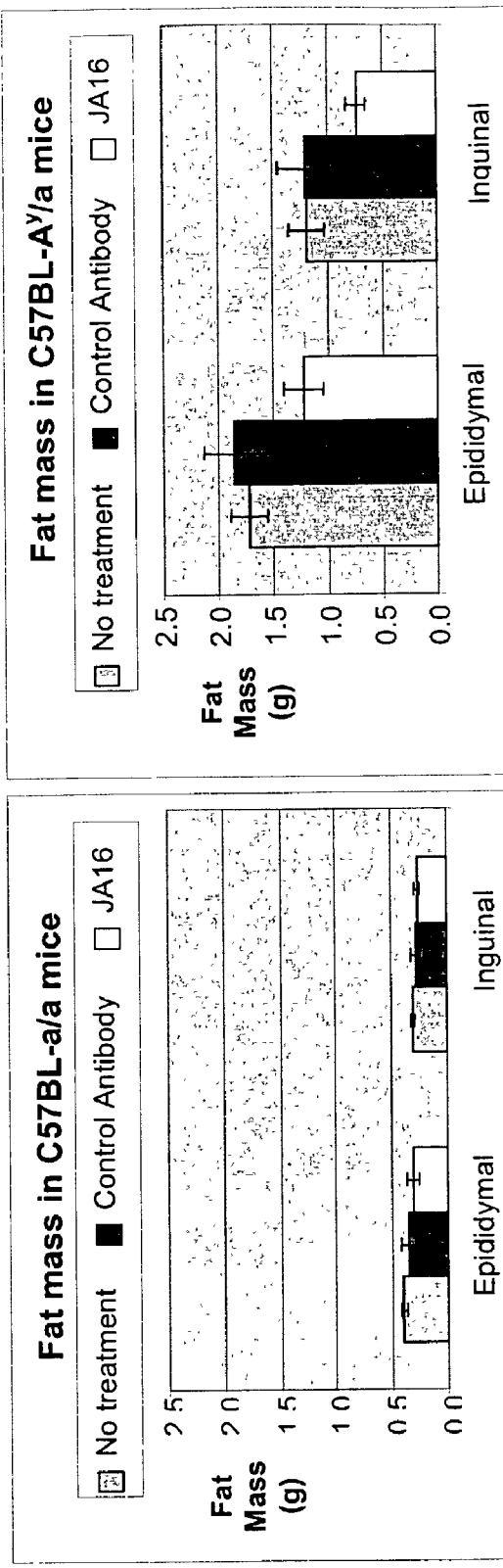
FIG. 14 shows the in vivo effect of JA-16 on total fat mass in mice during a 14-week study. At the end of the study, fat pads were dissected and weighed. These graphs show the average fat pad mass for each group of mice.
Figure 15:
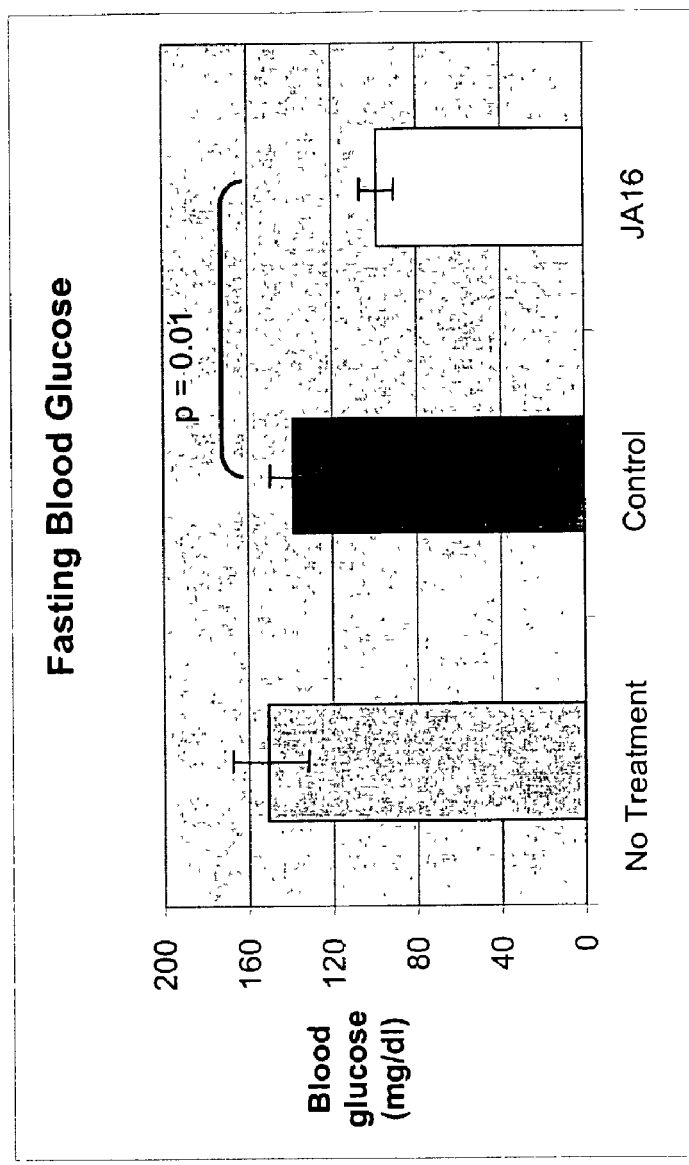
FIG. 15 shows the in vivo effect of JA-16 on blood glucose levels in mice during a 14 week study. After 12 weeks of treatment, the C57BL-Ay/a mice were fasted overnight and their blood glucose was measured.

A longer study was also performed in which the antibodies were administered intraperitoneally at 60 mg/kg/week for 14 weeks. These mice were loaded at the beginning of the study with 60 mg/kg intraperitoneally and 10 mg/kg intravenously. The mice in this study were male C57BL mice that were either wild type at the agouti locus (a) or carried the lethal yellow mutation (Ay) at that locus. The Ay mutation causes adult onset obesity and diabetes, which allowed us to determine the effect of JA-16 on muscle, excess fat, and blood glucose in a diabetic background. Total body mass was measured weekly (FIG. 12). Muscle mass was assessed by dissecting and weighing the gastrocnemius and quadriceps (FIG. 13). The epididymal and inguinal fat pads were also removed and weighed (FIG. 14). Twelve weeks into the study, the mice were fasted and blood glucose levels were measured (FIG. 15). As with the four week study, the results of this study indicate that JA-16 inhibits GDF-8 activity in vivo causing an increase in muscle mass. In addition, this study indicates that in obese and diabetic mice, inhibition of GDF-8 leads to improved levels of blood glucose.

Figure 17:
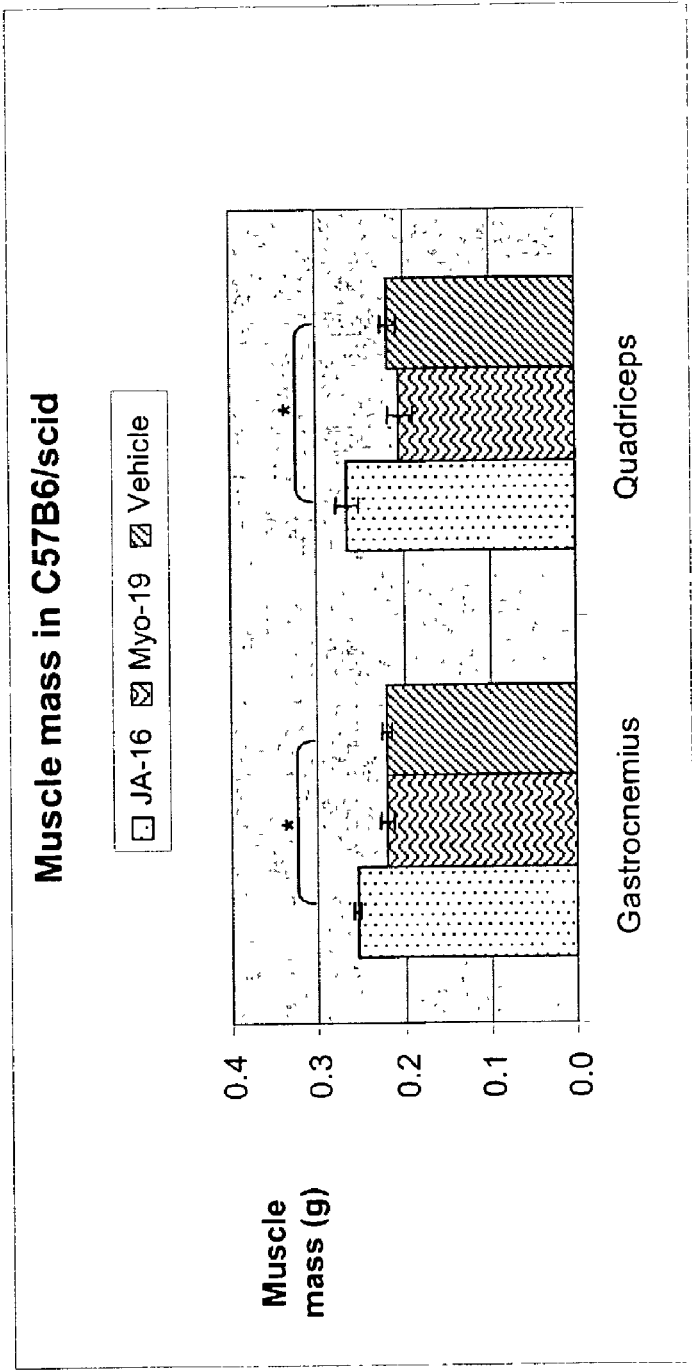
FIG. 17 shows an in vivo comparison of Myo-19 and JA-16. Seven week-old female C57B6/scid mice were treated for five weeks with JA-16, Myo-19, or vehicle by intraperitoneal injection. At the end of the study, muscles were dissected and weighed. These graphs show the average muscle mass for each group of mice. A statistically significant difference, p<0.01 for a student t-test, is indicated by an asterisk.

The in vivo activity of JA-16 was also compared to the in vivo activity of another GDF-8 antibody, Myo-19. C57B6/scid mice we injected intraperitoneally for five weeks with vehicle control or with 60 mg/kg loading dose plus 60 mg/kg per week of JA-16 or Myo-19. Total body mass was measured weekly and muscle mass was assessed by dissecting and weighing the gastrocnemius and quadriceps (FIG. 17). While five weeks of treatment with JA-16 led to an increase in muscle mass, treatment with Myo-19 did not effect muscle mass. In another experiment, Myo-19 treatment was extended to 10 and to 15 weeks, and no increase in body mass or muscle mass was seen for these time points.

Thus, despite the fact that the in vitro data suggested that JA-16 was a weaker neutralizer than Myo-19, the mouse studies clearly, but unexpectedly, demonstrate that JA-16 effectively reduces GDF-8 activity in vivo while Myo-19 does not. These results indicate that the specific site on GDF-8 to which JA-16 binds is unique in that this site is responsible for the formation of a stable inhibitory GDF-8: antibody complex in vivo. Thus, it is expected that any antibody specifically binding site, as identified in Example 4, will possess in vivo neutralizing properties similar to or better than JA-16.

Example 9

JA-16 Increases Muscle Strength

Figure 19A:
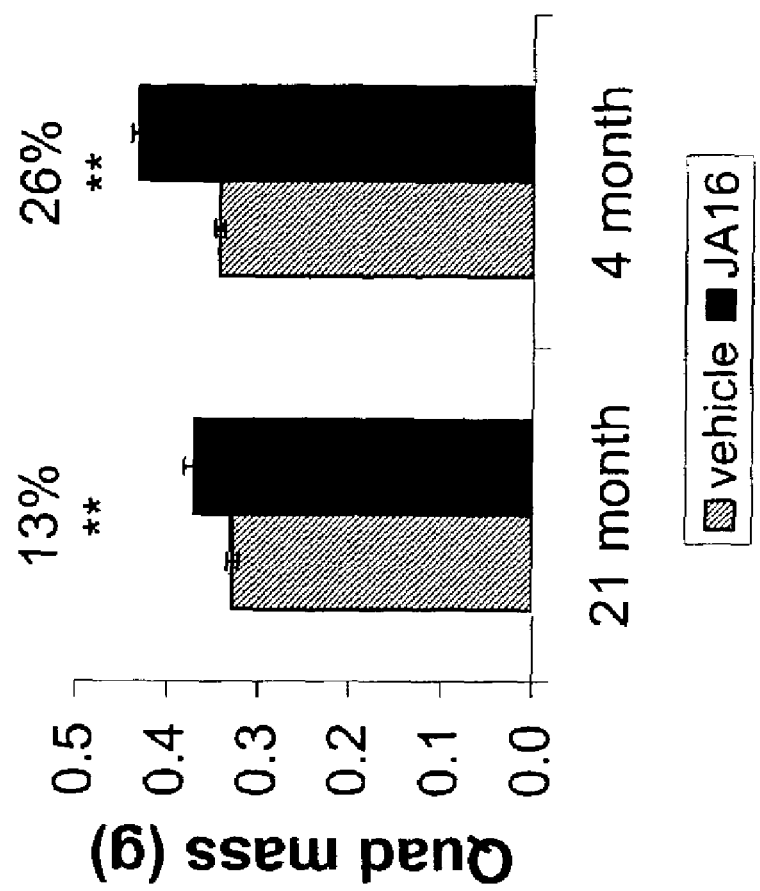
FIGS. 19A and 19B show results of JA-16 treatment in BALB/c female mice for eight weeks. Mice were 21 months or 4 months of age at the end of the study. (19A) Dissected quadriceps mass for JA-16 treated and vehicle treated mice at the end of the study. (19B) Forelimb strength determined by a grip test for JA-16 treated and vehicle treated mice after seven weeks of treatment. Each bar or data point indicates the average value for the indicated group i the standard error; (**) indicates that p<0.01 for Student's t-test comparing the JA-16 group to the vehicle group; n=8 for each group.

In humans, muscle size and strength decreases by approximately 1% per year starting in the third decade of life. For many aged people, the loss in muscle mass is significantly debilitating. This condition is known as sarcopenia, or age related loss of muscle. In order to determine if anti-GDF-8 treatment is effective for sarcopenia, aged mice (19 months of age at the beginning of the study and 21 months of age at the end of the study) were treated with JA-16 for 8 weeks at 60 mg/kg once a week. In the same experiment, young mice (2 month of age at the beginning of the study and 4 months of age at the end of the study) were treated with the same dose of JA-16. At the end of the study, both groups of mice had greater muscle mass than the vehicle treated controls as seen, for example, from the quadriceps mass comparison (FIG. 19A).

Figure 19B:
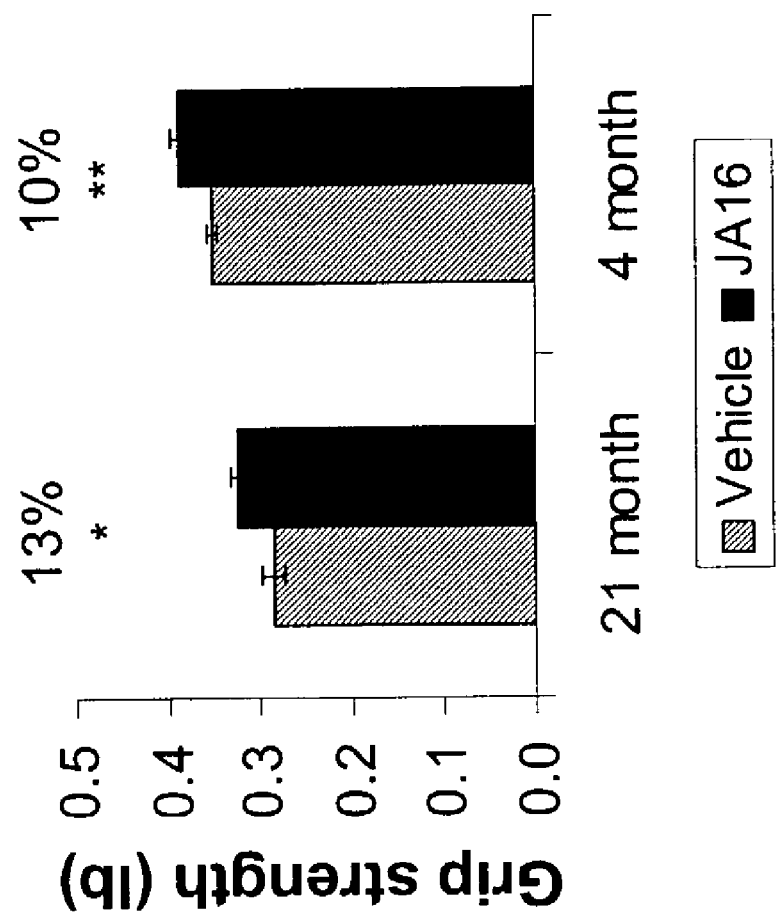

In order to confirm that the increase in muscle size leads to an increase in muscle strength, we performed grip strength tests with aged and young mice treated with JA-16 for eight weeks using a meter purchased from Columbia Instruments (Columbus, Ohio; model 1027csx). Mice were allowed to grip and pull on the grid, and the peak force of the pull was recorded. Untrained mice were tested five times in succession without rest. The peak force for each test was recorded and the results of the five tests were averaged for each mouse. After seven weeks of treatment, the peak force for the young JA-16 treated mice was 10% greater and for the aged JA-16 treated mice was 13% greater than the peak force for vehicle treated mice (FIG. 19B). In addition, longitudinal measurements taken before and after 7 weeks of treatment showed that strength of the aged mice increased by 17% (p<0.01) with JA-16 treatment, while the strength of the vehicle treated aged mice was not significantly changed (3.3%, p=0.66). These results confirm that GDF-8 inhibition leads to an increase in muscle size and strength in both young and aged mice and that it may be a useful therapy for sarcopenia.

Example 10

JA-16 Increases Muscle Mass and Strength in Dystrophic Muscle

The ability of in vivo inhibition of GDF-8 to ameliorate muscular dystrophy was tested in the mdx mouse model of Duchenne's muscular dystrophy (DMD). The DMD model has been described, for example, by Torres et al. (*Brain* (1987) 110, 269–299) and Hoffman et al. (*Science* (1987) 238, 347–350).

Figure 20A:
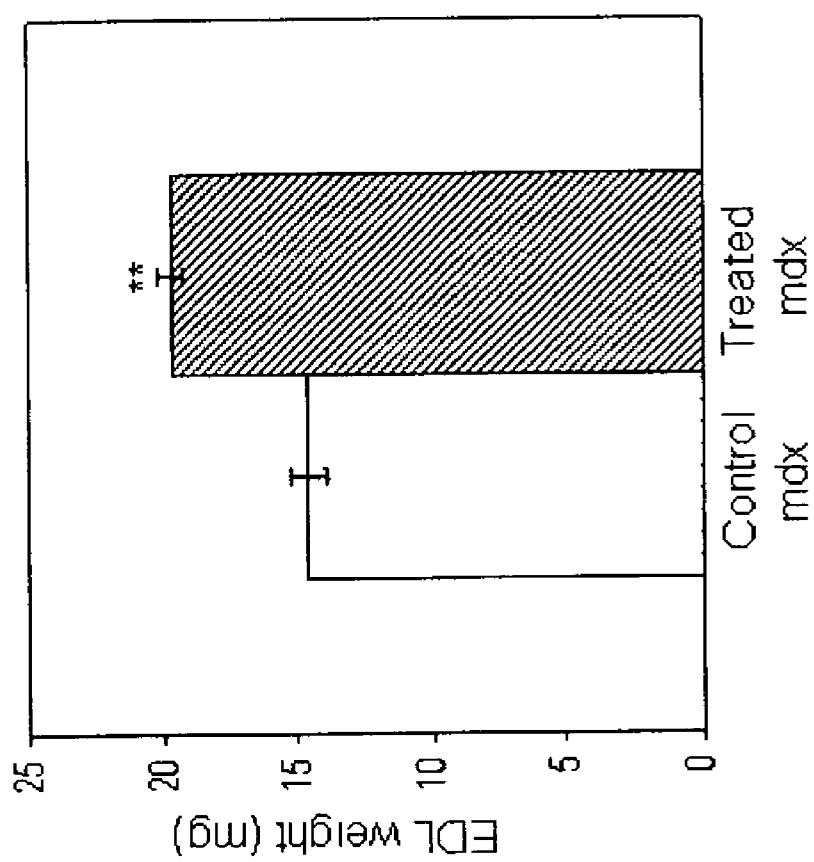
FIGS. 20A–20D show results of JA-16 treatment in mdx mice. (20A) JA-16 treated mice had significantly increased EDL weight compared to mdx controls (19.72±0.50 vs. 14.63±0.69 mg; n=12; p<0.0001). (20B) JA-16 treated mice had significantly increased muscle mass to body weight ratio (EDL weight/body weight) as compared to control (0.6±0.02 vs. 0.5±0.02; n=12; p<0.014). (20C) JA-16 treated mice generated significantly greater force during isometric twitch contraction as compared to control (177.32±8.37 vs. 132.38±12.45 mN; n=12; p<0.03). (20D) JA-16 treated mice generated significantly greater force during isometric tetanic contraction compared to control (491.23±16.34 vs. 370.74±19.21 mN; n=12; p<0.003).
Figure 20B:
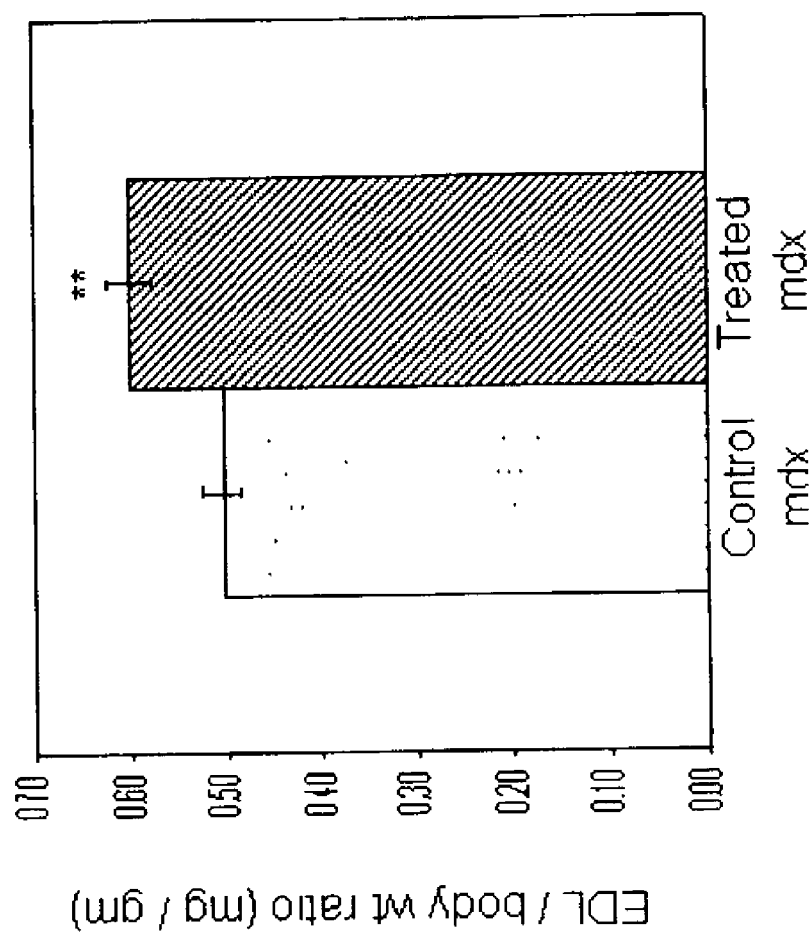

Four week old male mdx mice were treated with weekly intraperitoneal injections of JA-16 (60 mg/kg), and vehicle alone (control group) for 3 months. To quantify the increase of muscle mass, animals were sacrificed and extensor digitorum longus (EDL) muscles dissected out and weighed. As shown in FIG. 20A, EDL muscles from the treated group of animals weighed significantly more than controls. Of note, the relative increase in muscle mass was greater than the increase in body weight as shown in FIG. 20B. Consistently with this data, other muscle groups including the gastrocnemius, tibialis anterior and quadriceps were found to have similar increases in weight.

Figure 20C:
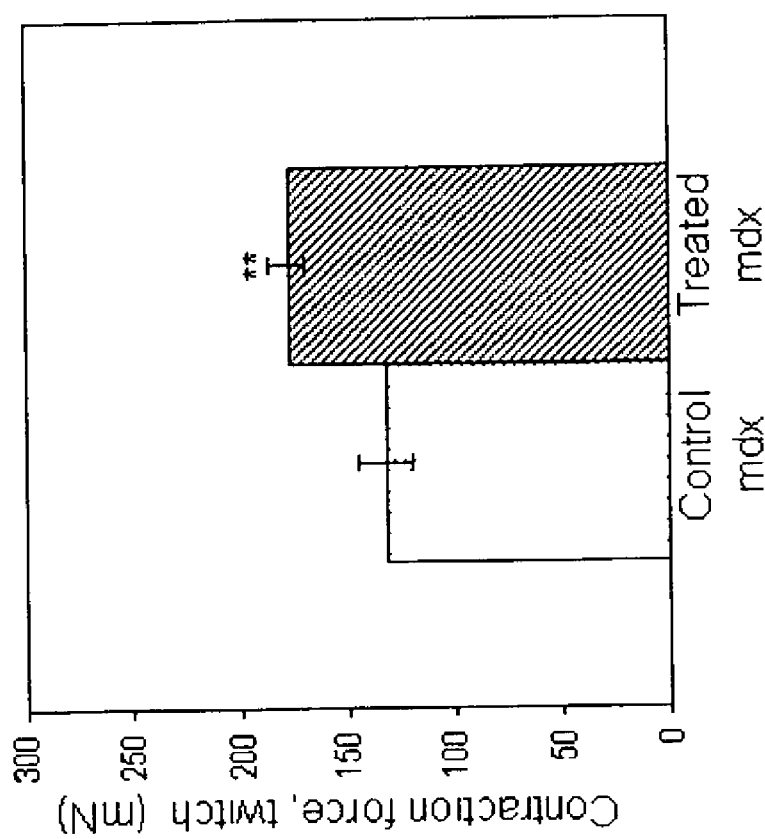
Figure 20D:
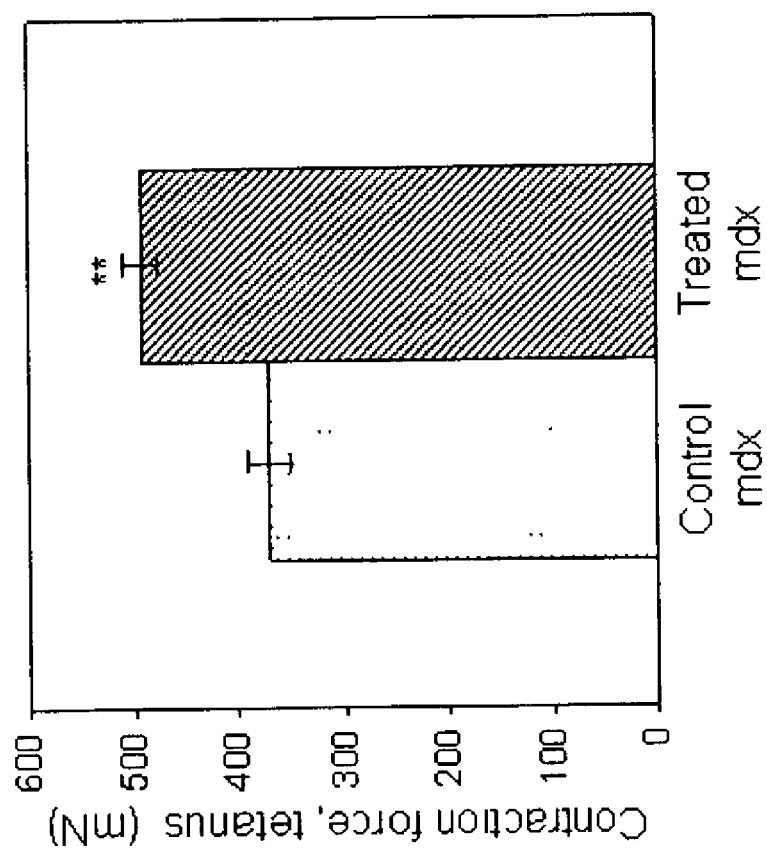

To quantify the absolute force production or muscle strength, we recorded the maximal isometric force produced upon depolarization of muscle using field electrodes. FIGS. 20C and 20D show that the JA-16 treated mdx mice were able to exert a significantly higher maximal force during either twitch or tetanus. The increase in muscle strength was proportional to the increase in muscle mass (FIGS. 20A, 20C, and 20D). These results offer physiological evidence for predicted therapeutic efficacy of GDF-8 inhibitors such as JA-16 in treatment of muscular dystrophy and related diseases.

To independently verify the amelioration of the dystrophic phenotype observed in the mdx diaphragms, as well as ascertain improvement in the pathological status of mdx skeletal musculature in toto, we analyzed serum Creatine kinase (CK) levels from these mice. Extremely high levels of CK are consistently noted with dystrophin-deficiency in mdx mice and humans due to sarcolemmal damage (Bulfield et al. (1984) *Proc. Natl. Acad. Sci. USA* 81, 1189–1192 and Matsuda et al. (1995) *J. Biochem.* (Tokyo) 118, 959–64). At the start of the trial both the treated and control groups of mdx mice had marked elevations of serum CK compared to normal mice. However, after three months of in vivo myostatin blockade there was a dramatic decline in serum CK levels of treated mdx mice (FIG. 4c). The decrease in muscle degeneration and fibrosis coupled with reduction of CK offers histological and biochemical evidence for a functional improvement in mdx muscle produced by myostatin blockade in vivo.

Example 11

In vivo Role of GDF-8 in Trabecular Bone

Increased mechanical loading, either due to increased muscle activity or increased body weight, is associated with increased bone mass and bone density. Therefore, GDF-8 knockout (KO) mice were assessed for altered bone mass and microarchitecture. An initial assessment of adult mice showed that bone density in the spine of the KO mice was nearly two-fold higher than that of their wild-type littermates. This increase far exceeded what might have been expected to be solely due to the increased muscle mass in the GDF-8 KO mice.

High resolution microtomographic imaging (μCT40, Scanco Medical, Switzerland) was used to assess the trabecular bone volume fraction and microarchitecture in the 5th lumbar vertebrae and distal femora and cortical bone geometry at the femoral mid-diaphysis of adult GDF-8 wildtype (WT) and KO mice. Specimens were taken from 9–10 month old GDF-8 male and female KO and liftermate controls (four mice of each genotype and sex). The entire vertebral body and femur were scanned using microcomputed tomography at 12 μm resolution. Regions of interest encompassing the trabecular bone of the vertebral body or the trabecular bone of the distal femoral metaphysis (i.e., secondary spongiosa) were identified using a semi-automated contouring algorithm. The following parameters were computed using direct 3D assessments: bone volume fraction (%), trabecular thickness (μm), separation (μm) and number (1/mm). In addition, the connectivity density, an indicator of how well the trabecular network is connected, was assessed as well as cortical bone parameters at the middiaphyseal region in the femur, including total area, bone area, and cortical thickness.

Both male and female KO mice had dramatically increased trabecular bone density in the vertebral body compared to WT littermates (n=4, +93% and +70%, respectively, p<0.0001). This increased trabecular bone density was accompanied by a 14% increase in trabecular thickness (p=0.03), a 38% increase in trabecular number (p=0.0002), and a 10% decrease in trabecular separation (p=0.009). The combined effect of these changes in architecture and density resulted in a 3.4- and 1.7-fold increase in connectivity in male and female KO, respectively, compared to their WT littermates (p<0.0001). In addition, a rough measure of the level of mineralization of the trabecular bone indicated that the average mineral content of the trabeculae was 8% higher in the KO mice relative to the controls (p<0.0001). There is a hint that the effect is larger in male than female mice, but the sample size is too small to make definitive conclusions. Vertebral trabecular bone characteristics assessed by high-resolution microcomputed tomography are shown in Table 1.

In contrast to observations in the spine, male and female KO mice had lower trabecular bone density in the distal femur than WT littermates (n=4, p=0.05 for overall genotype effect) (Table 2). This decrement in bone density was more pronounced in female KO than in male KO mice. GDF-8 KO mice had similar trabecular thickness as their WT littermates, but had fewer trabeculae and increased trabecular separation compared to littermate controls. However, although cortical thickness at the femoral midshaft was similar in male GDF-8 KO and their littermate controls, it was approximately 10% greater in the GDF-8 KO female mice than their WT littermates (n=4, p=0.04) (see Table 3). There were no differences in cortical bone area or bone area fraction between the two genotypes.

TABLE 1

Vertebral Trabecular Bone Characteristics (mean ± SEM)

| | Male WT | Male KO | Female WT | Female KO |
|---|---|---|---|---|
| Bone volume fraction (%) | 23.3 ± 4.7 | 45.0 ± 5.5 | 27.5 ± 5.5 | 46.9 ± 10.8 |
| Trabecular thickness (μm) | 52 ± 3 | 58 ± 6 | 52 ± 5 | 61 ± 8 |
| Trabecular separation (μm) | 210 ± 21 | 145 ± 8 | 183 ± 21 | 169 ± 41 |
| Trabecular number (1/mm) | 4.6 ± 0.4 | 7.0 ± 0.4 | 5.2 ± 0.4 | 6.6 ± 1.3 |
| Connectivity density (1/mm³) | 137 ± 15 | 470 ± 114 | 198 ± 29 | 339 ± 81 |
| Degree of anisotropy | 1.68 ± 0.08 | 1.29 ± 0.02 | 1.54 ± 0.12 | 1.34 ± 0.03 |

TABLE 2

Characteristics of the Trabecular Bone in Distal Femoral Metaphysis (mean ± SEM)

| | Male WT | Male KO | Female WT | Female KO |
|---|---|---|---|---|
| Bone volume fraction (%) | 5.1 ± 1.8 | 2.9 ± 1.7 | 11.9 ± 7.0 | 5.4 ± 3.1 |
| Trabecular thickness (μm) | 68 ± 1.2 | 68 ± 2.7 | 73 ± 7 | 63 ± 9 |
| Trabecular separation (μm) | 353 ± 16 | 472 ± 90 | 296 ± 73 | 464 ± 98 |
| Trabecular number (1/mm) | 2.84 ± 0.12 | 2.24 ± 0.51 | 3.46 ± 0.69 | 2.26 ± 0.57 |
| Connectivity density (1/mm³) | 5.9 ± 3.7 | 4.0 ± 6.9 | 31.5 ± 25.2 | 15.4 ± 15.1 |

TABLE 3

Characteristics of the Cortical Bone at the Femoral Mid-Diaphysis (mean ± SEM)

| | Male WT | Male KO | Female WT | Female KO |
|---|---|---|---|---|
| Bone Area (mm²) | 5.1 ± 1.8 | 2.9 ± 1.7 | 11.9 ± 7.0 | 5.4 ± 3.1 |
| Cortical Thickness (μm) | 68 ± 1.2 | 68 ± 2.7 | 73 ± 7 | 63 ± 9 |
| Bone Area/Total Area (%) | 353 ± 16 | 472 ± 90 | 296 ± 73 | 464 ± 98 |

Example 12

Treatment of Muscle and Bone Degenerative Disorders

Inhibitors of GDF-8, such as, for example inhibitory antibodies, are useful for treatments directed at increased muscle mass, and also for prevention and treatment of osteoporosis. In addition, inhibition of GDF-8 may be useful in other instances where a bone anabolic effect is desired, such as augmentation of bone healing (i.e., fracture repair, spine fusion, etc.). The anti-GDF-8 antibodies of the invention are used to treat a subject at disease onset or having an established muscle or bone degenerative disease.

Efficacy of anti-GDF-8 antibodies for treatment of bone disorders, e.g., osteoporosis, is confirmed using well established models of osteoporosis. For example, ovariectomized mice have been used to test the efficacy of new osteoporosis drug treatments (Alexander et al. (2001) *J. Bone Min. Res.* 16: 1665–1673; and Anderson et al. (2001) *J. Endocrinol.* 170:529–537). Similar to humans, these rodents exhibit a rapid loss of bone following ovariectomy, especially in cancellous bone. Outcome assessments are based on bone mineral density, biochemical markers of bone turnover in serum and urine, bone strength, and histology/histomorphometry.

In one study, normal and/or immune compromised female mice are ovariectomized at 12–16 weeks of age and allowed to lose bone for four to six weeks. Following this bone loss period, treatment with an anti-GDF-8 antibody such as JA-16 (IP injection) or vehicle is conducted for one to six months. The treatment protocol could vary, with testing of different doses and treatment regimens (e.g., daily, weekly, or bi-weekly injections). It is anticipated that untreated ovariectomized mice (or rats) would lose approximately 10–30% of bone density relative to intact (i.e., non-ovariectomized), age-matched mice. It is anticipated that mice treated with the anti-GDF-8 antibody would have 10 to 50% greater bone mass and bone density than those mice receiving placebo, and moreover that this increase in bone density would be associated with increased bone strength, particularly in regions with a greater proportion of cancellous bone compared to cortical bone.

The goal of another study is to demonstrate that anti-GDF-8 antibody such as JA-16 is effective in preventing the decline in bone mass, microarchitecture and strength associated with estrogen deficiency. Thus, the study has a similar design to the one described above, except that treatment with anti-GDF-8 antibody would be initiated immediately after ovariectomy, rather than after the bone loss period. It is anticipated that mice treated with the antibody would lose significantly less bone mass following ovariectomy than mice treated with vehicle.

The inhibitory antibodies against GDF-8 are also used to prevent and/or to reduce severity and/or the symptoms of the disease. It is anticipated that the anti-GDF-8 antibodies would be administered as a subcutaneous injection as frequently as once per day and as infrequently as once per month. Treatment duration could range between one month and several years.

To test the clinical efficacy of anti-GDF-8 in humans, postmenopausal women with low bone mass are identified by bone density testing and randomized to a treatment group. Treatment groups include a placebo group and one to three groups receiving antibody (different doses). Individuals are followed prospectively for one to three years to assess changes in biochemical markers of bone turnover, changes in bone mineral density, and the occurrence of fragility fractures. It is anticipated that individuals receiving treatment would exhibit an increase in bone mineral density in the proximal femur and lumbar spine of 2–30% relative to baseline, and would have a decreased incidence of fragility fractures. It is anticipated that biochemical markers of bone formation would increase.

The antibodies are administered as the sole active compound or in combination with another compound or composition. When administered as the sole active compound or in combination with another compound or composition, the dosage may be between approximately 1 μg/kg and 20 mg/kg, depending on the severity of the symptoms and the progression of the disease. The appropriate effective dose is selected by a treating clinician from the following ranges: 1 µg/kg and 20 mg/kg, 1 µg/kg and 10 mg/kg, 1 µg/kg and 1 mg/kg, 10 µg/kg and 1 mg/kg, 10 µg/kg and 100 µg/kg, 100 µg and 1 mg/kg, and 500 µg/kg and 1 mg/kg. Exemplary treatment regimens and outcomes are summarized in Table 4.

TABLE 4

Examples of Clinical Cases

| Patient No. | Status prior to treatment | Treatment Regimen | Outcome |
|---|---|---|---|
| Patient 1 | No clinical signs, postmenopausal and/or over 60 years old | 0.01–1 mg/kg biweekly for 4–24 weeks | Maintenance and/or increase of muscle/bone mass |
| Patient 2 | Mild clinical signs, muscle wasting and/or bone loss | 0.01–20 mg/kg weekly for 4 more weeks | Maintenance and/or increase of muscle/bone mass |
| Patient 3 | Advanced stage of osteoporosis | 0.01–20 mg/kg twice weekly for 6 or more weeks | Improvement of clinical signs, maintenance and/or increase of muscle/bone mass |
| Patient 4 | Severe muscle and bone loss | 0.01–20 mg/kg daily for 6 or more weeks | Improvement of clinical signs, reduction in severity of symptoms and/or increase of muscle/bone mass |

Example 13

Treatment of Metabolic Disorders

Inhibitors of GDF-8, such as, for example inhibitory antibodies, are useful for treatment of metabolic disorders such as type 2 diabetes, impaired glucose tolerance, metabolic syndrome (e.g., syndrome X), insulin resistance induced by trauma (e.g., burns), and adipose tissue disorders (e.g., obesity). The anti-GDF-8 antibodies of the invention are used to treat a subject at disease onset or having an established metabolic disease.

Efficacy of anti-GDF-8 antibodies for treatment of metabolic disorders, e.g., type 2 diabetes and/or obesity, is confirmed using well established murine models of obesity, insulin resistance and type 2 diabetes, including ob/ob, db/db, and strains carrying the lethal yellow mutation. Insulin resistance can also be induced by high fat or high caloric feeding of certain strains of mice including, C57BL/6J. Similar to humans, these rodents develop insulin resistance, hyperinsuliemia, dyslipidemia, and deterioration of glucose homeostasis resulting in hyperglycemia. Outcome assessments are based on serum measurements of glucose, insulin, and lipids. Improved insulin sensitivity can be determined by insulin tolerance tests and glucose tolerance tests. More sensitive techniques would include the use of euglycemic-hyperinsulinemic clamps for assessing improvements is glycemic control and insulin sensitivity. In addition, the clamp techniques would allow a quantitative assessment of the role of the major glucose disposing tissues (e.g., muscle, adipose, and liver) in improved glycemic control.

In one study, treatment with an anti-GDF-8 antibody such as JA-16 (IP injection) or vehicle is conducted for one week to six months. The treatment protocol could vary, with testing of different doses and treatment regimens (e.g., daily, weekly, or bi-weekly injections). It is anticipated that mice treated with the anti-GDF-8 antibody would have greater glucose uptake, increased glycolysis and glycogen synthesis, lower free fatty acids and triglycerides in the serum as compared to mice receiving placebo treatment.

The inhibitory antibodies against GDF-8 are also used to prevent and/or to reduce severity and/or the symptoms of the disease. It is anticipated that the anti-GDF-8 antibodies would be administered as a subcutaneous injection as frequently as once per day and as infrequently as once per month. Treatment duration could range between one month and several years.

To test the clinical efficacy of anti-GDF-8 in humans, subjects suffering from or at risk for type 2 diabetes are identified and randomized to a treatment group. Treatment groups include a placebo group and one to three groups receiving antibody (different doses). Individuals are followed prospectively for one month to three years to assess changes in glucose metabolism. It is anticipated that individuals receiving treatment would exhibit an improvement.

The antibodies are administered as the sole active compound or in combination with another compound or composition. When administered as the sole active compound or in combination with another compound or composition, the dosage may be between approximately 1 µg/kg and 20 mg/kg, depending on the severity of the symptoms and the progression of the disease. The appropriate effective dose is selected by a treating clinician from the following ranges: 1 µg/kg and 20 mg/kg, 1 µg/kg and 10 mg/kg, 1 µg/kg and 1 mg/kg, 10 µg/kg and 1 mg/kg, 10 µg/kg and 100 µg/kg, 100 µg and 1 mg/kg, and 500 µg/kg and 1 mg/kg. Exemplary treatment regimens and outcomes are summarized in Table 5.

TABLE 5

Examples of Clinical Cases

| Patient No. | Status prior to treatment | Treatment Regimen | Outcome |
|---|---|---|---|
| Patient 1 | No clinical signs, family history of type 2 diabetes | 0.01–1 mg/kg every 4 weeks for 48 weeks | Prevention of type 2 diabetes |
| Patient 2 | Mild clinical signs of syndrome X | 0.01–20 mg/kg weekly for 4 more weeks | Improved insulin tolerance and glucose metabolism, and lower blood pressure |
| Patient 3 | Advanced stage of type 2 diabetes | 0.01–20 mg/kg twice weekly for 6 or more weeks | Improvement of clinical signs, reduction in severity of symptoms and/or increase in muscle mass/body fat ratio |
| Patient 4 | Severe insulin resistance and/or obesity | 0.01–20 mg/kg daily for 6 or more weeks | Improvement of clinical signs, reduction in severity of symptoms and/or decrease in body fat |

We claim:

1. An isolated antibody that specifically binds to amino acids 1–50 of the polypeptide of SEQ ID NO:15, wherein the antibody reduces GDF-8 activity associated with negative regulation of muscle mass.

2. The antibody of claim 1, wherein the antibody specifically binds to amino acids 1–25 of the polypeptide of SEQ ID NO:15.

3. The antibody of claim 1, wherein the antibody specifically binds to the polypeptide of SEQ ID NO:8.

4. The antibody of claim 1, wherein the antibody specifically binds to the polypeptide of SEQ ID NO:3.

5. The antibody of claim 1, wherein the antibody recognizes the GDF-8 latent complex, GDF-8 in complex with follistatin, or GDF-8 in complex with a follistatin related protein.

6. The antibody of claim 5, wherein the antibody recognizes the GDF-8 latent complex.

7. The antibody of claim 5, wherein the antibody recognizes GDF-8 in complex with follistatin.

8. The antibody of claim 5, wherein the antibody recognizes GDF-8 in complex with a follistatin related protein.

9. The antibody of claim 1, wherein the antibody is a monoclonal antibody.

10. A pharmaceutical composition comprising the antibody of claim 1.

11. The composition of claim 10, further comprising a pharmaceutically acceptable excipient.

12. A diagnostic kit comprising the antibody of claim 1.

13. The antibody of claim 1, wherein the antibody specifically binds to the polypeptide of SEQ ID NO:15, but not to the polypeptide of SEQ ID NO:16.

14. The antibody of claim 1, wherein the antibody is chimeric.

15. The antibody of claim 1, wherein the antibody is a fragment chosen from a single-chain, Fab, F(ab')$_2$, and Fv antibody.

16. The antibody of claim 1, wherein the antibody specifically binds with an affinity constant of greater than $10^6$ M$^{-1}$.

17. The antibody of claim 1, wherein the antibody specifically binds with an affinity constant of greater than $10^8$ M$^{-1}$.

18. An isolated antibody that specifically binds to the polypeptide of SEQ ID NO:5, wherein the antibody reduces GDF-8 activity associated with negative regulation of muscle mass.

19. A diagnostic kit comprising the antibody of claim 18.

20. An isolated monoclonal antibody that specifically binds to amino acids 1–50 of the polypeptide of SEQ ID NO:15, wherein the antibody has the same specificity as an antibody produced by a cell having ATCC Deposit Designation Number PTA-4236.

21. An antibody produced by the cell having ATCC Deposit Designation Number PTA-4236.

22. An isolated antibody that specifically binds to the polypeptide of SEQ ID NO:2, wherein the antibody reduces GDF-8 activity associated with negative regulation of muscle mass.

23. The antibody of claim 22, wherein the antibody specifically binds to the polypeptide of SEQ ID NO:3.

24. An isolated antibody that specifically binds to the polypeptide of SEQ ID NO:5, wherein the antibody reduces GDF-8 activity associated with negative regulation of muscle mass.

25. The antibody of claim 24, wherein the antibody specifically binds to the polypeptide of SEQ ID NO:18.

26. An isolated antibody having the same amino acid sequence as an antibody produced by a cell having ATCC Deposit Designation Number PTA-4236.

27. An isolated antibody that specifically binds to the polypeptide of SEQ ID NO:2, wherein the antibody comprises at least one single chain CDR chosen from amino acids 30–35 of the polypeptide of SEQ ID NO:1, amino acids 50–66 of the polypeptide of SEQ ID NO:1, and amino acids 99–102 of the polypeptide of SEQ ID NO:1.

28. An isolated antibody that specifically binds to the polypeptide of SEQ ID NO. 10, wherein the antibody binds to a mature GDF-8 protein with greater affinity than to a mature BMP-11 protein and reduces GDF-8 activity associated with negative regulation of muscle mass.

29. The antibody of claim 28, wherein the antibody is as produced by a cell having ATCC Deposit Designation Number PTA-4236.

30. An antibody comprising a heavy chain variable region that comprises an amino acid sequence, wherein the amino acid sequence is SEQ ID NO:1, and wherein the antibody specifically binds to a mature GDF-8 protein and reduces one or more biological activities associated with the GDF-8 protein, relative to a GDF-8 protein that is not bound by the same antibody.

31. An isolated antibody that specifically binds to the polypeptide of SEQ ID NO:8, wherein the antibody comprises at least one single chain CDR chosen from amino acids 30–35 of the polypeptide of SEQ ID NO:1, amino acids 50–66 of polypeptide of SEQ ID NO:1, and amino acids 99–102 of the polypeptide of SEQ ID NO:1, and wherein the antibody reduces GDF-8 activity associated with negative regulation of muscle mass.

32. The antibody of claim 31, wherein the antibody is a monoclonal antibody.

33. The antibody of claim 31, wherein the antibody is chimeric.

34. The antibody of claim 31, wherein the antibody is a fragment chosen from a single-chain, Fab, F(ab')$_2$, and Fv antibody.

35. An antibody comprising a heavy chain variable region that comprises an amino acid sequence at least 95% identical to SEQ ID NO:1, wherein the antibody comprises CDRs of the amino acids 30–35 of the polypeptide of SEQ ID NO:1, amino acids 50–66 of the polypeptide of SEQ ID NO:1, and amino acids 99–102 of the polypeptide of SEQ ID NO:1, and wherein the antibody reduces GDF-8 activity associated with negative regulation of muscle mass.

* * * * *

SEQUENCE LISTING

<160> NUMBER OF SEQ ID NOS: 131

<210> SEQ ID NO 1
<211> LENGTH: 113
<212> TYPE: PRT
<213> ORGANISM: Homo sapiens
<220> FEATURE:
<221> NAME/KEY: misc_feature
<222> LOCATION: (1)..(1)
<223> OTHER INFORMATION: X is an unknown amino acid
<220> FEATURE:
<221> NAME/KEY: misc_feature
<222> LOCATION: (113)..(113)
<223> OTHER INFORMATION: X is an unknown amino acid

<400> SEQUENCE: 1

Xaa Val Lys Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Phe
            20                  25                  30

Tyr Met Tyr Trp Val Lys Gln Arg Pro Gly Gln Gly Leu Glu Trp Ile
        35                  40                  45

Gly Glu Ile Asn Pro Ser Asn Gly Asp Thr Asn Phe Ile Glu Ser Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Val Arg Phe Ala Tyr Trp Gly Gln Gly Thr Thr Val Thr Val Ser
            100                 105                 110

Xaa

<210> SEQ ID NO 2
<211> LENGTH: 5
<212> TYPE: PRT
<213> ORGANISM: Homo sapiens
<220> FEATURE:
<221> NAME/KEY: misc_feature
<222> LOCATION: (4)..(4)
<223> OTHER INFORMATION: X is an unknown amino acid

<400> SEQUENCE: 2

Asp Glu His Xaa Thr
1               5

<210> SEQ ID NO 3
<211> LENGTH: 5
<212> TYPE: PRT
<213> ORGANISM: Homo sapiens

<400> SEQUENCE: 3

Asp Glu His Ser Thr
1               5

<210> SEQ ID NO 4
<211> LENGTH: 1128
<212> TYPE: DNA
<213> ORGANISM: Homo sapiens

<400> SEQUENCE: 4
atgcaaaaac tgcaactctg tgtttatatt tacctgttta tgctgattgt tgctggtcca      60

-continued

| | |
|---|---|
| gtggatctaa atgagaacag tgagcaaaaa gaaaatgtgg aaaaagaggg gctgtgtaat | 120 |
| gcatgtactt ggagacaaaa cactaaatct tcaagaatag aagccattaa gatacaaatc | 180 |
| ctcagtaaac ttcgtctgga aacagctcct aacatcagca aagatgttat aagacaactt | 240 |
| ttacccaaag ctcctccact ccgggaactg attgatcagt atgatgtcca gagggatgac | 300 |
| agcagcgatg gctctttgga agatgacgat tatcacgcta caacggaaac aatcattacc | 360 |
| atgcctacag agtctgattt tctaatgcaa gtggatggaa acccaaatg ttgcttcttt | 420 |
| aaatttagct ctaaaataca atacaataaa gtagtaaagg cccaactatg gatatatttg | 480 |
| agacccgtcg agactcctac aacagtgttt gtgcaaatcc tgagactcat caaacctatg | 540 |
| aaagacggta caaggtatac tggaatccga tctctgaaac ttgacatgaa cccaggcact | 600 |
| ggtatttggc agagcattga tgtgaagaca gtgttgcaaa attggctcaa acaacctgaa | 660 |
| tccaacttag gcattgaaat aaaagcttta gatgagaatg gtcatgatct tgctgtaacc | 720 |
| ttcccaggac aggagaaga tgggctgaat ccgttttag aggtcaaggt aacagacaca | 780 |
| ccaaaaagat ccagaaggga ttttggtctt gactgtgatg agcactcaac agaatcacga | 840 |
| tgctgtcgtt accctctaac tgtggatttt gaagcttttg gatgggattg gattatcgct | 900 |
| cctaaaagat ataaggccaa ttactgctct ggagagtgtg aatttgtatt tttacaaaaa | 960 |
| tatcctcata ctcatctggt acaccaagca accccagag gttcagcagg cccttgctgt | 1020 |
| actcccacaa agatgtctcc aattaatatg ctatatttta atggcaaaga acaaataata | 1080 |
| tatgggaaaa ttccagcgat ggtagtagac cgctgtgggt gctcatga | 1128 |

```
<210> SEQ ID NO 5
<211> LENGTH: 15
<212> TYPE: PRT
<213> ORGANISM: Homo sapiens
<220> FEATURE:
<221> NAME/KEY: misc_feature
<222> LOCATION: (10)..(10)
<223> OTHER INFORMATION: X is an unknown amino acid

<400> SEQUENCE: 5

Asp Phe Gly Leu Asp Cys Asp Glu His Xaa Thr Glu Ser Arg Cys
1               5                   10                  15

<210> SEQ ID NO 6
<211> LENGTH: 339
<212> TYPE: DNA
<213> ORGANISM: Homo sapiens
<220> FEATURE:
<221> NAME/KEY: misc_feature
<222> LOCATION: (1)..(3)
<223> OTHER INFORMATION: N is an unknown nucleotide
<220> FEATURE:
<221> NAME/KEY: misc_feature
<222> LOCATION: (337)..(339)
<223> OTHER INFORMATION: N is an unknown nucleotide

<400> SEQUENCE: 6
```

| | |
|---|---|
| nnngtgaagc tgcagcagtc aggggctgaa ctggtgaagc ctggggcttc agtgaagttg | 60 |
| tcctgcaagg cttctggcta caccttcacc agcttctata tgtactgggt gaagcagagg | 120 |
| cctggacaag gccttgagtg gattggagag attaatccta gcaatggtga tactaacttc | 180 |
| attgagagtt tcaagagcaa ggccacactg actgtagaca aatcctccag cacagcatac | 240 |
| atgcaactca gcagcctgac atctgaggac tctgcggtct attactgtac tgtgagattt | 300 |
| gcttactggg gccaagggac cacggtcacc gtctccnnn | 339 |

<210> SEQ ID NO 7
<211> LENGTH: 1259
<212> TYPE: DNA
<213> ORGANISM: Homo sapiens

<400> SEQUENCE: 7

```
ccgcggcggc ggcggcggcg gcggcggcgg cggcagcggc gggggtcggg ggggagcgct      60
ccagccggcc agcccgtcc gtggcgcccg agccggacgg ctgccccgtg tgcgtttggc      120
ggcagcacag ccgcgagctg cgcctagaga gcatcaagtc gcagatcttg agcaaactgc    180
ggctcaagga ggcgcccaac atcagccgcg aggtggtgaa cagctgctg cccaaggcgc    240
cgccgctgca gcagatcctg gacctacacg acttccaggg cgacgcgctg cagcccgagg    300
acttcctgga ggaggacgag taccacgcca ccaccgagac cgtcattagc atggcccagg    360
agacggaccc agcagtacag acagatggca gccctctctg ctgccatttt cacttcagcc    420
ccaaggtgat gttcacaaag gtactgaagg cccagctgtg gtgtaccta cggcctgtac    480
cccgcccagc cacagtctac ctgcagatct tgcgactaaa ccctaact ggggaaggga    540
ccgcagggg aggggcgga ggccggcgtc acatccgtat ccgctcactg aagattgagc    600
tgcactcacg ctcaggccat tggcagagca tcgacttcaa gcaagtgcta cacagctggt    660
tccgccagcc acagagcaac tggggcatcg agatcaacgc ctttgatccc agtggcacag    720
acctggctgt cacctccctg gggccgggag ccgagggct gcatccattc atggagcttc    780
gagtcctaga gaacacaaaa cgttcccggc ggaacctggg tctggactgc gacgagcact    840
caagcgagtc ccgctgctgc cgatatcccc tcacagtgga ctttgaggct ttcggctggg    900
actggatcat cgcacctaag cgctacaagg ccaactactg ctccggccag tgcgagtaca    960
tgttcatgca aaatatccg catacccatt tggtgcagca ggccaatcca agaggctctg   1020
ctgggccctg ttgtaccccc accaagatgt ccccaatcaa catgctctac ttcaatgaca   1080
agcagcagat tatctacggc aagatccctg gcatggtggt ggatcgctgt ggctgctctt   1140
aaggtgggtc actacaagct gctggagcaa agacttggtg ggtgggtaac ttaacctctt   1200
cacagaggat aaaaaatgct tgtgagtatg acagaaggga ataaacaggc ttaaagggt    1259
```

<210> SEQ ID NO 8
<211> LENGTH: 15
<212> TYPE: PRT
<213> ORGANISM: Homo sapiens

<400> SEQUENCE: 8

Asp Phe Gly Leu Asp Cys Asp Glu His Ser Thr Glu Ser Arg Cys
1               5                   10                  15

<210> SEQ ID NO 9
<211> LENGTH: 15
<212> TYPE: PRT
<213> ORGANISM: Homo sapiens

<400> SEQUENCE: 9

Asn Leu Gly Leu Asp Ser Asp Glu His Ser Ser Glu Ser Arg Cys
1               5                   10                  15

<210> SEQ ID NO 10
<211> LENGTH: 15
<212> TYPE: PRT
<213> ORGANISM: Homo sapiens

<400> SEQUENCE: 10

```
Asp Phe Gly Leu Asp Ser Asp Glu His Ser Thr Glu Ser Arg Cys
1               5                   10                  15

<210> SEQ ID NO 11
<211> LENGTH: 26
<212> TYPE: PRT
<213> ORGANISM: Homo sapiens

<400> SEQUENCE: 11

Arg Tyr Pro Leu Thr Val Asp Phe Glu Ala Phe Gly Trp Asp Trp Ile
1               5                   10                  15

Ile Ala Pro Lys Arg Tyr Lys Ala Asn Tyr
            20                  25

<210> SEQ ID NO 12
<211> LENGTH: 25
<212> TYPE: PRT
<213> ORGANISM: Homo sapiens

<400> SEQUENCE: 12

Glu Phe Val Phe Leu Gln Lys Tyr Pro His Thr His Leu Val His Gln
1               5                   10                  15

Ala Asn Pro Arg Gly Ser Ala Gly Pro
            20                  25

<210> SEQ ID NO 13
<211> LENGTH: 31
<212> TYPE: PRT
<213> ORGANISM: Homo sapiens

<400> SEQUENCE: 13

Thr Pro Thr Lys Met Ser Pro Ile Asn Met Leu Tyr Phe Asn Gly Lys
1               5                   10                  15

Glu Gln Ile Ile Tyr Gly Lys Ile Pro Ala Met Val Val Asp Arg
            20                  25                  30

<210> SEQ ID NO 14
<211> LENGTH: 109
<212> TYPE: PRT
<213> ORGANISM: Homo sapiens

<400> SEQUENCE: 14

Asp Phe Gly Leu Asp Ser Asp Glu His Ser Thr Glu Ser Arg Ser Ser
1               5                   10                  15

Arg Tyr Pro Leu Thr Val Asp Phe Glu Ala Phe Gly Trp Asp Trp Ile
                20                  25                  30

Ile Ala Pro Lys Arg Tyr Lys Ala Asn Tyr Ser Ser Gly Glu Ser Glu
            35                  40                  45

Phe Val Phe Leu Gln Lys Tyr Pro His Thr His Leu Val His Gln Ala
    50                  55                  60

Asn Pro Arg Gly Ser Ala Gly Pro Ser Ser Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Ser Gly Ser Ser
            100                 105

<210> SEQ ID NO 15
<211> LENGTH: 109
<212> TYPE: PRT
```

<213> ORGANISM: Homo sapiens

<400> SEQUENCE: 15

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105

<210> SEQ ID NO 16
<211> LENGTH: 109
<212> TYPE: PRT
<213> ORGANISM: Homo sapiens

<400> SEQUENCE: 16

Asn Leu Gly Leu Asp Cys Asp Glu His Ser Ser Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Gln Cys Glu
        35                  40                  45

Tyr Met Phe Met Gln Lys Tyr Pro His Thr His Leu Val Gln Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Asp Lys Gln Gln Ile Ile Tyr Gly
                85                  90                  95

Lys Ile Pro Gly Met Val Val Asp Arg Cys Gly Cys Ser
            100                 105

<210> SEQ ID NO 17
<211> LENGTH: 13
<212> TYPE: PRT
<213> ORGANISM: Homo sapiens

<400> SEQUENCE: 17

Asp Phe Gly Leu Asp Ser Asp Glu His Ser Thr Glu Ser
1               5                   10

<210> SEQ ID NO 18
<211> LENGTH: 13
<212> TYPE: PRT
<213> ORGANISM: Homo sapiens

<400> SEQUENCE: 18

Gly Leu Asp Ser Asp Glu His Ser Thr Glu Ser Arg Ser
1               5                   10

<210> SEQ ID NO 19
<211> LENGTH: 13

```
<212> TYPE: PRT
<213> ORGANISM: Homo sapiens

<400> SEQUENCE: 19

Asp Ser Asp Glu His Ser Thr Glu Ser Arg Ser Ser Arg
1               5                   10

<210> SEQ ID NO 20
<211> LENGTH: 13
<212> TYPE: PRT
<213> ORGANISM: Homo sapiens

<400> SEQUENCE: 20

Asp Glu His Ser Thr Glu Ser Arg Ser Ser Arg Tyr Pro
1               5                   10

<210> SEQ ID NO 21
<211> LENGTH: 13
<212> TYPE: PRT
<213> ORGANISM: Homo sapiens

<400> SEQUENCE: 21

His Ser Thr Glu Ser Arg Ser Ser Arg Tyr Pro Leu Thr
1               5                   10

<210> SEQ ID NO 22
<211> LENGTH: 13
<212> TYPE: PRT
<213> ORGANISM: Homo sapiens

<400> SEQUENCE: 22

Thr Glu Ser Arg Ser Ser Arg Tyr Pro Leu Thr Val Asp
1               5                   10

<210> SEQ ID NO 23
<211> LENGTH: 13
<212> TYPE: PRT
<213> ORGANISM: Homo sapiens

<400> SEQUENCE: 23

Ser Arg Ser Ser Arg Tyr Pro Leu Thr Val Asp Phe Glu
1               5                   10

<210> SEQ ID NO 24
<211> LENGTH: 13
<212> TYPE: PRT
<213> ORGANISM: Homo sapiens

<400> SEQUENCE: 24

Ser Ser Arg Tyr Pro Leu Thr Val Asp Phe Glu Ala Phe
1               5                   10

<210> SEQ ID NO 25
<211> LENGTH: 13
<212> TYPE: PRT
<213> ORGANISM: Homo sapiens

<400> SEQUENCE: 25

Arg Tyr Pro Leu Thr Val Asp Phe Glu Ala Phe Gly Trp
1               5                   10

<210> SEQ ID NO 26
<211> LENGTH: 13
<212> TYPE: PRT
<213> ORGANISM: Homo sapiens
```

```
<400> SEQUENCE: 26

Pro Leu Thr Val Asp Phe Glu Ala Phe Gly Trp Asp Trp
1               5                   10

<210> SEQ ID NO 27
<211> LENGTH: 13
<212> TYPE: PRT
<213> ORGANISM: Homo sapiens

<400> SEQUENCE: 27

Thr Val Asp Phe Glu Ala Phe Gly Trp Asp Trp Ile Ile
1               5                   10

<210> SEQ ID NO 28
<211> LENGTH: 13
<212> TYPE: PRT
<213> ORGANISM: Homo sapiens

<400> SEQUENCE: 28

Asp Phe Glu Ala Phe Gly Trp Asp Trp Ile Ile Ala Pro
1               5                   10

<210> SEQ ID NO 29
<211> LENGTH: 13
<212> TYPE: PRT
<213> ORGANISM: Homo sapiens

<400> SEQUENCE: 29

Glu Ala Phe Gly Trp Asp Trp Ile Ile Ala Pro Lys Arg
1               5                   10

<210> SEQ ID NO 30
<211> LENGTH: 13
<212> TYPE: PRT
<213> ORGANISM: Homo sapiens

<400> SEQUENCE: 30

Phe Gly Trp Asp Trp Ile Ile Ala Pro Lys Arg Tyr Lys
1               5                   10

<210> SEQ ID NO 31
<211> LENGTH: 13
<212> TYPE: PRT
<213> ORGANISM: Homo sapiens

<400> SEQUENCE: 31

Trp Asp Trp Ile Ile Ala Pro Lys Arg Tyr Lys Ala Asn
1               5                   10

<210> SEQ ID NO 32
<211> LENGTH: 13
<212> TYPE: PRT
<213> ORGANISM: Homo sapiens

<400> SEQUENCE: 32

Trp Ile Ile Ala Pro Lys Arg Tyr Lys Ala Asn Tyr Ser
1               5                   10

<210> SEQ ID NO 33
<211> LENGTH: 13
<212> TYPE: PRT
<213> ORGANISM: Homo sapiens

<400> SEQUENCE: 33
```

```
Ile Ala Pro Lys Arg Tyr Lys Ala Asn Tyr Ser Ser Gly
1               5                   10
```

<210> SEQ ID NO 34
<211> LENGTH: 13
<212> TYPE: PRT
<213> ORGANISM: Homo sapiens

<400> SEQUENCE: 34

```
Pro Lys Arg Tyr Lys Ala Asn Tyr Ser Ser Gly Glu Ser
1               5                   10
```

<210> SEQ ID NO 35
<211> LENGTH: 13
<212> TYPE: PRT
<213> ORGANISM: Homo sapiens

<400> SEQUENCE: 35

```
Arg Tyr Lys Ala Asn Tyr Ser Ser Gly Glu Ser Glu Phe
1               5                   10
```

<210> SEQ ID NO 36
<211> LENGTH: 13
<212> TYPE: PRT
<213> ORGANISM: Homo sapiens

<400> SEQUENCE: 36

```
Lys Ala Asn Tyr Ser Ser Gly Glu Ser Glu Phe Val Phe
1               5                   10
```

<210> SEQ ID NO 37
<211> LENGTH: 13
<212> TYPE: PRT
<213> ORGANISM: Homo sapiens

<400> SEQUENCE: 37

```
Asn Tyr Ser Ser Gly Glu Ser Glu Phe Val Phe Leu Gln
1               5                   10
```

<210> SEQ ID NO 38
<211> LENGTH: 13
<212> TYPE: PRT
<213> ORGANISM: Homo sapiens

<400> SEQUENCE: 38

```
Ser Ser Gly Glu Ser Glu Phe Val Phe Leu Gln Lys Tyr
1               5                   10
```

<210> SEQ ID NO 39
<211> LENGTH: 13
<212> TYPE: PRT
<213> ORGANISM: Homo sapiens

<400> SEQUENCE: 39

```
Gly Glu Ser Glu Phe Val Phe Leu Gln Lys Tyr Pro His
1               5                   10
```

<210> SEQ ID NO 40
<211> LENGTH: 13
<212> TYPE: PRT
<213> ORGANISM: Homo sapiens

<400> SEQUENCE: 40

```
Ser Glu Phe Val Phe Leu Gln Lys Tyr Pro His Thr His
```

```
1               5                   10
```

<210> SEQ ID NO 41
<211> LENGTH: 13
<212> TYPE: PRT
<213> ORGANISM: Homo sapiens

<400> SEQUENCE: 41

```
Phe Val Phe Leu Gln Lys Tyr Pro His Thr His Leu Val
1               5                   10
```

<210> SEQ ID NO 42
<211> LENGTH: 13
<212> TYPE: PRT
<213> ORGANISM: Homo sapiens

<400> SEQUENCE: 42

```
Phe Leu Gln Lys Tyr Pro His Thr His Leu Val His Gln
1               5                   10
```

<210> SEQ ID NO 43
<211> LENGTH: 13
<212> TYPE: PRT
<213> ORGANISM: Homo sapiens

<400> SEQUENCE: 43

```
Gln Lys Tyr Pro His Thr His Leu Val His Gln Ala Asn
1               5                   10
```

<210> SEQ ID NO 44
<211> LENGTH: 13
<212> TYPE: PRT
<213> ORGANISM: Homo sapiens

<400> SEQUENCE: 44

```
Pro His Thr His Leu Val His Gln Ala Asn Pro Arg Gly
1               5                   10
```

<210> SEQ ID NO 45
<211> LENGTH: 13
<212> TYPE: PRT
<213> ORGANISM: Homo sapiens

<400> SEQUENCE: 45

```
Thr His Leu Val His Gln Ala Asn Pro Arg Gly Ser Ala
1               5                   10
```

<210> SEQ ID NO 46
<211> LENGTH: 13
<212> TYPE: PRT
<213> ORGANISM: Homo sapiens

<400> SEQUENCE: 46

```
Leu Val His Gln Ala Asn Pro Arg Gly Ser Ala Gly Pro
1               5                   10
```

<210> SEQ ID NO 47
<211> LENGTH: 13
<212> TYPE: PRT
<213> ORGANISM: Homo sapiens

<400> SEQUENCE: 47

```
His Gln Ala Asn Pro Arg Gly Ser Ala Gly Pro Ser Ser
1               5                   10
```

<210> SEQ ID NO 48
<211> LENGTH: 13
<212> TYPE: PRT
<213> ORGANISM: Homo sapiens

<400> SEQUENCE: 48

Ala Asn Pro Arg Gly Ser Ala Gly Pro Ser Ser Thr Pro
1               5                   10

<210> SEQ ID NO 49
<211> LENGTH: 13
<212> TYPE: PRT
<213> ORGANISM: Homo sapiens

<400> SEQUENCE: 49

Pro Arg Gly Ser Ala Gly Pro Ser Ser Thr Pro Thr Lys
1               5                   10

<210> SEQ ID NO 50
<211> LENGTH: 13
<212> TYPE: PRT
<213> ORGANISM: Homo sapiens

<400> SEQUENCE: 50

Gly Ser Ala Gly Pro Ser Ser Thr Pro Thr Lys Met Ser
1               5                   10

<210> SEQ ID NO 51
<211> LENGTH: 13
<212> TYPE: PRT
<213> ORGANISM: Homo sapiens

<400> SEQUENCE: 51

Ala Gly Pro Ser Ser Thr Pro Thr Lys Met Ser Pro Ile
1               5                   10

<210> SEQ ID NO 52
<211> LENGTH: 13
<212> TYPE: PRT
<213> ORGANISM: Homo sapiens

<400> SEQUENCE: 52

Pro Ser Ser Thr Pro Thr Lys Met Ser Pro Ile Asn Met
1               5                   10

<210> SEQ ID NO 53
<211> LENGTH: 13
<212> TYPE: PRT
<213> ORGANISM: Homo sapiens

<400> SEQUENCE: 53

Ser Thr Pro Thr Lys Met Ser Pro Ile Asn Met Leu Tyr
1               5                   10

<210> SEQ ID NO 54
<211> LENGTH: 13
<212> TYPE: PRT
<213> ORGANISM: Homo sapiens

<400> SEQUENCE: 54

Pro Thr Lys Met Ser Pro Ile Asn Met Leu Tyr Phe Asn
1               5                   10

<210> SEQ ID NO 55

<211> LENGTH: 13
<212> TYPE: PRT
<213> ORGANISM: Homo sapiens

<400> SEQUENCE: 55

Lys Met Ser Pro Ile Asn Met Leu Tyr Phe Asn Gly Lys
1               5                   10

<210> SEQ ID NO 56
<211> LENGTH: 13
<212> TYPE: PRT
<213> ORGANISM: Homo sapiens

<400> SEQUENCE: 56

Ser Pro Ile Asn Met Leu Tyr Phe Asn Gly Lys Glu Gln
1               5                   10

<210> SEQ ID NO 57
<211> LENGTH: 13
<212> TYPE: PRT
<213> ORGANISM: Homo sapiens

<400> SEQUENCE: 57

Ile Asn Met Leu Tyr Phe Asn Gly Lys Glu Gln Ile Ile
1               5                   10

<210> SEQ ID NO 58
<211> LENGTH: 13
<212> TYPE: PRT
<213> ORGANISM: Homo sapiens

<400> SEQUENCE: 58

Met Leu Tyr Phe Asn Gly Lys Glu Gln Ile Ile Tyr Gly
1               5                   10

<210> SEQ ID NO 59
<211> LENGTH: 13
<212> TYPE: PRT
<213> ORGANISM: Homo sapiens

<400> SEQUENCE: 59

Tyr Phe Asn Gly Lys Glu Gln Ile Ile Tyr Gly Lys Ile
1               5                   10

<210> SEQ ID NO 60
<211> LENGTH: 13
<212> TYPE: PRT
<213> ORGANISM: Homo sapiens

<400> SEQUENCE: 60

Asn Gly Lys Glu Gln Ile Ile Tyr Gly Lys Ile Pro Ala
1               5                   10

<210> SEQ ID NO 61
<211> LENGTH: 13
<212> TYPE: PRT
<213> ORGANISM: Homo sapiens

<400> SEQUENCE: 61

Lys Glu Gln Ile Ile Tyr Gly Lys Ile Pro Ala Met Val
1               5                   10

<210> SEQ ID NO 62
<211> LENGTH: 13
<212> TYPE: PRT

<210> SEQ ID NO 62
<211> LENGTH: 11
<212> TYPE: PRT
<213> ORGANISM: Homo sapiens

<400> SEQUENCE: 62

Gln Ile Ile Tyr Gly Lys Ile Pro Ala Met Val Val Asp
1               5                   10

<210> SEQ ID NO 63
<211> LENGTH: 13
<212> TYPE: PRT
<213> ORGANISM: Homo sapiens

<400> SEQUENCE: 63

Ile Tyr Gly Lys Ile Pro Ala Met Val Val Asp Arg Ser
1               5                   10

<210> SEQ ID NO 64
<211> LENGTH: 13
<212> TYPE: PRT
<213> ORGANISM: Homo sapiens

<400> SEQUENCE: 64

Lys Ile Pro Ala Met Val Val Asp Arg Ser Gly Ser Ser
1               5                   10

<210> SEQ ID NO 65
<211> LENGTH: 30
<212> TYPE: PRT
<213> ORGANISM: Homo sapiens

<400> SEQUENCE: 65

Asp Phe Gly Leu Asp Ser Asp Glu His Ser Thr Glu Ser Arg Ser Ser
1               5                   10                  15

Arg Tyr Pro Leu Thr Val Asp Phe Glu Ala Phe Gly Trp Asp
            20                  25                  30

<210> SEQ ID NO 66
<211> LENGTH: 12
<212> TYPE: PRT
<213> ORGANISM: Homo sapiens

<400> SEQUENCE: 66

Gly Leu Asp Ser Asp Glu His Ser Thr Glu Ser Arg
1               5                   10

<210> SEQ ID NO 67
<211> LENGTH: 11
<212> TYPE: PRT
<213> ORGANISM: Homo sapiens

<400> SEQUENCE: 67

Gly Leu Asp Ser Asp Glu His Ser Thr Glu Ser
1               5                   10

<210> SEQ ID NO 68
<211> LENGTH: 10
<212> TYPE: PRT
<213> ORGANISM: Homo sapiens

<400> SEQUENCE: 68

Gly Leu Asp Ser Asp Glu His Ser Thr Glu
1               5                   10

<210> SEQ ID NO 69
<211> LENGTH: 9

```
<212> TYPE: PRT
<213> ORGANISM: Homo sapiens

<400> SEQUENCE: 69

Gly Leu Asp Ser Asp Glu His Ser Thr
1               5

<210> SEQ ID NO 70
<211> LENGTH: 8
<212> TYPE: PRT
<213> ORGANISM: Homo sapiens

<400> SEQUENCE: 70

Gly Leu Asp Ser Asp Glu His Ser
1               5

<210> SEQ ID NO 71
<211> LENGTH: 7
<212> TYPE: PRT
<213> ORGANISM: Homo sapiens

<400> SEQUENCE: 71

Gly Leu Asp Ser Asp Glu His
1               5

<210> SEQ ID NO 72
<211> LENGTH: 5
<212> TYPE: PRT
<213> ORGANISM: Homo sapiens

<400> SEQUENCE: 72

Gly Leu Asp Ser Asp
1               5

<210> SEQ ID NO 73
<211> LENGTH: 4
<212> TYPE: PRT
<213> ORGANISM: Homo sapiens

<400> SEQUENCE: 73

Gly Leu Asp Ser
1

<210> SEQ ID NO 74
<211> LENGTH: 3
<212> TYPE: PRT
<213> ORGANISM: Homo sapiens

<400> SEQUENCE: 74

Gly Leu Asp
1

<210> SEQ ID NO 75
<211> LENGTH: 12
<212> TYPE: PRT
<213> ORGANISM: Homo sapiens

<400> SEQUENCE: 75

Leu Asp Ser Asp Glu His Ser Thr Glu Ser Arg Ser
1               5                   10

<210> SEQ ID NO 76
<211> LENGTH: 11
<212> TYPE: PRT
<213> ORGANISM: Homo sapiens
```

-continued

```
<400> SEQUENCE: 76

Leu Asp Ser Asp Glu His Ser Thr Glu Ser Arg
1               5                   10

<210> SEQ ID NO 77
<211> LENGTH: 10
<212> TYPE: PRT
<213> ORGANISM: Homo sapiens

<400> SEQUENCE: 77

Leu Asp Ser Asp Glu His Ser Thr Glu Ser
1               5                   10

<210> SEQ ID NO 78
<211> LENGTH: 9
<212> TYPE: PRT
<213> ORGANISM: Homo sapiens

<400> SEQUENCE: 78

Leu Asp Ser Asp Glu His Ser Thr Glu
1               5

<210> SEQ ID NO 79
<211> LENGTH: 8
<212> TYPE: PRT
<213> ORGANISM: Homo sapiens

<400> SEQUENCE: 79

Leu Asp Ser Asp Glu His Ser Thr
1               5

<210> SEQ ID NO 80
<211> LENGTH: 7
<212> TYPE: PRT
<213> ORGANISM: Homo sapiens

<400> SEQUENCE: 80

Leu Asp Ser Asp Glu His Ser
1               5

<210> SEQ ID NO 81
<211> LENGTH: 6
<212> TYPE: PRT
<213> ORGANISM: Homo sapiens

<400> SEQUENCE: 81

Leu Asp Ser Asp Glu His
1               5

<210> SEQ ID NO 82
<211> LENGTH: 5
<212> TYPE: PRT
<213> ORGANISM: Homo sapiens

<400> SEQUENCE: 82

Leu Asp Ser Asp Glu
1               5

<210> SEQ ID NO 83
<211> LENGTH: 4
<212> TYPE: PRT
<213> ORGANISM: Homo sapiens

<400> SEQUENCE: 83
```

Leu Asp Ser Asp
1

<210> SEQ ID NO 84
<211> LENGTH: 3
<212> TYPE: PRT
<213> ORGANISM: Homo sapiens

<400> SEQUENCE: 84

Leu Asp Ser
1

<210> SEQ ID NO 85
<211> LENGTH: 2
<212> TYPE: PRT
<213> ORGANISM: Homo sapiens

<400> SEQUENCE: 85

Leu Asp
1

<210> SEQ ID NO 86
<211> LENGTH: 11
<212> TYPE: PRT
<213> ORGANISM: Homo sapiens

<400> SEQUENCE: 86

Asp Ser Asp Glu His Ser Thr Glu Ser Arg Ser
1               5                   10

<210> SEQ ID NO 87
<211> LENGTH: 10
<212> TYPE: PRT
<213> ORGANISM: Homo sapiens

<400> SEQUENCE: 87

Asp Ser Asp Glu His Ser Thr Glu Ser Arg
1               5                   10

<210> SEQ ID NO 88
<211> LENGTH: 8
<212> TYPE: PRT
<213> ORGANISM: Homo sapiens

<400> SEQUENCE: 88

Asp Ser Asp Glu His Ser Thr Glu
1               5

<210> SEQ ID NO 89
<211> LENGTH: 7
<212> TYPE: PRT
<213> ORGANISM: Homo sapiens

<400> SEQUENCE: 89

Asp Ser Asp Glu His Ser Thr
1               5

<210> SEQ ID NO 90
<211> LENGTH: 6
<212> TYPE: PRT
<213> ORGANISM: Homo sapiens

<400> SEQUENCE: 90

Asp Ser Asp Glu His Ser

```
1               5

<210> SEQ ID NO 91
<211> LENGTH: 5
<212> TYPE: PRT
<213> ORGANISM: Homo sapiens

<400> SEQUENCE: 91

Asp Ser Asp Glu His
1               5

<210> SEQ ID NO 92
<211> LENGTH: 4
<212> TYPE: PRT
<213> ORGANISM: Homo sapiens

<400> SEQUENCE: 92

Asp Ser Asp Glu
1

<210> SEQ ID NO 93
<211> LENGTH: 3
<212> TYPE: PRT
<213> ORGANISM: Homo sapiens

<400> SEQUENCE: 93

Asp Ser Asp
1

<210> SEQ ID NO 94
<211> LENGTH: 10
<212> TYPE: PRT
<213> ORGANISM: Homo sapiens

<400> SEQUENCE: 94

Ser Asp Glu His Ser Thr Glu Ser Arg Ser
1               5                   10

<210> SEQ ID NO 95
<211> LENGTH: 9
<212> TYPE: PRT
<213> ORGANISM: Homo sapiens

<400> SEQUENCE: 95

Ser Asp Glu His Ser Thr Glu Ser Arg
1               5

<210> SEQ ID NO 96
<211> LENGTH: 8
<212> TYPE: PRT
<213> ORGANISM: Homo sapiens

<400> SEQUENCE: 96

Ser Asp Glu His Ser Thr Glu Ser
1               5

<210> SEQ ID NO 97
<211> LENGTH: 29
<212> TYPE: PRT
<213> ORGANISM: Homo sapiens

<400> SEQUENCE: 97

Ser Asp Glu His Ser Thr Glu Ala Gly Ala Thr Cys Gly Cys Thr Gly
1               5                   10                  15
```

Thr Gly Gly Cys Thr Gly Cys Thr Cys Thr Thr Ala Ala
            20                  25

<210> SEQ ID NO 98
<211> LENGTH: 6
<212> TYPE: PRT
<213> ORGANISM: Homo sapiens

<400> SEQUENCE: 98

Ser Asp Glu His Ser Thr
1               5

<210> SEQ ID NO 99
<211> LENGTH: 5
<212> TYPE: PRT
<213> ORGANISM: Homo sapiens

<400> SEQUENCE: 99

Ser Asp Glu His Ser
1               5

<210> SEQ ID NO 100
<211> LENGTH: 4
<212> TYPE: PRT
<213> ORGANISM: Homo sapiens

<400> SEQUENCE: 100

Ser Asp Glu His
1

<210> SEQ ID NO 101
<211> LENGTH: 3
<212> TYPE: PRT
<213> ORGANISM: Homo sapiens

<400> SEQUENCE: 101

Ser Asp Glu
1

<210> SEQ ID NO 102
<211> LENGTH: 9
<212> TYPE: PRT
<213> ORGANISM: Homo sapiens

<400> SEQUENCE: 102

Asp Glu His Ser Thr Glu Ser Arg Ser
1               5

<210> SEQ ID NO 103
<211> LENGTH: 8
<212> TYPE: PRT
<213> ORGANISM: Homo sapiens

<400> SEQUENCE: 103

Asp Glu His Ser Thr Glu Ser Arg
1               5

<210> SEQ ID NO 104
<211> LENGTH: 6
<212> TYPE: PRT
<213> ORGANISM: Homo sapiens

<400> SEQUENCE: 104

Asp Glu His Ser Thr Glu
1               5

```
<210> SEQ ID NO 105
<211> LENGTH: 30
<212> TYPE: PRT
<213> ORGANISM: Homo sapiens

<400> SEQUENCE: 105

Trp Ile Ile Ala Pro Lys Arg Tyr Lys Ala Asn Tyr Ser Ser Gly Glu
1               5                   10                  15

Ser Glu Phe Val Phe Leu Gln Lys Tyr Pro His Thr His Leu
            20                  25                  30

<210> SEQ ID NO 106
<211> LENGTH: 4
<212> TYPE: PRT
<213> ORGANISM: Homo sapiens

<400> SEQUENCE: 106

Asp Glu His Ser
1

<210> SEQ ID NO 107
<211> LENGTH: 3
<212> TYPE: PRT
<213> ORGANISM: Homo sapiens

<400> SEQUENCE: 107

Asp Glu His
1

<210> SEQ ID NO 108
<211> LENGTH: 8
<212> TYPE: PRT
<213> ORGANISM: Homo sapiens

<400> SEQUENCE: 108

Glu His Ser Thr Glu Ser Arg Ser
1               5

<210> SEQ ID NO 109
<211> LENGTH: 7
<212> TYPE: PRT
<213> ORGANISM: Homo sapiens

<400> SEQUENCE: 109

Glu His Ser Thr Glu Ser Arg
1               5

<210> SEQ ID NO 110
<211> LENGTH: 6
<212> TYPE: PRT
<213> ORGANISM: Homo sapiens

<400> SEQUENCE: 110

Glu His Ser Thr Glu Ser
1               5

<210> SEQ ID NO 111
<211> LENGTH: 5
<212> TYPE: PRT
<213> ORGANISM: Homo sapiens

<400> SEQUENCE: 111

Glu His Ser Thr Glu
```

<210> SEQ ID NO 112
<211> LENGTH: 4
<212> TYPE: PRT
<213> ORGANISM: Homo sapiens

<400> SEQUENCE: 112

Glu His Ser Thr
1

<210> SEQ ID NO 113
<211> LENGTH: 3
<212> TYPE: PRT
<213> ORGANISM: Homo sapiens

<400> SEQUENCE: 113

Glu His Ser
1

<210> SEQ ID NO 114
<211> LENGTH: 30
<212> TYPE: PRT
<213> ORGANISM: Homo sapiens

<400> SEQUENCE: 114

Val His Gln Ala Asn Pro Arg Gly Ser Ala Gly Pro Ser Ser Thr Pro
1               5                   10                  15

Thr Lys Met Ser Pro Ile Asn Met Leu Tyr Phe Asn Gly Lys
            20                  25                  30

<210> SEQ ID NO 115
<211> LENGTH: 7
<212> TYPE: PRT
<213> ORGANISM: Homo sapiens

<400> SEQUENCE: 115

His Ser Thr Glu Ser Arg Ser
1               5

<210> SEQ ID NO 116
<211> LENGTH: 6
<212> TYPE: PRT
<213> ORGANISM: Homo sapiens

<400> SEQUENCE: 116

His Ser Thr Glu Ser Arg
1               5

<210> SEQ ID NO 117
<211> LENGTH: 5
<212> TYPE: PRT
<213> ORGANISM: Homo sapiens

<400> SEQUENCE: 117

His Ser Thr Glu Ser
1               5

<210> SEQ ID NO 118
<211> LENGTH: 4
<212> TYPE: PRT
<213> ORGANISM: Homo sapiens

<400> SEQUENCE: 118

```
His Ser Thr Glu
1

<210> SEQ ID NO 119
<211> LENGTH: 3
<212> TYPE: PRT
<213> ORGANISM: Homo sapiens

<400> SEQUENCE: 119

His Ser Thr
1

<210> SEQ ID NO 120
<211> LENGTH: 6
<212> TYPE: PRT
<213> ORGANISM: Homo sapiens

<400> SEQUENCE: 120

Ser Thr Glu Ser Arg Ser
1               5

<210> SEQ ID NO 121
<211> LENGTH: 5
<212> TYPE: PRT
<213> ORGANISM: Homo sapiens

<400> SEQUENCE: 121

Ser Thr Glu Ser Arg
1               5

<210> SEQ ID NO 122
<211> LENGTH: 4
<212> TYPE: PRT
<213> ORGANISM: Homo sapiens

<400> SEQUENCE: 122

Ser Thr Glu Ser
1

<210> SEQ ID NO 123
<211> LENGTH: 3
<212> TYPE: PRT
<213> ORGANISM: Homo sapiens

<400> SEQUENCE: 123

Ser Thr Glu
1

<210> SEQ ID NO 124
<211> LENGTH: 5
<212> TYPE: PRT
<213> ORGANISM: Homo sapiens

<400> SEQUENCE: 124

Thr Glu Ser Arg Ser
1               5

<210> SEQ ID NO 125
<211> LENGTH: 4
<212> TYPE: PRT
<213> ORGANISM: Homo sapiens

<400> SEQUENCE: 125

Thr Glu Ser Arg
1
```

<210> SEQ ID NO 126
<211> LENGTH: 3
<212> TYPE: PRT
<213> ORGANISM: Homo sapiens

<400> SEQUENCE: 126

Thr Glu Ser
1

<210> SEQ ID NO 127
<211> LENGTH: 4
<212> TYPE: PRT
<213> ORGANISM: Homo sapiens

<400> SEQUENCE: 127

Glu Ser Arg Ser
1

<210> SEQ ID NO 128
<211> LENGTH: 3
<212> TYPE: PRT
<213> ORGANISM: Homo sapiens

<400> SEQUENCE: 128

Glu Ser Arg
1

<210> SEQ ID NO 129
<211> LENGTH: 29
<212> TYPE: PRT
<213> ORGANISM: Homo sapiens

<400> SEQUENCE: 129

Pro Ile Asn Met Leu Tyr Phe Asn Gly Lys Glu Gln Ile Ile Tyr Gly
1               5                   10                  15

Lys Ile Pro Ala Met Val Val Asp Arg Ser Gly Ser Ser
            20                  25

<210> SEQ ID NO 130
<211> LENGTH: 375
<212> TYPE: PRT
<213> ORGANISM: Homo sapiens

<400> SEQUENCE: 130

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Phe Leu
        115                 120                 125

Met Gln Val Asp Gly Lys Pro Lys Cys Cys Phe Phe Lys Phe Ser Ser
    130                 135                 140

Lys Ile Gln Tyr Asn Lys Val Lys Ala Gln Leu Trp Ile Tyr Leu
145                 150                 155                 160

Arg Pro Val Glu Thr Pro Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285

Asp Phe Glu Ala Phe Gly Trp Asp Trp Ile Ile Ala Pro Lys Arg Tyr
    290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
        355                 360                 365

Val Asp Arg Cys Gly Cys Ser
    370                 375

<210> SEQ ID NO 131
<211> LENGTH: 263
<212> TYPE: PRT
<213> ORGANISM: Homo sapiens

<400> SEQUENCE: 131

Met Ala Gln Glu Thr Asp Pro Ala Val Gln Thr Asp Gly Ser Pro Leu
1               5                   10                  15

Cys Cys His Phe His Phe Ser Pro Lys Val Met Phe Thr Lys Val Leu
            20                  25                  30

Lys Ala Gln Leu Trp Val Tyr Leu Arg Pro Val Pro Arg Pro Ala Thr
        35                  40                  45

Val Tyr Leu Gln Ile Leu Arg Leu Lys Pro Leu Thr Gly Glu Gly Thr
    50                  55                  60

Ala Gly Gly Gly Gly Gly Arg Arg His Ile Arg Ile Arg Ser Leu
65                  70                  75                  80

Lys Ile Glu Leu His Ser Arg Ser Gly His Trp Gln Ser Ile Asp Phe
            85                  90                  95

Lys Gln Val Leu His Ser Trp Phe Arg Gln Pro Gln Ser Asn Trp Gly
        100                 105                 110

Ile Glu Ile Asn Ala Phe Asp Pro Ser Gly Thr Asp Leu Ala Val Thr

```
                    115                 120                 125
Ser Leu Gly Pro Gly Ala Glu Gly Leu His Pro Phe Met Glu Leu Arg
        130                 135                 140

Val Leu Glu Asn Thr Lys Arg Ser Arg Arg Asn Leu Gly Leu Asp Cys
145                 150                 155                 160

Asp Glu His Ser Ser Glu Ser Arg Cys Cys Arg Tyr Pro Leu Thr Val
                165                 170                 175

Asp Phe Glu Ala Phe Gly Trp Asp Trp Ile Ile Ala Pro Lys Arg Tyr
                180                 185                 190

Lys Ala Asn Tyr Cys Ser Gly Gln Cys Glu Tyr Met Phe Met Gln Lys
        195                 200                 205

Tyr Pro His Thr His Leu Val Gln Gln Ala Asn Pro Arg Gly Ser Ala
        210                 215                 220

Gly Pro Cys Cys Thr Pro Thr Lys Met Ser Pro Ile Asn Met Leu Tyr
225                 230                 235                 240

Phe Asn Asp Lys Gln Gln Ile Ile Tyr Gly Lys Ile Pro Gly Met Val
                245                 250                 255

Val Asp Arg Cys Gly Cys Ser
                260
```